US008563741B2

(12) United States Patent
Qian et al.

(10) Patent No.: US 8,563,741 B2
(45) Date of Patent: Oct. 22, 2013

(54) CDK INHIBITORS CONTAINING A ZINC BINDING MOIETY

(75) Inventors: Changgeng Qian, Wayland, MA (US); Xiong Cai, Belmont, MA (US); Haixiao Zhai, Bedford, MA (US)

(73) Assignee: Curis, Inc., Lexington, MA (US)

( * ) Notice: Subject to any disclaimer, the term of this patent is extended or adjusted under 35 U.S.C. 154(b) by 828 days.

(21) Appl. No.: 12/207,788

(22) Filed: Sep. 10, 2008

(65) Prior Publication Data

US 2009/0093507 A1 Apr. 9, 2009

Related U.S. Application Data

(60) Provisional application No. 60/971,046, filed on Sep. 10, 2007, provisional application No. 61/035,272, filed on Mar. 10, 2008.

(51) Int. Cl.
*C07D 413/14* (2006.01)
*C07D 417/14* (2006.01)
*C07D 277/38* (2006.01)
*A61K 31/505* (2006.01)
*A61K 31/425* (2006.01)
*A61K 31/445* (2006.01)

(52) U.S. Cl.
USPC ........ 548/185; 546/270.7; 544/331; 514/275; 514/369; 514/326

(58) Field of Classification Search
None
See application file for complete search history.

(56) References Cited

U.S. PATENT DOCUMENTS

| | | | |
|---|---|---|---|
| 6,413,974 | B1 | 7/2002 | Dumont et al. |
| 6,777,217 | B1 | 8/2004 | Schreiber et al. |
| 7,250,514 | B1 | 7/2007 | Xiao |
| 2001/0006976 | A1 | 7/2001 | Chen et al. |
| 2002/0061915 | A1 | 5/2002 | Kimball et al. |
| 2002/0137778 | A1 | 9/2002 | Kim et al. |
| 2005/0234033 | A1 | 10/2005 | Anandan et al. |
| 2006/0276547 | A1 | 12/2006 | Bacopoulos et al. |
| 2006/0293366 | A1 | 12/2006 | Baltzer et al. |
| 2008/0221132 | A1 | 9/2008 | Cai et al. |
| 2010/0022543 | A1 | 1/2010 | Melvin, Jr. et al. |

FOREIGN PATENT DOCUMENTS

| | | | |
|---|---|---|---|
| CN | 1910165 A | | 2/2007 |
| FR | 2865207 A1 | * | 7/2005 |
| WO | 0144217 A1 | | 6/2001 |
| WO | 0210162 A1 | | 2/2002 |
| WO | 02068396 A1 | | 9/2002 |
| WO | 2004/113353 A1 | | 12/2004 |
| WO | WO 2005073202 A1 | * | 8/2005 |
| WO | 2006082428 A2 | | 8/2006 |
| WO | 2007022258 A1 | | 2/2007 |
| WO | 2007131364 A1 | | 11/2007 |
| WO | 2008055068 A2 | | 5/2008 |
| WO | 2009002534 A1 | | 12/2008 |
| WO | 2010009155 A2 | | 1/2010 |
| WO | 2010009166 A1 | | 1/2010 |

OTHER PUBLICATIONS

Suzuki, T., et. al., "Novel Histone Deacetylase Inhibitors: Design, Synthesis, Enzyme Inhibition, and Binding Mode Study of SAHA-Based Non-hydroxamates," Bioorganic & Medicinal Chemistry Letters, 13, 2003, 4321-4326.
Kulp, Samuel K., et. al., "Antitumor Effects of a Novel Phenylbutyrate-Based Histone Deacetylase Inhibitor, (S)-HDAC-42, in Prostate Cancer," Clinical Cancer Research, 12(17): 5199-5206 (2006).
Curtin, Michael, et. al., "Histone Deacetylase Inhibitors: The Abbott Experience," Current Medicinal Chemistry, 10: 2373-2392 (2003).
Minucci, S., et. al., "Histone deacetylase inhibitors and the promise of epigenetic (and more) treatments for cancer," Nature, 6: 38-51 (2006).
Anandan, Sampath-Kumar, et. al., "Mercaptoamide-based non-hydroxamic acid type histone deacetylase inhibitors," Bioorganic and Medicinal Chemistry Letters, 15: 1969-1972 (2005).
Jacobsen, Faith E., et. al, "A New Role for Old Ligands: Discerning Chelators for Zinc Metalloproteinases," Journal of the American Chemical Society, 128: 3156-3157 (2006).
Puerta, David T., et. al, "New Beginnings for Matrix Metalloproteinase Inhibitors: Identification of High-Affinity Zinc-Binding Groups," Journal of the American Chemical Society, 126: 8388-8389 (2004).
Kim, K.S., et. al., "Discovery of Aminothiazole Inhibitors of Cyclin-Dependent Kinase 2: Synthesis, X-ray Crystallographic Analysis, and Biological Activities," J. Med. Chem., 45: 3905-3927 (2002).
Butler, Lisa M., et al., "Suberoylanilide Hydroxamic Acid, an Inhibitor of Histone Deacetylase, Suppresses the Growth of Prostate Cancer Cells in Vitro and in Vivo," Cancer Research, 60: 5165-5170 (2000).
Fischer, P.M., "Cyclin-dependent kinase inhibitors: discovery, development and target rationale for different therapeutic applications," Drugs of the Future, 30(9): 911-929 (2005).
Misra, Raj N., et. al., "N-(Cycloalkylamino)acyl-2-aminothiazole Inhibitors of Cyclin-Dependent Kinase 2. N-[5-[[[5(1,1-Dimethylethyl)-2-oxazolyl]methyl]thio]-2-thiazolyl]-4-piperidinecarboxamide (BMS-387032), a Highly Efficacious and Selective Antitumor Agent," J. Med. Chem., 47: 1719-1728 (2004).
Garcia-Sosa, A.T., et. al., "The effect of a tightly bound water molecule on scaffold diversity in the computer-aided de novo ligand design of CDK2 inhibitors," J. Mol. Model., 12: 422-431 (2006).
Hurd, Charles D., et. al., "The 2-Aminothiazoles," J. Am. Chem. Soc., 71: 4007-4010 (1949).

* cited by examiner

*Primary Examiner* — Nyeemah A Grazier
(74) *Attorney, Agent, or Firm* — Elmore Patent Law Group, P.C.; Edgar W. Harlan; Carolyn S. Elmore

(57) ABSTRACT

The present invention relates to CDK inhibitors and their use in the treatment of cell proliferative diseases such as cancer. The compounds of the invention may further act as HDAC inhibitors.

11 Claims, 3 Drawing Sheets

CDK INHIBITORS CONTAINING A ZINC BINDING MOIETY

RELATED APPLICATIONS

This application claims the benefit of U.S. Provisional Application No. 60/971,046, filed on Sep. 10, 2007 and U.S. Provisional Application No. 61/035,272, filed on Mar. 10, 2008. The entire teachings of the above applications are incorporated herein by reference.

BACKGROUND OF THE INVENTION

Cyclin-dependent kinases (CDKs) are a family of serine/threonine kinases that regulate key cellular processes including cell cycle progression and RNA transcription (Shapiro G I. *J Clin Oncol.* 2006 Apr. 10; 24(11):1770-83). Heterodimerized with regulatory cyclin units, CDKs can be generally divided into two groups based on their functions. The first group consists of core cell cycle components and governs the cell cycle transition and cell division: cyclin D-dependent kinases 4/6 and cyclin E-dependent kinase 2, which control the G1→S transition; cyclin A-dependent kinases 1/2, a critical regulator of S-phase progression; cyclin B-dependent CDK1, required for the G2→M transition; and cyclin H/CDK7, the CDK-activating kinase. The second group, so called transcriptional CDKs, includes cyclin H/CDK7 and cyclin T/CDK9 which phosphorylate the C-terminal domain (CTD) of RNA polymerase II and promote transcriptional initiation and elongation.

The deregulation of the CDK activity is detected in virtually all forms of human cancer, most frequently due to the overexpression of cyclins and loss of expression of CDK inhibitors (de Cárcer G et al., *Curr Med Chem.* 2007; 14(9): 969-85). CDK4/6 inhibition has been shown to induce potent G1 arrest in vitro and tumor regression in vivo (Lukas J et al., *Nature.* 1995 Jun. 8; 375(6531):503-6; Schreiber M et al., *Oncogene.* 1999 Mar. 4; 18(9):1663-76; Fry D W et al., *Mol Cancer Ther.* 2004 November; 3(11):1427-38). Various approaches aimed at targeting CDK2/1 have been reported to induce S and G2 arrest followed by apoptosis (Chen Y N et al., *Proc Natl Acad Sci USA.* 1999 Apr. 13; 96(8):4325-9; Chen W et al., *Cancer Res.* 2004 Jun. 1; 64(11):3949-57; Mendoza N et al., *Cancer Res.* 2003 Mar. 1; 63(5):1020-4). Inhibition of the transcriptional CDKs 7 and 9 can affect the accumulation of transcripts encoding anti-apoptosis family members, cell cycle regulators, as well as p53 and NF-κB-responsive gene targets (Lam L T et al., *Genome Biol.* 2001; 2(10): RESEARCH0041). All these effects contribute to the induction of apoptosis and also potentiation of cytotoxicity mediated by disruption of a variety of pathways in many cancer cell types (Chen R et al., *Blood.* 2005 Oct. 1; 106(7):2513-9; Pepper C et al., *Leuk Lymphoma.* 2003 February; 44(2):337-42). CDKs are therefore recognized as an attractive target for the design and development of compounds that can specifically bind and inhibit the cyclin-dependent kinase activity and its signal transduction pathway in cancer cells, and thus can serve as either diagnostic or therapeutic agents. For example, the potent and highly selective CDK2/1 inhibitor, SNS-032 (BMS-387032), and the CDK4/6 inhibitor, PD 332991, are currently in clinical trials for treatment of cancer.

Numerous reports have indicated that CDK inhibitors may be therapeutically effective in several other disease indications than cancer, including polycystic kidney disease (Ibraghimov-Beskrovnaya O, Cell Cycle. 2007, 6:776-9), mesangial proliferative glomerulonephritis, crescentic glomerulonephritis, proliferative lupus nephritis, collapsing glomerulopathy, IgA nephropathy (Soos T J et al., Drug News Perspect. 2006, 19:325-8) and Alzheimer's disease (Monaco E A & Vallano M L. Front Biosci. 2005. 10:143-59). CDKs are required for replication of many viruses such as human cytomegalovirus, herpes simplex virus type 1 and HIV-1. Specific pharmacological CDK inhibitors have demonstrated broad antiviral activities (Schang L M et al., *Antivir Chem Chemother.* 2006; 17(6):293-320; Pumfery A et al., *Curr Pharm Des.* 2006; 12(16):1949-61).

Despite the early success of certain kinase inhibitors, it has become clear that selectively targeting individual kinases can lead to the development of drug resistant tumors. Cells that have developed mutations within the drug/kinase binding pocket display a growth advantage in the presence of drug eventually leading to disease progression. Current clinical strategies aimed at combining these molecularly targeted drugs with standard chemotherapeutics, radiation, or other targeted agents will lead to novel strategies to improve overall response rate and increase the number of complete remissions.

Furthermore, elucidation of the complex and multifactorial nature of various diseases that involve multiple pathogenic pathways and numerous molecular components suggests that multi-targeted therapies may be advantageous over monotherapies. Recent combination therapies with two or more agents for many such diseases in the areas of oncology, infectious disease, cardiovascular disease and other complex pathologies demonstrate that this combinatorial approach may provide advantages with respect to overcoming drug resistance, reduced toxicity and, in some circumstances, a synergistic therapeutic effect compared to the individual components. Certain cancers have been effectively treated with such a combinatorial approach; however, treatment regimes using a cocktail of cytotoxic drugs often are limited by dose limiting toxicities and drug-drug interactions. More recent advances with molecularly targeted drugs have provided new approaches to combination treatment for cancer, allowing multiple targeted agents to be used simultaneously, or combining these new therapies with standard chemotherapeutics or radiation to improve outcome without reaching dose limiting toxicities. However, the ability to use such combinations currently is limited to drugs that show compatible pharmacologic and pharmacodynamic properties. In addition, the regulatory requirements to demonstrate safety and efficacy of combination therapies can be more costly and lengthy than corresponding single agent trials. Once approved, combination strategies may also be associated with increased costs to patients, as well as decreased patient compliance owing to the more intricate dosing paradigms required.

In the field of protein and polypeptide-based therapeutics it has become commonplace to prepare conjugates or fusion proteins that contain most or all of the amino acid sequences of two different proteins/polypeptides and that retain the individual binding activities of the separate proteins/polypeptides. This approach is made possible by independent folding of the component protein domains and the large size of the conjugates that permits the components to bind their cellular targets in an essentially independent manner. Such an approach is not, however, generally feasible in the case of small molecule therapeutics, where even minor structural modifications can lead to major changes in target binding and/or the pharmacokinetic/pharmacodynamic properties of the resulting molecule.

The use of CDK inhibitors in combination with histone deacetylases (HDAC) has been shown to produce synergistic effects. Histone acetylation is a reversible modification, with deacetylation being catalyzed by a family of enzymes termed HDAC's. HDAC's are represented by X genes in humans and are divided into four distinct classes (*J Mol Biol,* 2004, 338:1, 17-31). In mammalians class I HDAC's (HDAC1-3, and HDAC8) are related to yeast RPD3 HDAC, class 2 (HDAC4-7, HDAC9 and HDAC10) related to yeast HDA1, class 4 (HDAC11), and class 3 (a distinct class encompassing the sirtuins which are related to yeast Sir2).

Histones are subject to post-translational acetylation of the, ε-amino groups of N-terminal lysine residues, a reaction that is catalyzed by histone acetyl transferase (HAT1) (Csordas, *Biochem. J.,* 1990, 286: 23-38). Acetylation neutralizes the positive charge of the lysine side chain, and is thought to impact chromatin structure. Indeed, access of transcription factors to chromatin templates is enhanced by histone hyperacetylation, and enrichment in underacetylated histone H4 has been found in transcriptionally silent regions of the genome (Taunton et al., *Science,* 1996, 272:408-411). In the case of tumor suppressor genes, transcriptional silencing due to histone modification can lead to oncogenic transformation and cancer.

Several classes of HDAC inhibitors currently are being evaluated by clinical investigators. The first FDA approved HDAC inhibitor is Suberoylanilide hydroxamic acid (SAHA, Zolinza®) for the treatment of cutaneous T-cell lymphoma (CTCL). Other HDAC inhibitors include hydroxamic acid derivatives; PXD101 and LAQ824, are currently in the clinical development. In the benzamide class of HDAC inhibitors, MS-275, MGCD0103 and CI-994 have reached clinical trials. Moume et al. (Abstract #4725, AACR 2005), demonstrate that thiophenyl modification of benzamides significantly enhance HDAC inhibitory activity against HDAC1.

Recent advances suggest that CDK inhibitors in combination with HDAC inhibitors may provide advantageous results in the treatment of cancer. For example, HDAC inhibitor Valproic acid upregulated p16$^{INK4A}$, a CDK inhibitor, and induced apoptosis in melanoma cell lines (Valentini A et al., *Cancer Biol Ther.* 2007 February; 6(2):185-91). Trichostatin A induced cyclin D1 repression contributed to the inhibition of breast cancer cell proliferation and sensitized cells to CDK inhibitors (Alao J P et al., *Mol Cancer.* 2006 Feb. 20; 5:8). Co-administration of flavopiridol, a pan-CDK inhibitor, with HDAC inhibitors synergistically potentiated mitochondrial damage, caspase activation and cell death in human leukemia cells (Dasmahapatra G et al., *Mol Pharmacol.* 2006 January; 69(1):288-98). Combination treatment of HDAC and CDK inhibitors has now entered clinical arena in patients with leukemia and other hematologic malignancies (Grant S and Dent P, Curr. Drug Targets. 2007 June; 8(6):751-9).

Current therapeutic regimens of the types described above attempt to address the problem of drug resistance by the administration of multiple agents. However, the combined toxicity of multiple agents due to off-target side effects as well as drug-drug interactions often limits the effectiveness of this approach. Moreover, it often is difficult to combine compounds having differing pharmacokinetics into a single dosage form, and the consequent requirement of taking multiple medications at different time intervals leads to problems with patient compliance that can undermine the efficacy of the drug combinations. In addition, the health care costs of combination therapies may be greater than the cost of single molecule therapies. Furthermore, it may be more difficult to obtain regulatory approval of a combination therapy since the burden for demonstrating activity/safety of a combination of two agents may be greater than for a single agent (Dancey J & Chen H, *Nat. Rev. Drug Dis.,* 2006, 5:649). The development of novel agents that target multiple therapeutic targets selected not by virtue of cross reactivity, but through rational design will help improve patient outcome while avoiding these limitations. Thus, enormous efforts are still directed to the development of selective anti-cancer drugs as well as to new and more efficacious combinations of known anti-cancer drugs.

SUMMARY OF THE INVENTION

The present invention relates to CDK inhibitors containing zinc-binding moiety based derivatives that have enhanced and unexpected properties as inhibitors of CDK and their use in the treatment of CDK related diseases and disorders such as cancer.

The compounds of the present invention may further act as HDAC or matrix metalloproteinase (MMP) inhibitors by virtue of their ability to bind zinc ions. Surprisingly these compounds are active at multiple therapeutic targets and are effective for treating disease. Moreover, in some cases it has even more surprisingly been found that the compounds have enhanced activity when compared to the activities of combinations of separate molecules individually having the CDK and HDAC activities. In other words, the combination of pharmacophores into a single molecule may provide a synergistic effect as compared to the individual pharmacophores. More specifically, it has been found that it is possible to prepare compounds that simultaneously contain a first portion of the molecule that binds zinc ions and thus permits inhibition of HDAC and/or matrix metalloproteinase (MMP) activity and at least a second portion of the molecule that permits binding to a separate and distinct target that inhibits CDK and thus provides therapeutic benefit. Preferably, the compounds of the present invention inhibit both CDK and HDAC activity.

Accordingly, the present invention provides a compound having a general formula I:

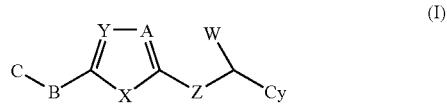

(I)

or its geometric isomers, enantiomers, diastereomers, racemates, pharmaceutically acceptable salts, prodrugs and solvates thereof, wherein Cy is selected from aryl, substituted aryl, heteroaryl, substituted heteroaryl, heterocyclic, substituted heterocyclic, cycloalkyl and substituted cycloalkyl;

W is selected from hydrogen, halogen, acyl, aliphatic, substituted aliphatic, aryl, substituted aryl, heteroaryl, substituted heteroaryl, heterocyclic, substituted heterocyclic, cycloalkyl and substituted cycloalkyl;

Z is O, S, S(O), $SO_2$, $SO_2NH$, $NR_8$, $C_1$-$C_6$ alkyl, $C_2$-$C_6$ alkenyl, $C_2$-$C_6$ alkynyl, C(O) or $C(O)NH_2$;

Y and A are independently N or $CR_8$, where $R_8$ is hydrogen, acyl, aliphatic or substituted aliphatic;

X is $CR_8$, $NR_8$, O or S;

B is a linker;

C is selected from:

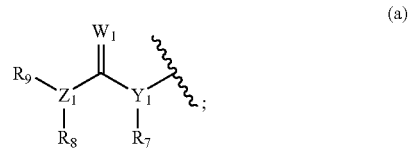

(a)

where $W_1$ is O or S; $Y_1$ is absent, N, or CH; $Z_1$ is N or CH; $R_7$ and $R_9$ are independently hydrogen, OR', aliphatic or substituted aliphatic, wherein R' is hydrogen, aliphatic, substituted aliphatic or acyl; provided that if $R_7$ and $R_9$ are both present, one of $R_7$ or $R_9$ must be OR', and if Y is absent, $R_9$ must be OR'; and $R_8$ is hydrogen, acyl, aliphatic or substituted aliphatic;

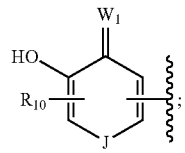
(b)

where $W_1$ is O or S; J is O, NH or $NCH_3$; and $R_{10}$ is hydrogen or lower alkyl;

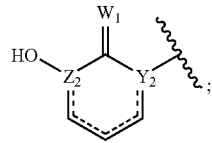
(c)

where $W_1$ is O or S; $Y_2$ and $Z_2$ are independently N, C or CH; and

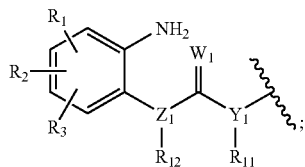
(d)

where $Z_1$, $Y_1$, and $W_1$ are as previously defined; $R_{11}$ and $R_{12}$ are independently selected from hydrogen or aliphatic; $R_1$, $R_2$ and $R_3$ are independently selected from hydrogen, hydroxy, amino, halogen, alkoxy, substituted alkoxy, alkylamino, substituted alkylamino, dialkylamino, substituted dialkylamino, substituted or unsubstituted alkylthio, substituted or unsubstituted alkylsulfonyl, $CF_3$, CN, $NO_2$, $N_3$, sulfonyl, acyl, aliphatic, substituted aliphatic, aryl, substituted aryl, heteroaryl, substituted heteroaryl, heterocyclic, and substituted heterocyclic.

One set of preferred compounds of formula I are of formula Ia

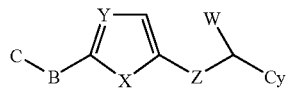
(Ia)

where C, B, Y, X, Z, W and Cy have the meanings given above for formula I.

DETAILED DESCRIPTION OF THE INVENTION

Figure 1:
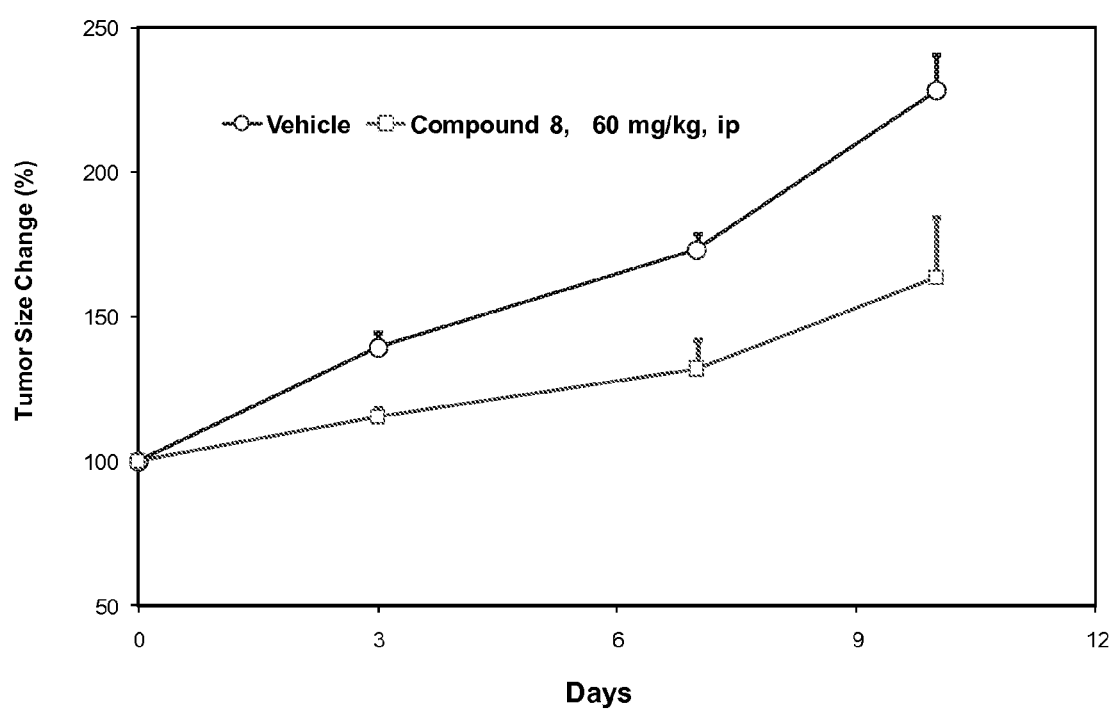
FIG. 1 is a graph of tumor size versus time for mice bearing A375 Melanoma xenograft tumors receiving either 60 mg/Kg compound 8 in 30% CAPTISOL iv daily or vehicle only.

In a first embodiment of the compounds of the present invention are compounds represented by formula (I) as illustrated above, or its geometric isomers, enantiomers, diastereomers, racemates, pharmaceutically acceptable salts, prodrugs and solvates thereof.

In one embodiment of the compounds of the present invention are compounds represented by formula (II) as illustrated below, or its geometric isomers, enantiomers, diastereomers, racemates, pharmaceutically acceptable salts, prodrugs and solvates thereof:

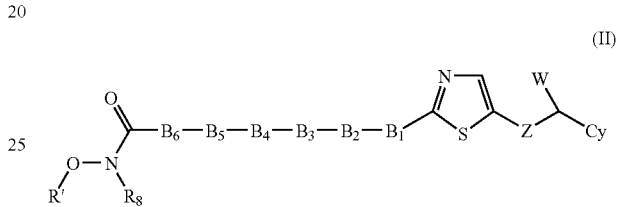
(II)

wherein $B_1$ is absent, $N(R_8)$, CO, $C_1$-$C_6$ alkyl, $C_2$-$C_6$ alkenyl, $C_2$-$C_6$ alkynyl, cycloalkyl, heterocyclic or aryl; $B_2$ is absent, O, S, SO, $SO_2$, $N(R_8)$ or CO; $B_3$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_4$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_5$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_6$ is absent, $C_1$-$C_6$ alkyl, $C_2$-$C_6$ alkenyl, $C_2$-$C_6$ alkynyl, cycloalkyl, heterocyclic, aryl, or heteroaryl; Cy, W, Z, R' and $R_8$ are as previously defined.

In one embodiment of the compounds of the present invention are compounds represented by formula (III) as illustrated below, or its geometric isomers, enantiomers, diastereomers, racemates, pharmaceutically acceptable salts, prodrugs and solvates thereof:

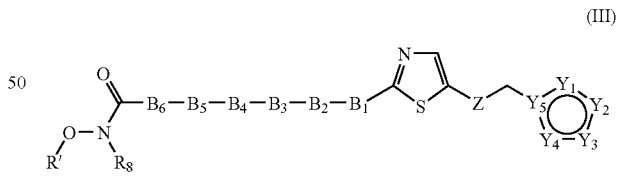
(III)

wherein $Y_1$-$Y_4$ are independently O, S, N, $NR_8$ or $CR_{21}$, where $R_{21}$ is independently selected from hydrogen, hydroxy, substituted hydroxy, amino, substituted amino, halogen, substituted or unsubstituted alkoxy, substituted or unsubstituted alkylamino, substituted or unsubstituted dialkylamino, substituted or unsubstituted thiol, $CF_3$, CN, $NO_2$, $N_3$, substituted carbonyl, sulfonyl, acyl, aliphatic, and substituted aliphatic; $Y_5$ is C or N; $B_1$ is absent, $N(R_8)$, CO, $C_1$-$C_6$ alkyl, $C_2$-$C_6$ alkenyl, $C_2$-$C_6$ alkynyl, cycloalkyl, heterocyclic or aryl; $B_2$ is absent, O, S, SO, $SO_2$, $N(R_8)$ or CO; $B_3$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_4$ is absent, O, S, SO, $SO_2$, $N(R_8)$, CO, $C_1$-$C_6$ alkyl, $C_2$-$C_6$ alkynyl, cycloalkyl, heterocyclic, aryl, or heteroaryl; $B_5$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_6$ is absent, $C_1$-$C_6$ alkyl, $C_2$-$C_6$ alkenyl, $C_2$-$C_6$ alkynyl, cycloalkyl, heterocyclic, aryl, or heteroaryl; Z, R' and $R_8$ are as previously defined. In one example, $Y_1$-$Y_4$ are independently O, S, N, $NR_8$ or $CR_{21}$, where $R_{21}$ is independently selected from hydrogen, hydroxy, amino, halogen, substituted or unsubstituted alkoxy, substituted or unsubstituted alkylamino, substituted or unsubstituted dialkylamino, $CF_3$, CN, $NO_2$, $N_3$, sulfonyl, acyl, aliphatic, and substituted aliphatic; $Y_5$ is C or N; $B_1$ is absent, $N(R_8)$, CO, $C_1$-$C_6$ alkyl, $C_2$-$C_6$ alkenyl, $C_2$-$C_6$ alkynyl, cycloalkyl, heterocyclic or aryl; $B_2$ is absent, O, S, SO, $SO_2$, $N(R_8)$ or CO; $B_3$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_4$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_5$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_6$ is absent, $C_1$-$C_6$ alkyl, $C_2$-$C_6$ alkenyl, $C_2$-$C_6$ alkynyl, cycloalkyl, heterocyclic, aryl, or heteroaryl; Z, R' and $R_8$ are as previously defined.

In one embodiment of the compounds of the present invention are compounds represented by formula (IV) as illustrated below, or its geometric isomers, enantiomers, diastereomers, racemates, pharmaceutically acceptable salts, prodrugs and solvates thereof:

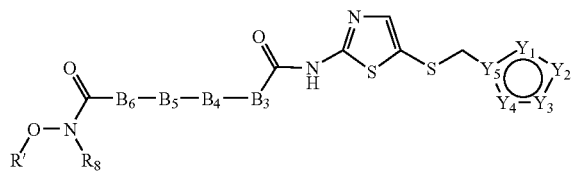

(IV)

wherein $Y_1$-$Y_4$ are independently O, S, N, $NR_8$ or $CR_{21}$, where $R_{21}$ is independently selected from hydrogen, hydroxy, substituted hydroxy, amino, substituted amino, halogen, substituted or unsubstituted alkoxy, substituted or unsubstituted alkylamino, substituted or unsubstituted dialkylamino, substituted or unsubstituted thiol, $CF_3$, CN, $NO_2$, $N_3$, substituted carbonyl, sulfonyl, acyl, aliphatic, and substituted aliphatic; $Y_5$ is C or N; $B_3$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_4$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_5$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_6$ is absent, $C_1$-$C_6$ alkyl, $C_2$-$C_6$ alkenyl, $C_2$-$C_6$ alkynyl, cycloalkyl, heterocyclic, aryl, or heteroaryl; R' and $R_8$ are as previously defined. In one example, $Y_1$-$Y_4$ are independently O, S, N, $NR_8$ or $CR_{21}$, where $R_{21}$ is independently selected from hydrogen, hydroxy, amino, halogen, substituted or unsubstituted alkoxy, substituted or unsubstituted alkylamino, substituted or unsubstituted dialkylamino, $CF_3$, CN, $NO_2$, $N_3$, sulfonyl, acyl, aliphatic, and substituted aliphatic; $Y_5$ is C or N; $B_3$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_4$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_5$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_6$ is absent, $C_1$-$C_6$ alkyl, $C_2$-$C_6$ alkenyl, $C_2$-$C_6$ alkynyl, cycloalkyl, heterocyclic, aryl, or heteroaryl; R' and $R_8$ are as previously defined.

Representative compounds according to the invention are those selected from the Table A below or its geometric isomers, enantiomers, diastereomers, racemates, pharmaceutically acceptable salts, prodrugs and solvates thereof:

TABLE A

| Compound # | Structure |
|---|---|
| 1 | 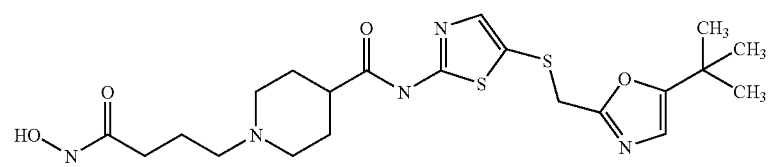 [SMILES: CC(C)(C)c1cnc(CSc2cnc(NC(=O)C3CCN(CCCC(=O)NO)CC3)s2)o1] |
| 2 | 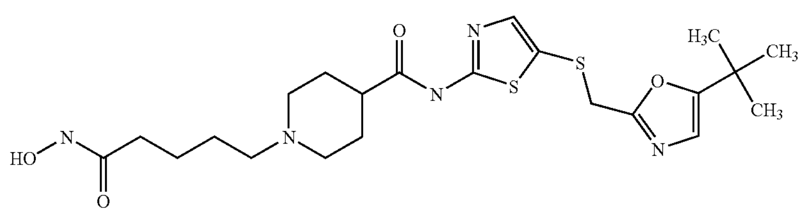 [SMILES: CC(C)(C)c1cnc(CSc2cnc(NC(=O)C3CCN(CCCCC(=O)NO)CC3)s2)o1] |
| 3 | 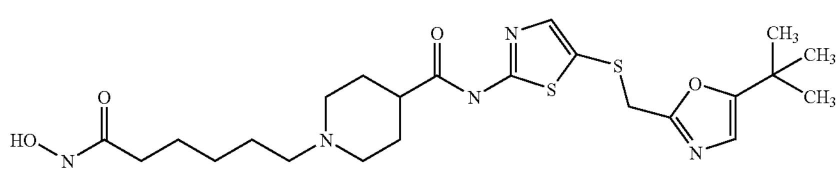 [SMILES: CC(C)(C)c1cnc(CSc2cnc(NC(=O)C3CCN(CCCCCC(=O)NO)CC3)s2)o1] |

TABLE A-continued

| Compound # | Structure |
|---|---|
| 4 | (structure) |
| 5 | (structure) |
| 6 | (structure) |
| 7 | (structure) |
| 8 | (structure) |
| 9 | (structure) |
| 10 | (structure) |
| 11 | (structure) |

TABLE A-continued
| Compound # | Structure |
|---|---|
| 12 | 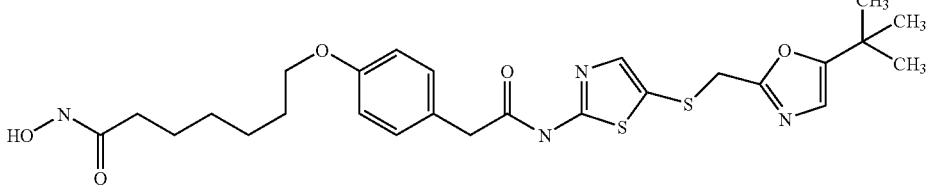 |
| 13 | 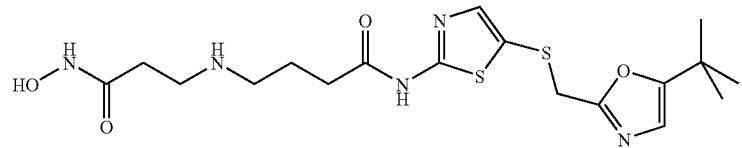 [SMILES: CC(C)(C)c1cnc(CSc2cnc(NC(=O)CCCNCCC(=O)NO)s2)o1] |
| 14 | 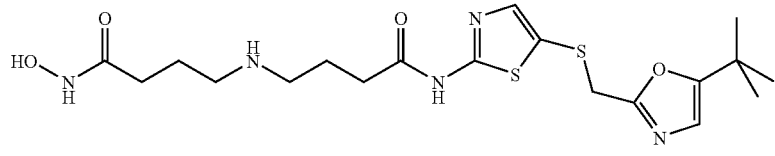 [SMILES: CC(C)(C)c1cnc(CSc2cnc(NC(=O)CCCNCCCC(=O)NO)s2)o1] |
| 15 | 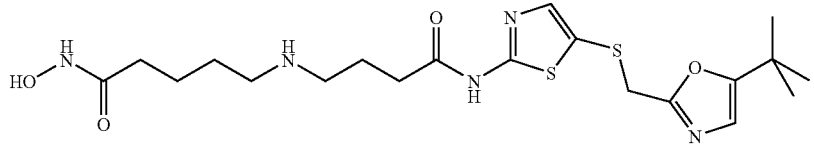 [SMILES: CC(C)(C)c1cnc(CSc2cnc(NC(=O)CCCNCCCCC(=O)NO)s2)o1] |
| 16 | 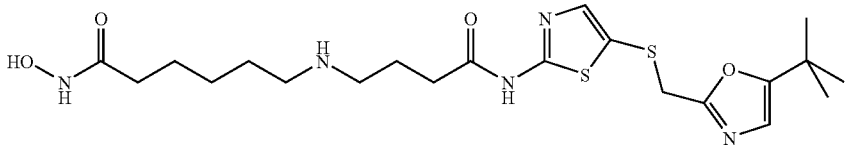 [SMILES: CC(C)(C)c1cnc(CSc2cnc(NC(=O)CCCNCCCCCC(=O)NO)s2)o1] |
| 17 | 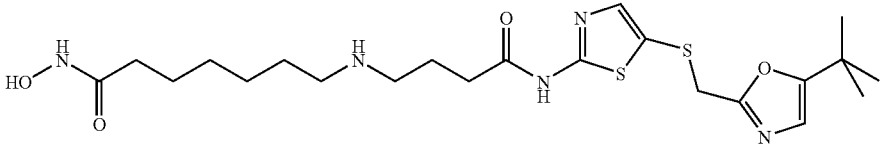 [SMILES: CC(C)(C)c1cnc(CSc2cnc(NC(=O)CCCNCCCCCCC(=O)NO)s2)o1] |
| 18 | 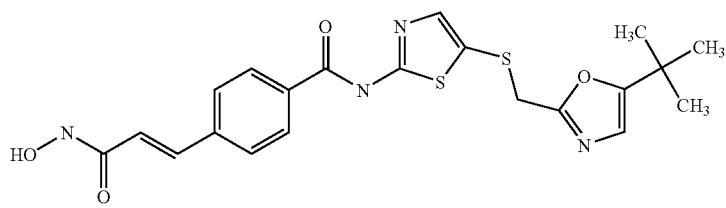 |
| 19 | 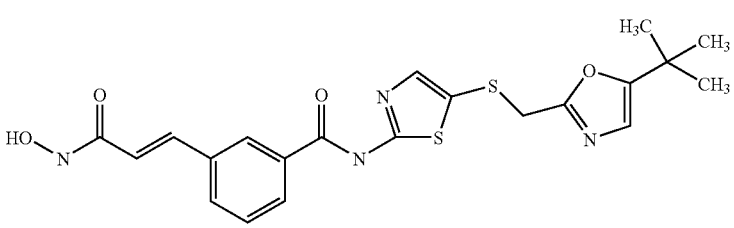 [SMILES: CC(C)(C)c1cnc(CSc2cnc(NC(=O)c3cccc(/C=C/C(=O)NO)c3)s2)o1] |

TABLE A-continued

| Compound # | Structure |
|---|---|
| 20 | 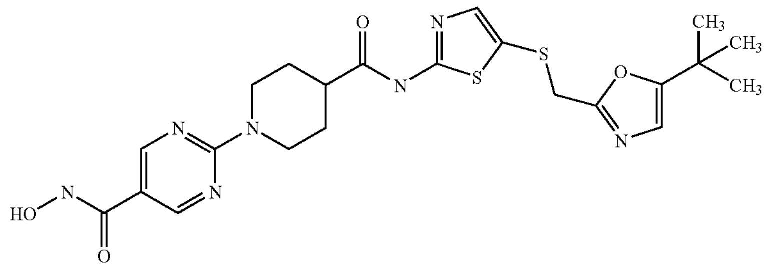 [SMILES: CC(C)(C)c1cnc(CSc2cnc(NC(=O)C3CCN(c4ncc(C(=O)NO)cn4)CC3)s2)o1] |
| 21 | 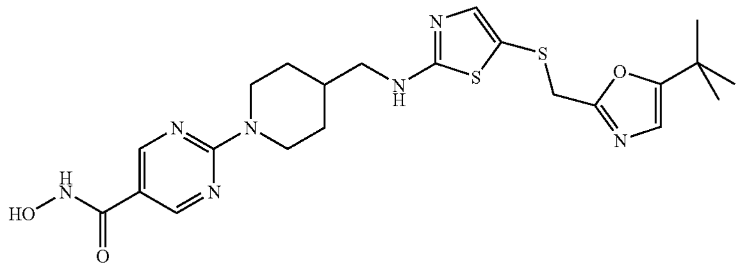 [SMILES: CC(C)(C)c1cnc(CSc2cnc(NCC3CCN(c4ncc(C(=O)NO)cn4)CC3)s2)o1] |
| 22 | 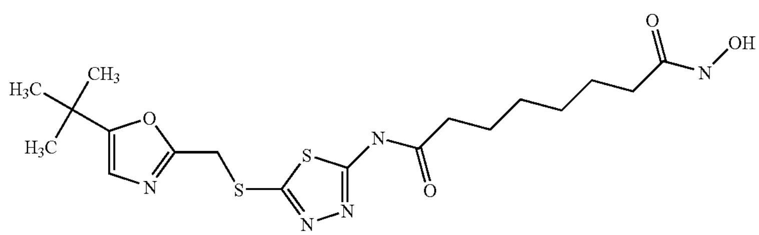 [SMILES: CC(C)(C)c1cnc(CSc2nnc(NC(=O)CCCCCCC(=O)NO)s2)o1] |
| 23 | 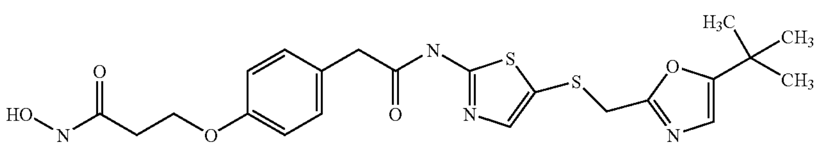 [SMILES: CC(C)(C)c1cnc(CSc2cnc(NC(=O)Cc3ccc(OCCC(=O)NO)cc3)s2)o1] |
| 24 | 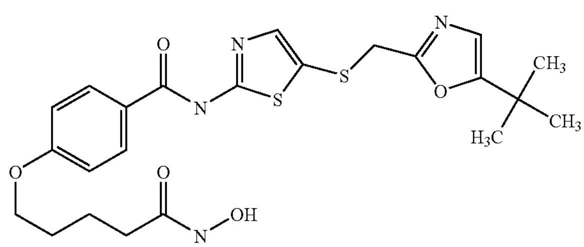 [SMILES: CC(C)(C)c1cnc(CSc2cnc(NC(=O)c3ccc(OCCCCC(=O)NO)cc3)s2)o1] |
| 25 | 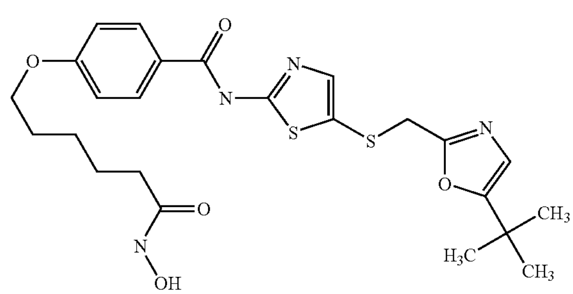 [SMILES: CC(C)(C)c1cnc(CSc2cnc(NC(=O)c3ccc(OCCCCCC(=O)NO)cc3)s2)o1] |

US 8,563,741 B2
TABLE A-continued
| Compound # | Structure |
|---|---|
| 26 | 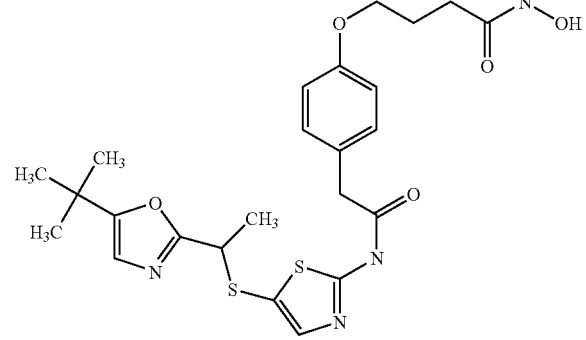 |
| 27 | 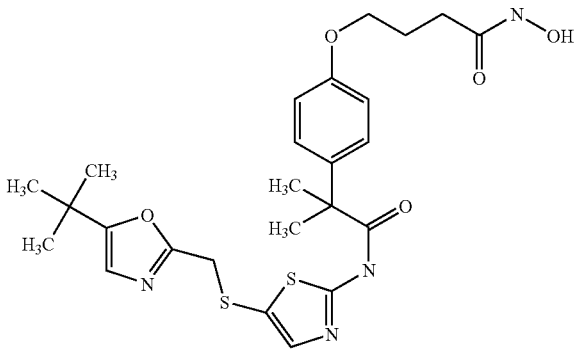 [SMILES: CC(C)(C)c1cnc(CSc2cnc(NC(=O)C(C)(C)c3ccc(OCCCC(=O)NO)cc3)s2)o1] |
| 28 | 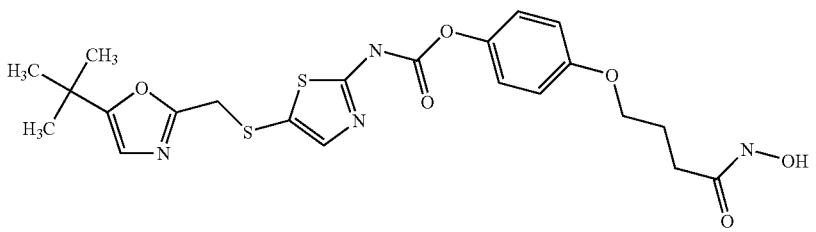 [SMILES: CC(C)(C)c1cnc(CSc2cnc(NC(=O)Oc3ccc(OCCCC(=O)NO)cc3)s2)o1] |
| 29 | 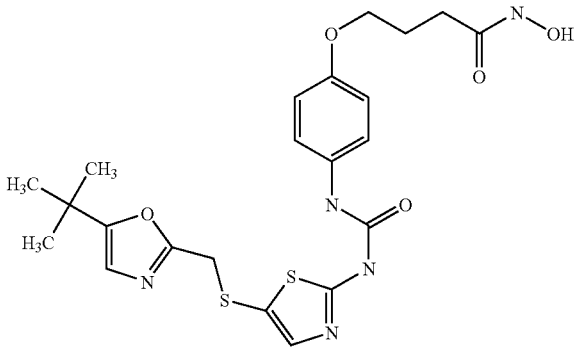 [SMILES: CC(C)(C)c1cnc(CSc2cnc(NC(=O)Nc3ccc(OCCCC(=O)NO)cc3)s2)o1] |

TABLE A-continued

| Compound # | Structure |
|---|---|
| 30 | 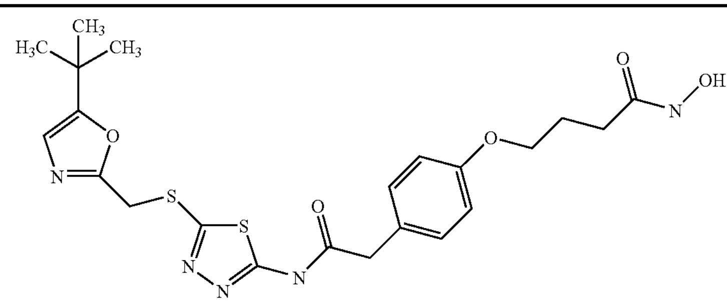 |
| 31 | 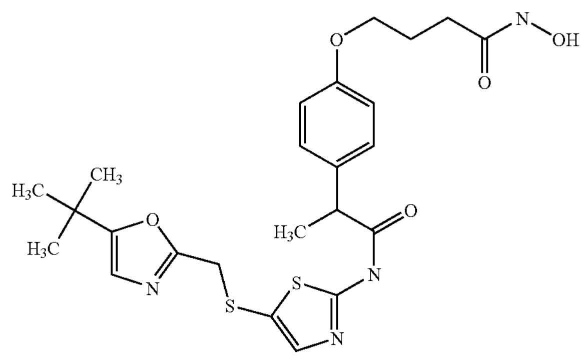 [SMILES: CC(C(=O)Nc1ncc(SCc2ncc(C(C)(C)C)o2)s1)c1ccc(OCCCC(=O)NO)cc1] |
| 32 | 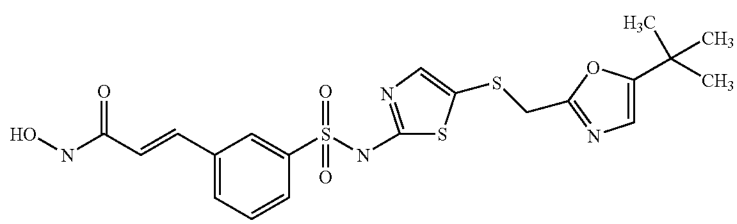 [SMILES: CC(C)(C)c1cnc(CSc2cnc(NS(=O)(=O)c3cccc(/C=C/C(=O)NO)c3)s2)o1] |
| 33 | 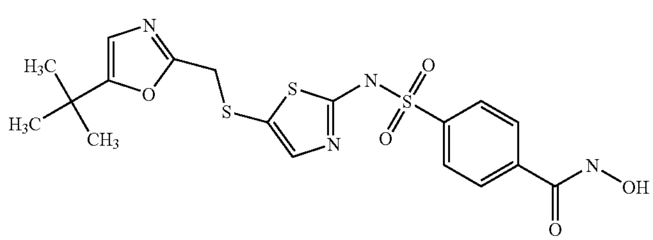 [SMILES: CC(C)(C)c1cnc(CSc2cnc(NS(=O)(=O)c3ccc(C(=O)NO)cc3)s2)o1] |
| 34 | 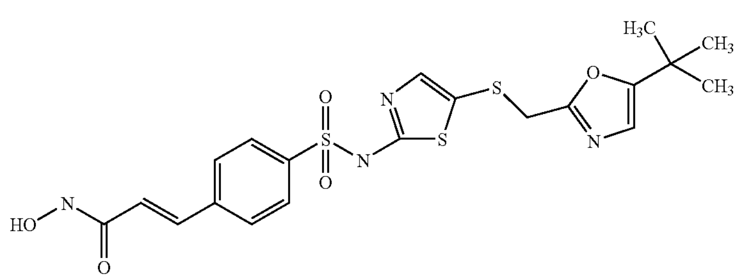 [SMILES: CC(C)(C)c1cnc(CSc2cnc(NS(=O)(=O)c3ccc(/C=C/C(=O)NO)cc3)s2)o1] |

TABLE A-continued
| Compound # | Structure |
|---|---|
| 35 | 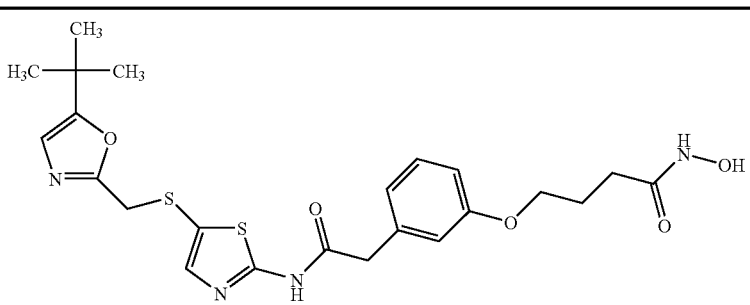 |
| 36 | 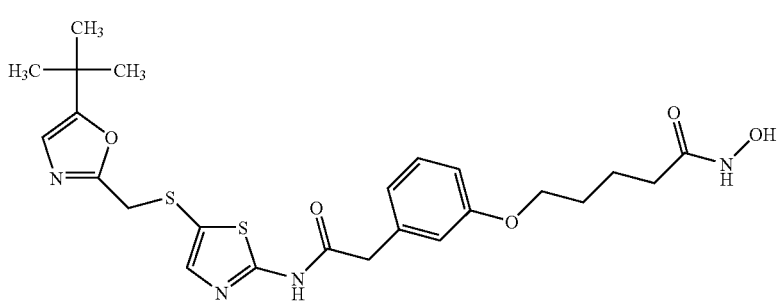 [SMILES: CC(C)(C)c1cnc(CSc2cnc(NC(=O)Cc3cccc(OCCCCC(=O)NO)c3)s2)o1] |
| 37 | 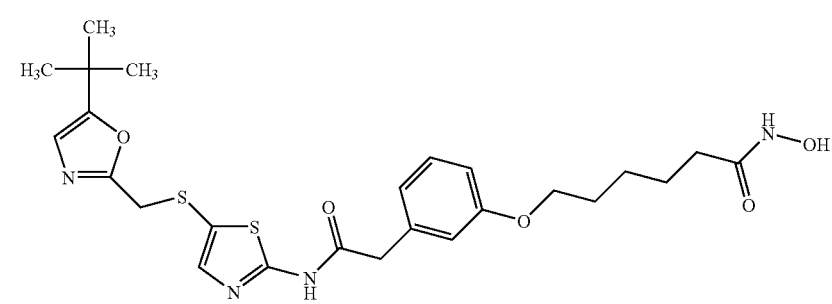 [SMILES: CC(C)(C)c1cnc(CSc2cnc(NC(=O)Cc3cccc(OCCCCCC(=O)NO)c3)s2)o1] |
| 38 | 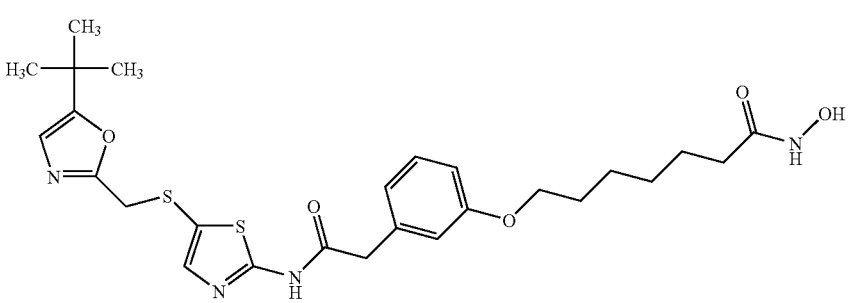 [SMILES: CC(C)(C)c1cnc(CSc2cnc(NC(=O)Cc3cccc(OCCCCCCC(=O)NO)c3)s2)o1] |
| 39 | 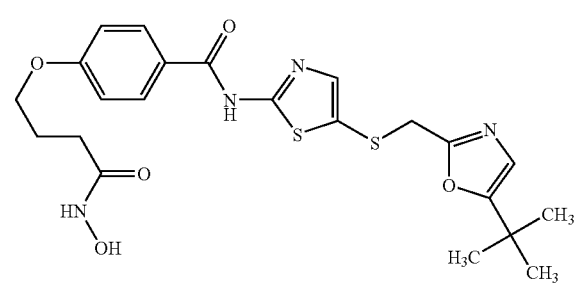 [SMILES: CC(C)(C)c1cnc(CSc2cnc(NC(=O)c3ccc(OCCCC(=O)NO)cc3)s2)o1] |

TABLE A-continued

| Compound # | Structure |
|---|---|
| 40 | 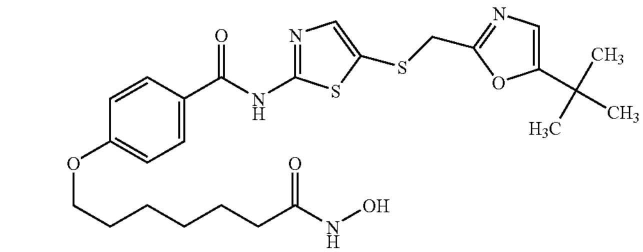 [SMILES: CC(C)(C)c1cnc(CSc2cnc(NC(=O)c3ccc(OCCCCCCC(=O)NO)cc3)s2)o1] |
| 41 | 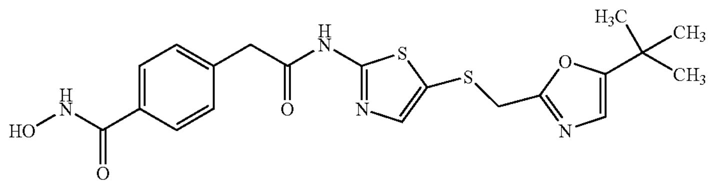 [SMILES: CC(C)(C)c1cnc(CSc2cnc(NC(=O)Cc3ccc(C(=O)NO)cc3)s2)o1] |
| 42 | 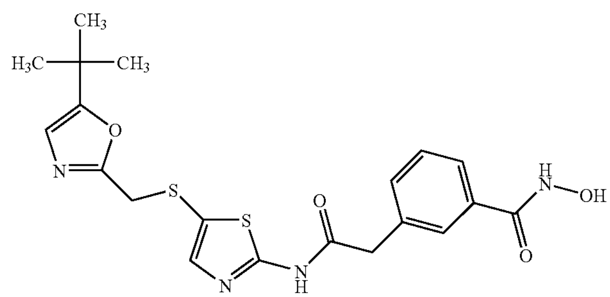 [SMILES: CC(C)(C)c1cnc(CSc2cnc(NC(=O)Cc3cccc(C(=O)NO)c3)s2)o1] |

The invention further provides methods for the prevention or treatment of diseases or conditions involving aberrant proliferation, differentiation or survival of cells. In one embodiment, the invention further provides for the use of one or more compounds of the invention in the manufacture of a medicament for halting or decreasing diseases involving aberrant proliferation, differentiation, or survival of cells. In preferred embodiments, the disease is cancer. In one embodiment, the invention relates to a method of treating cancer in a subject in need of treatment comprising administering to said subject a therapeutically effective amount of a compound of the invention.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma, renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the invention, the present invention provides for the use of one or more compounds of the invention in the manufacture of a medicament for the treatment of cancer.

In one embodiment, the present invention includes the use of one or more compounds of the invention in the manufacture of a medicament that prevents further aberrant proliferation, differentiation, or survival of cells. For example, compounds of the invention may be useful in preventing tumors from increasing in size or from reaching a metastatic state. The subject compounds may be administered to halt the progression or advancement of cancer or to induce tumor apoptosis or to inhibit tumor angiogenesis. In addition, the instant invention includes use of the subject compounds to prevent a recurrence of cancer.

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

Compounds of the invention, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of the invention, as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds the invention may also act as inhibitors of other protein kinases, e.g., protein kinase C, her2, raf 1, MEK1, MAP kinase, EGF receptor, PDGF receptor, IGF receptor, PI3 kinase, weel kinase, Src, Abl and thus be effective in the treatment of diseases associated with other protein kinases.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g, MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Axl (e.g. Mer/Nyk, Rse); RET; and platelet-derived growth factor receptor (PDGFR) (e.g. PDGFα-R, PDGFβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p43$^{abl}$, ARG); BTK (e.g. ITK/EMT, TEC); CSK, FAK, FPS, JAK, SRC, BMX, FER, CDK and SYK.

In another aspect of the invention, the subject compounds may be administered in combination with one or more separate agents that modulate non-kinase biological targets or processes. Such targets include histone deacetylases (HDAC), DNA methyltransferase (DNMT), heat shock proteins (e.g. HSP90), and proteosomes.

In a preferred embodiment, subject compounds may be combined with antineoplastic agents (e.g. small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); antimicrotubule agents (Estramustine); and retinoids (Bexarotene, Isotretinoin, Tretinoin (ATRA)).

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the invention may advantageously be used in conjunction with one or more adjunctive therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor .alpha.; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

Matrix metalloproteinases (MMPs) are a family of zinc-dependent neutral endopeptidases collectively capable of degrading essentially all matrix components. Over 20 MMP modulating agents are in pharmaceutical develop, almost half of which are indicated for cancer. The University of Toronto researchers have reported that HDACs regulate MMP expression and activity in 3T3 cells. In particular, inhibition of HDAC by trichostatin A (TSA), which has been shown to prevent tumorigenesis and metastasis, decreases mRNA as well as zymographic activity of gelatinase A (MMP2; Type IV collagenase), a matrix metalloproteinase, which is itself, implicated in tumorigenesis and metastasis (Ailenberg M., Silverman M., *Biochem Biophys Res Commun.* 2002, 298: 110-115). Another recent article that discusses the relationship of HDAC and MMPs can be found in Young D. A., et al., *Arthritis Research & Therapy,* 2005, 7: 503. Furthermore, the commonality between HDAC and MMPs inhibitors is their zinc-binding functionality. Therefore, in one aspect of the invention, compounds of the invention can be used as MMP inhibitors and may be of use in the treatment of disorders relating to or associated with dysregulation of MMP. The overexpression and activation of MMPs are known to induce tissue destruction and are also associated with a number of specific diseases including rheumatoid arthritis, periodontal disease, cancer and atherosclerosis.

The compounds may also be used in the treatment of a disorder involving, relating to or, associated with dysregulation of histone deacetylase (HDAC). There are a number of disorders that have been implicated by or known to be mediated at least in part by HDAC activity, where HDAC activity is known to play a role in triggering disease onset, or whose symptoms are known or have been shown to be alleviated by HDAC inhibitors. Disorders of this type that would be expected to be amenable to treatment with the compounds of the invention include the following but not limited to: Antiproliferative disorders (e.g. cancers); Neurodegenerative diseases including Huntington's Disease, Polyglutamine disease, Parkinson's Disease, Alzheimer's Disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Progressive supranuclear palsy, Pick's disease, intracerebral hemorrhage, Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative Diseases of the Eye including Glaucoma, Age-related macular degeneration, Rubeotic glaucoma; Inflammatory diseases and/or Immune system disorders including Rheumatoid Arthritis (RA), Osteoarthritis, Juvenile chronic arthritis, Graft versus Host disease, Psoriasis, Asthma, Spondyloarthropathy, Crohn's Disease, inflammatory bowel disease Colitis Ulcerosa, Alcoholic hepatitis, Diabetes, Sjoegrens's syndrome, Multiple Sclerosis, Ankylosing spondylitis, Membranous glomerulopathy, Discogenic pain, Systemic Lupus Erythematosus; Disease involving angiogenesis including cancer, psoriasis, rheumatoid arthritis; Psychological disorders including bipolar disease, schizophrenia, mania, depression and dementia; Cardiovascular Diseases including heart failure, restenosis and arteriosclerosis; Fibrotic diseases including liver fibrosis, cystic fibrosis and angiofibroma; Infectious diseases including Fungal infections, such as *Candida Albicans*, Bacterial infections, Viral infections, such as *Herpes Simplex*, Protozoal infections, such as *Malaria, Leishmania* infection, *Trypanosoma brucei* infection, Toxoplasmosis and coccidlosis and Haematopoietic disorders including thalassemia, anemia and sickle cell anemia.

In one embodiment, compounds of the invention can be used to induce or inhibit apoptosis, a physiological cell death process critical for normal development and homeostasis. Alterations of apoptotic pathways contribute to the pathogenesis of a variety of human diseases. Compounds of the invention, as modulators of apoptosis, will be useful in the treatment of a variety of human diseases with aberrations in apoptosis including cancer (particularly, but not limited to, follicular lymphomas, carcinomas with p53 mutations, hormone dependent tumors of the breast, prostate and ovary, and precancerous lesions such as familial adenomatous polyposis), viral infections (including, but not limited to, herpes virus, poxvirus, Epstein-Barr virus, Sindbis virus and adenovirus), autoimmune diseases (including, but not limited to, systemic lupus, erythematosus, immune mediated glomerulonephritis, rheumatoid arthritis, psoriasis, inflammatory bowel diseases, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including, but not limited to, chronic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

In one aspect, the invention provides the use of compounds of the invention for the treatment and/or prevention of immune response or immune-mediated responses and diseases, such as the prevention or treatment of rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; to treat or prevent graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treat infectious diseases causing aberrant immune response and/or activation, such as traumatic or pathogen induced immune disregulation, including for example, that which are caused by hepatitis B and C infections, HIV, *staphylococcus aureus* infection, viral encephalitis, sepsis, parasitic diseases wherein damage is induced by an inflammatory response (e.g., leprosy); and to prevent or treat circulatory diseases, such as arteriosclerosis, atherosclerosis, vasculitis, polyarteritis nodosa and myocarditis. In addition, the present invention may be used to prevent/suppress an immune response associated with a gene therapy treatment, such as the introduction of foreign genes into autologous cells and expression of the encoded product. Thus in one embodiment, the invention relates to a method of treating an immune response disease or disorder or an immune-mediated response or disorder in a subject in need of treatment comprising administering to said subject a therapeutically effective amount of a compound of the invention.

In one aspect, the invention provides the use of compounds of the invention in the treatment of a variety of neurodegenerative diseases, a non-exhaustive list of which includes: I. Disorders characterized by progressive dementia in the absence of other prominent neurologic signs, such as Alzheimer's disease; Senile dementia of the Alzheimer type; and Pick's disease (lobar atrophy); II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy); III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome; IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders); V. Syndrome of central autonomic nervous system failure (Shy-Drager syndrome); VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia; VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy; VIII Syndromes of progressive visual loss such as pigmentary degeneration of the retina (retinitis pigmentosa), and hereditary optic atrophy (Leber's disease). Furthermore, compounds of the invention can be implicated in chromatin remodeling.

The invention encompasses pharmaceutical compositions comprising pharmaceutically acceptable salts of the compounds of the invention as described above. The invention also encompasses pharmaceutical compositions comprising hydrates of the compounds of the invention. The term "hydrate" includes but is not limited to hemihydrate, monohydrate, dihydrate, trihydrate and the like. The invention further encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

The compounds of the invention, and derivatives, fragments, analogs, homologs, pharmaceutically acceptable salts or hydrate thereof can be incorporated into pharmaceutical compositions suitable for administration, together with a pharmaceutically acceptable carrier or excipient. Such compositions typically comprise a therapeutically effective amount of any of the compounds above, and a pharmaceutically acceptable carrier. Preferably, the effective amount when treating cancer is an amount effective to selectively induce terminal differentiation of suitable neoplastic cells and less than an amount which causes toxicity in a patient.

Compounds of the invention may be administered by any suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semi-solid or liquid preparation (tablet, pellet, troche, capsule, suppository, cream, ointment, aerosol, powder, liquid, emulsion, suspension, syrup, injection etc.) containing a compound of the invention as an active ingredient, which is suitable for selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and may additionally comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCI., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, e.g., treatment for a number of consecutive days followed by a rest period. The compounds of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In one embodiment, the concentration of the compound in the patient's plasma is maintained at about 25 nM. In one embodiment, the concentration of the compound in the patient's plasma is maintained at about 50 nM. In one embodiment, the concentration of the compound in the patient's plasma is maintained at about 100 nM. In one embodiment, the concentration of the compound in the patient's plasma is maintained at about 500 nM. In one embodiment, the concentration of the compound in the patient's plasma is maintained at about 1000 nM. In one embodiment, the concentration of the compound in the patient's plasma is maintained at about 2500 nM. In one embodiment, the concentration of the compound in the patient's plasma is maintained at about 5000 nM. The optimal amount of the compound that should be administered to the patient in the practice of the present invention will depend on the particular compound used and the type of cancer being treated.

DEFINITIONS

Listed below are definitions of various terms used to describe this invention. These definitions apply to the terms as they are used throughout this specification and claims, unless otherwise limited in specific instances, either individually or as part of a larger group.

An "aliphatic group" or "aliphatic" is non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. An aliphatic group, when used as a linker, preferably contains between about 1 and about 24 atoms, more preferably between about 4 to about 24 atoms, more preferably between about 4-12 atoms, more typically between about 4 and about 8 atoms. An aliphatic group, when used as a substituent, preferably contains between about 1 and about 24 atoms, more preferably between about 1 to about 10 atoms, more preferably between about 1-8 atoms, more typically between about 1 and about 6 atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl groups described herein.

The term "substituted carbonyl" includes compounds and moieties which contain a carbon connected with a double bond to an oxygen atom, and tautomeric forms thereof. Examples of moieties that contain a substituted carbonyl include aldehydes, ketones, carboxylic acids, amides, esters, anhydrides, etc. The term "carboxy moiety" or "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide).

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten carbon atoms and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten carbon atoms and more preferably about two to about eight carbon atoms. Examples of alkynyl radicals include propargyl, 1-propynyl, 2-propynyl, 1-butyne, 2-butynyl and 1-pentynyl.

The term "cycloalkyl" embraces saturated carbocyclic radicals having three to about twelve carbon atoms. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkenyl" embraces partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkoxy" embraces linear or branched oxy-containing radicals each having alkyl portions of one to about twenty carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" embraces alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" embrace saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" embraces heterocyclo-substituted alkyl radicals. More preferred heterocycloalkyl radicals are "lower heterocycloalkyl" radicals having one to six carbon atoms in the heterocyclo radicals.

The term "alkylthio" embraces radicals containing a linear or branched alkyl radical, of one to about ten carbon atoms attached to a divalent sulfur atom. Preferred alkylthio radicals have alkyl radicals of one to about twenty carbon atoms or, preferably, one to about twelve carbon atoms. More preferred alkylthio radicals have alkyl radicals are "lower alkylthio" radicals having one to about ten carbon atoms. Most preferred are alkylthio radicals having lower alkyl radicals of one to about eight carbon atoms. Examples of such lower alkylthio radicals are methylthio, ethylthio, propylthio, butylthio and hexylthio.

The terms "aralkyl" or "arylalkyl" embrace aryl-substituted alkyl radicals such as benzyl, diphenylmethyl, triphenylmethyl, phenylethyl, and diphenylethyl.

The term "aryloxy" embraces aryl radicals attached through an oxygen atom to other radicals.

The terms "aralkoxy" or "arylalkoxy" embrace aralkyl radicals attached through an oxygen atom to other radicals.

The term "aminoalkyl" embraces alkyl radicals substituted with amino radicals. Preferred aminoalkyl radicals have alkyl radicals having about one to about twenty carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "linker" means an organic moiety that connects two parts of a compound. Linkers typically comprise a direct bond or an atom such as oxygen or sulfur, a unit such as $NR_8$, $C(O)$, $C(O)NH$, $SO$, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylheterocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by $O$, $S$, $S(O)$, $SO_2$, $N(R_8)$, $C(O)$, substituted or unsubstituted aryl, substituted or unsubstituted heteroaryl, substituted or unsubstituted heterocyclic; where $R_8$ is hydrogen, acyl, aliphatic or substituted aliphatic. In one embodiment, the linker B is between 1-24 atoms, preferably 4-24 atoms, preferably 4-18 atoms, more preferably 4-12 atoms, and most preferably about 4-10 atoms.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

As used herein, the term "aberrant proliferation" refers to abnormal cell growth.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The term "angiogenesis," as used herein, refers to the formation of blood vessels. Specifically, angiogenesis is a multi-step process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175-203 (1985)). Anti-angiogenic agents interfere with this process. Examples of agents that interfere with several of these steps include thrombospondin-1, angiostatin, endostatin, interferon alpha and compounds such as matrix metalloproteinase (MMP) inhibitors that block the actions of enzymes that clear and create paths for newly forming blood vessels to follow; compounds, such as .alpha.v.beta.3 inhibitors, that interfere with molecules that blood vessel cells use to bridge between a parent blood vessel and a tumor; agents, such as specific COX-2 inhibitors, that prevent the growth of cells that form new blood vessels; and protein-based compounds that simultaneously interfere with several of these targets.

The term "apoptosis" as used herein refers to programmed cell death as signaled by the nuclei in normally functioning human and animal cells when age or state of cell health and condition dictates. An "apoptosis inducing agent" triggers the process of programmed cell death.

The term "cancer" as used herein denotes a class of diseases or disorders characterized by uncontrolled division of cells and the ability of these cells to invade other tissues, either by direct growth into adjacent tissue through invasion or by implantation into distant sites by metastasis.

The term "compound" is defined herein to include pharmaceutically acceptable salts, solvates, hydrates, polymorphs, enantiomers, diastereoisomers, racemates and the like of the compounds having a formula as set forth herein.

The term "devices" refers to any appliance, usually mechanical or electrical, designed to perform a particular function.

As used herein, the term "dysplasia" refers to abnormal cell growth, and typically refers to the earliest form of pre-cancerous lesion recognizable in a biopsy by a pathologist.

The term "hyperplasia," as used herein, refers to excessive cell division or growth.

The phrase an "immunotherapeutic agent" refers to agents used to transfer the immunity of an immune donor, e.g., another person or an animal, to a host by inoculation. The term embraces the use of serum or gamma globulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "metastasis," as used herein, refers to the migration of cancer cells from the original tumor site through the blood and lymph vessels to produce cancers in other tissues. Metastasis also is the term used for a secondary cancer growing at a distant site.

The term "neoplasm," as used herein, refers to an abnormal mass of tissue that results from excessive cell division. Neoplasms may be benign (not cancerous), or malignant (cancerous) and may also be called a tumor. The term "neoplasia" is the pathological process that results in tumor formation.

As used herein, the term "pre-cancerous" refers to a condition that is not malignant, but is likely to become malignant if left untreated.

The term "proliferation" refers to cells undergoing mitosis.

The phrase a "radio therapeutic agent" refers to the use of electromagnetic or particulate radiation in the treatment of neoplasia.

The term "recurrence" as used herein refers to the return of cancer after a period of remission. This may be due to incomplete removal of cells from the initial cancer and may occur locally (the same site of initial cancer), regionally (in vicinity of initial cancer, possibly in the lymph nodes or tissue), and/or distally as a result of metastasis.

The term "treatment" refers to any process, action, application, therapy, or the like, wherein a mammal, including a human being, is subject to medical aid with the object of improving the mammal's condition, directly or indirectly.

The term "vaccine" includes agents that induce the patient's immune system to mount an immune response against the tumor by attacking cells that express tumor associated antigens (Teas).

As used herein, the term "effective amount of the subject compounds," with respect to the subject method of treatment, refers to an amount of the subject compound which, when delivered as part of desired dose regimen, brings about, e.g. a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "pre-cancerous" refers to a condition that is not malignant, but is likely to become malignant if left untreated.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers and/or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha- ($\alpha$), beta-(B) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al, and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Synthetic Methods

The compounds of formulae I and II, or a pharmaceutically-acceptable salt thereof, may be prepared by any process known to be applicable to the preparation of chemically-related compounds. Suitable processes for making certain intermediates include, for example, those illustrated in U.S. Pat. No. 6,413,974. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of a chemist.

The compounds and processes of the present invention will be better understood in connection with the following representative synthetic schemes that illustrate the methods by which the compounds of the invention may be prepared, which are intended as an illustration only and not limiting of the scope of the invention.

Scheme 1
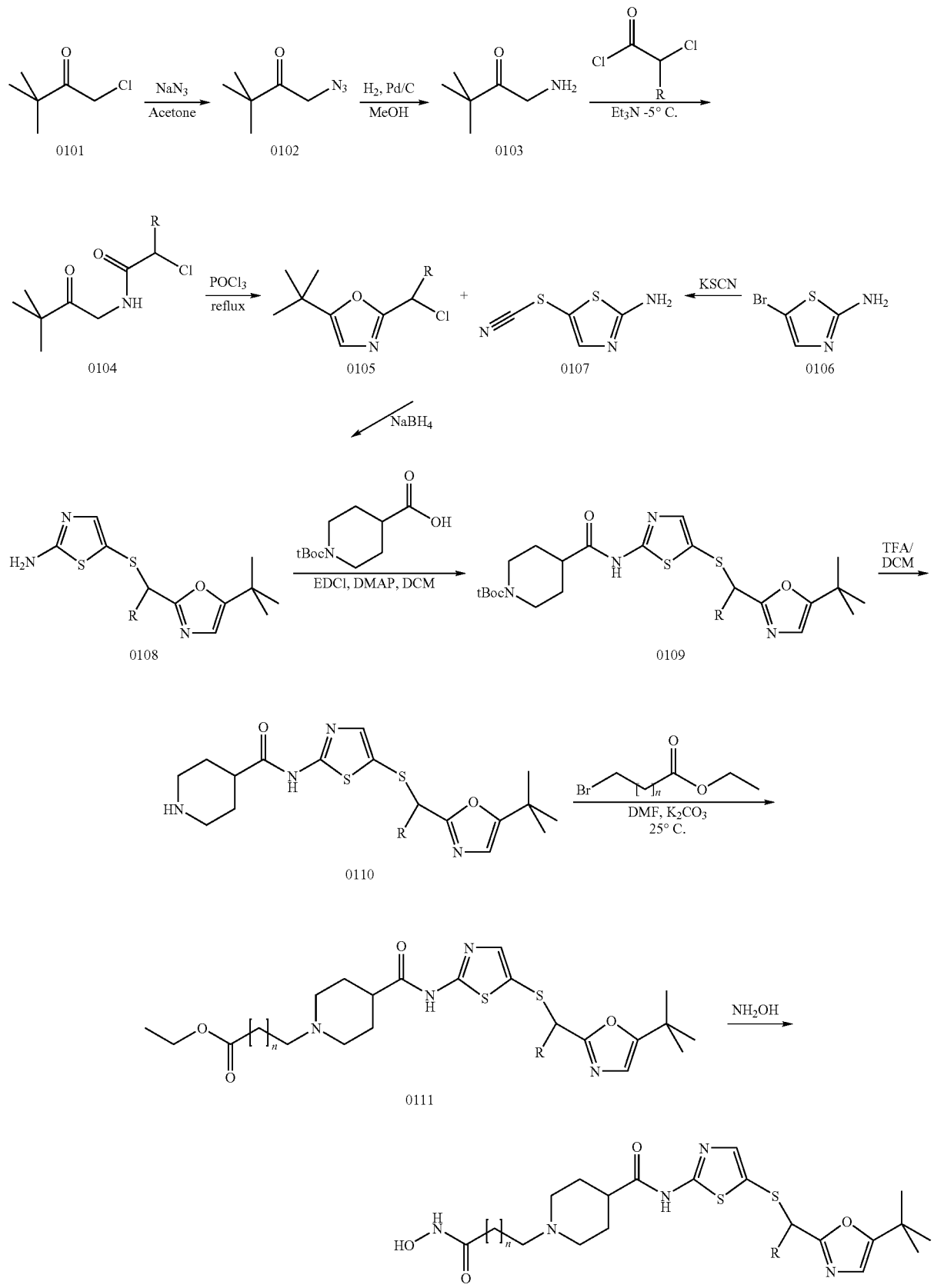

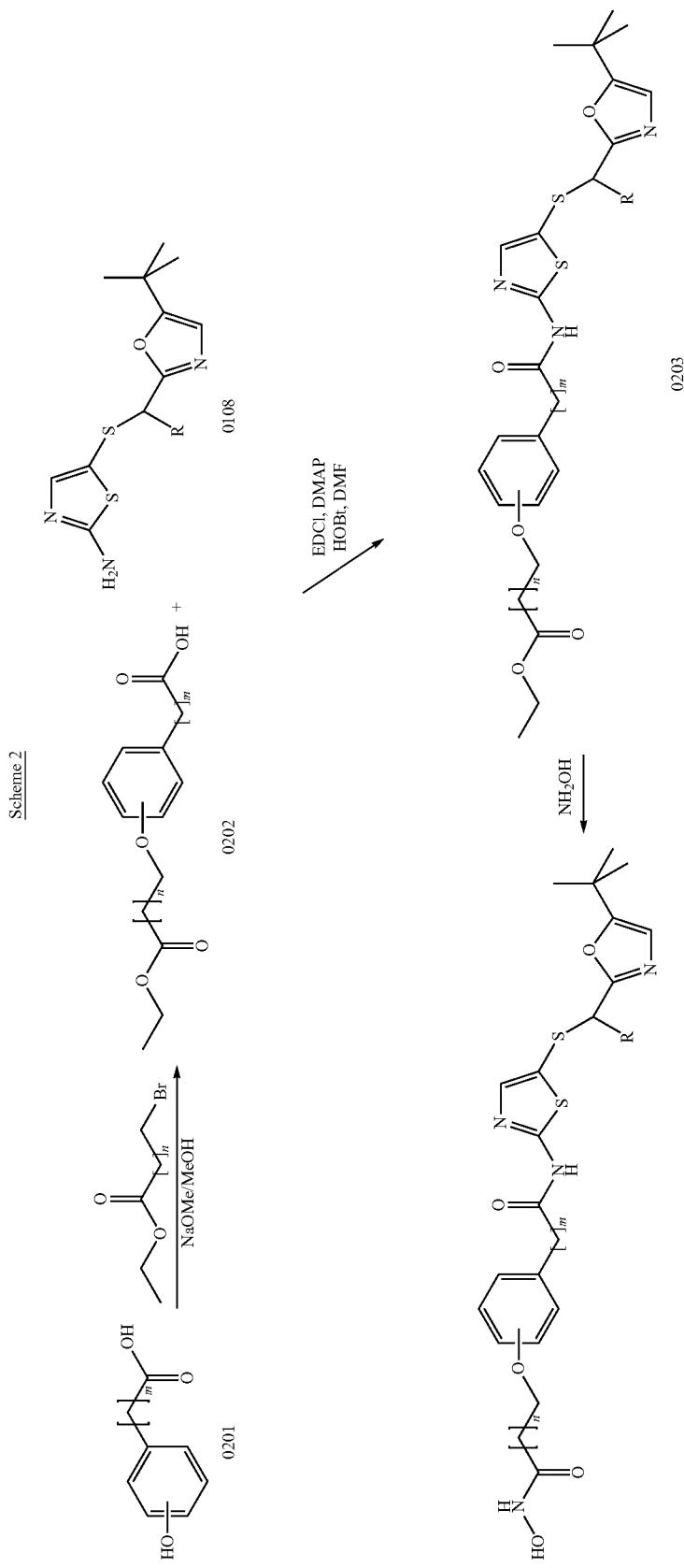

Scheme 3
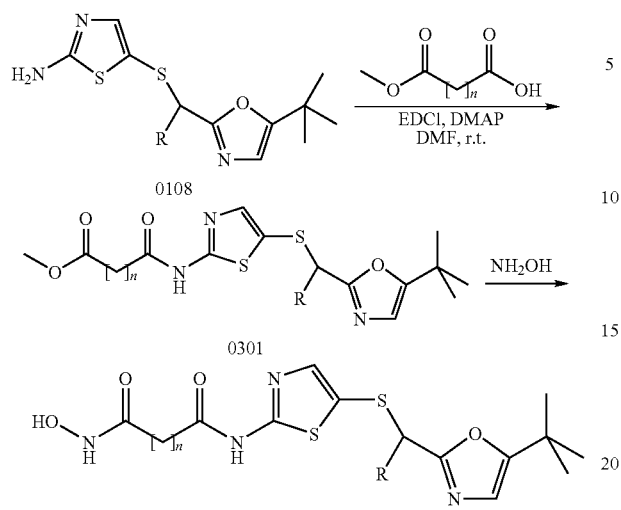
Scheme 4
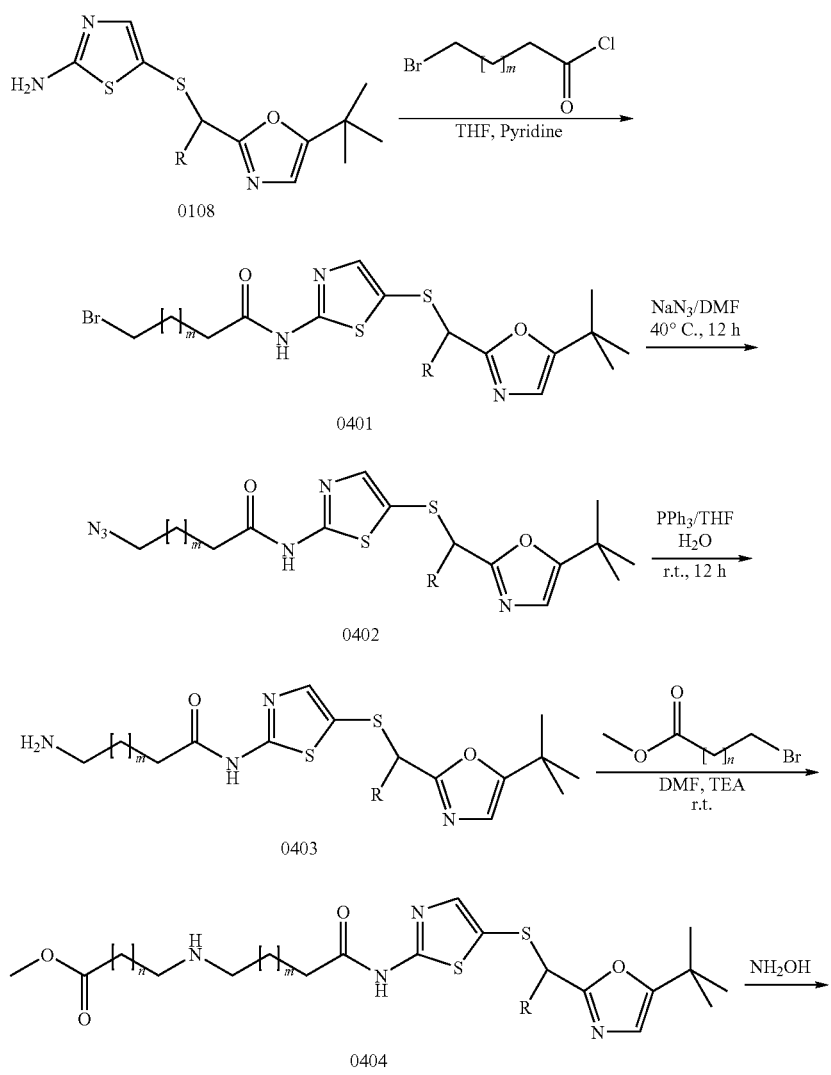

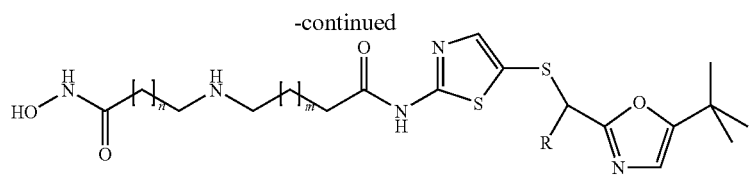
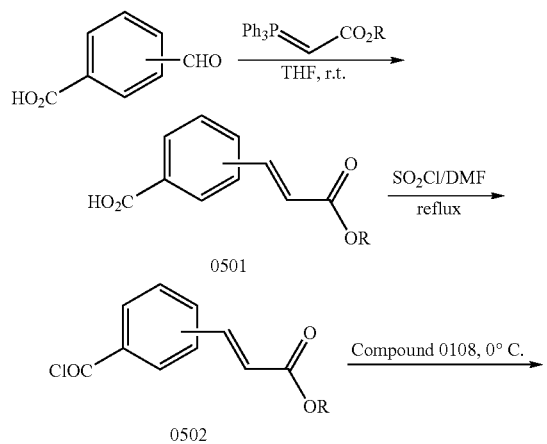
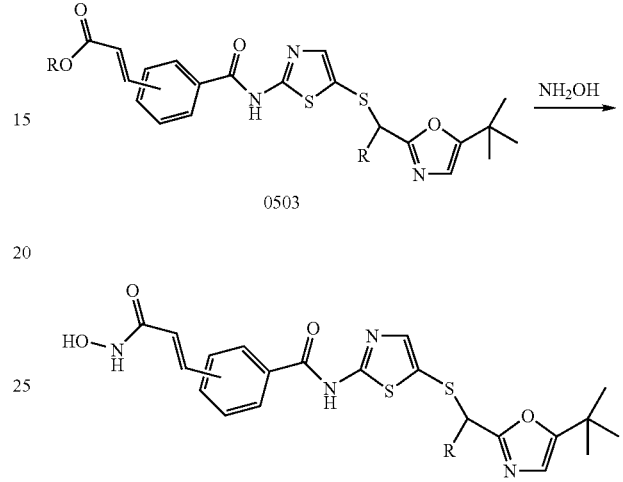
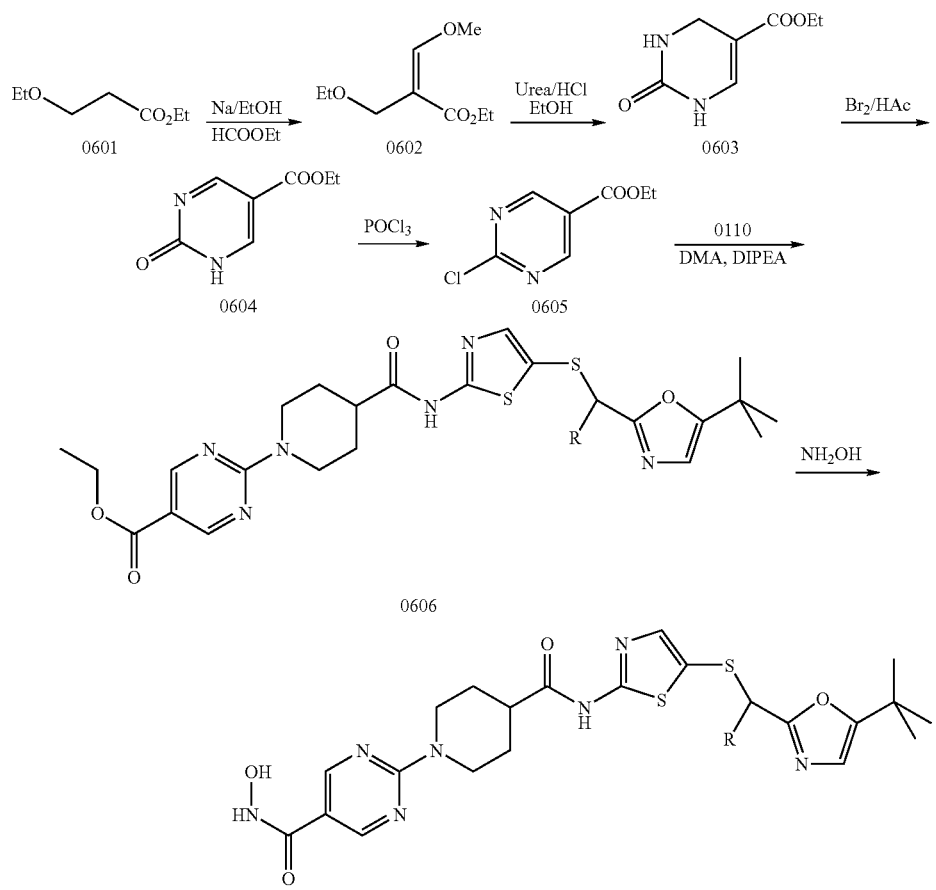

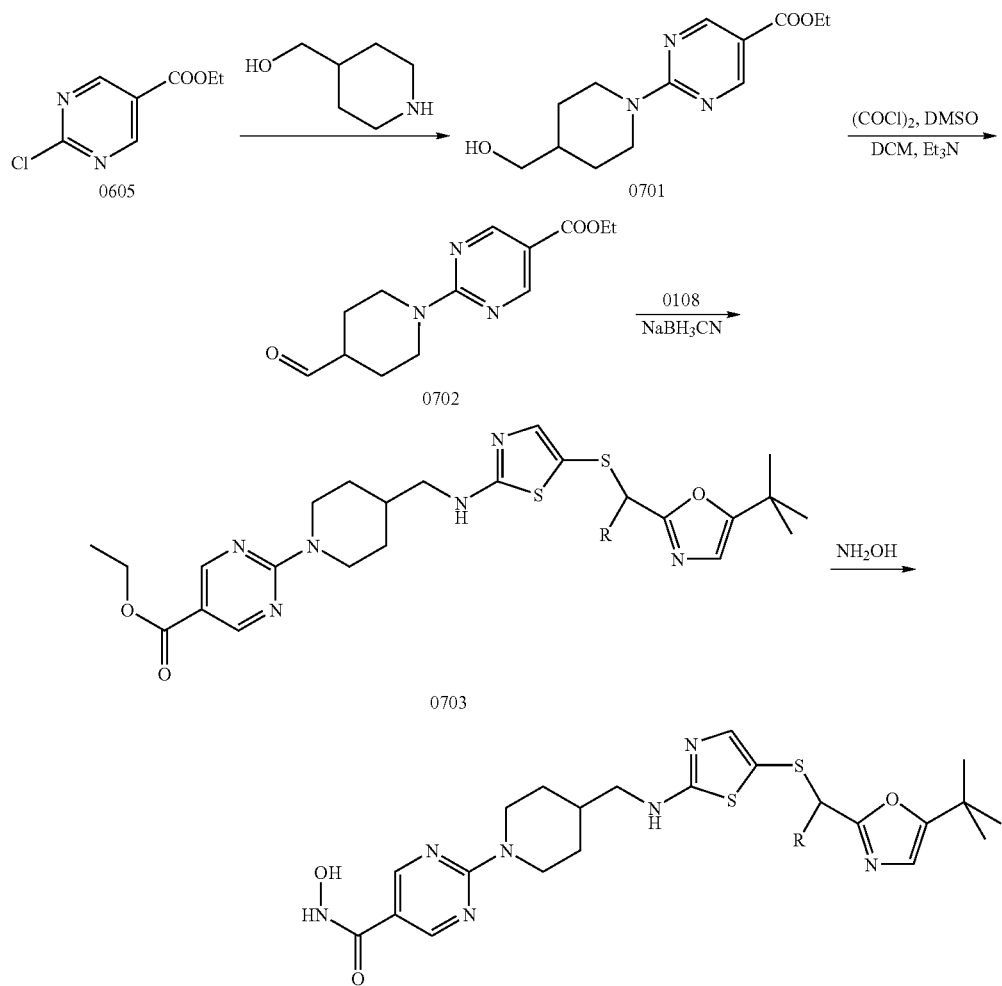
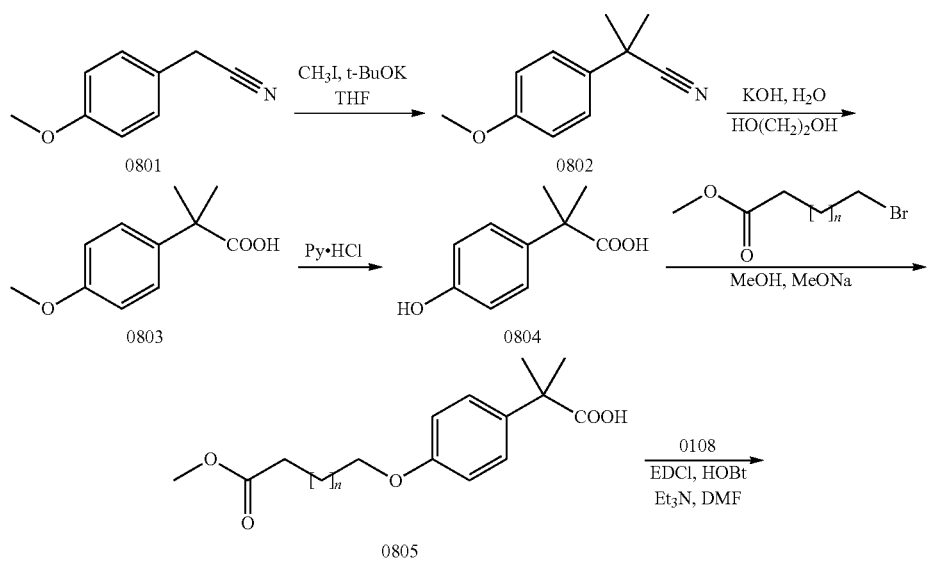

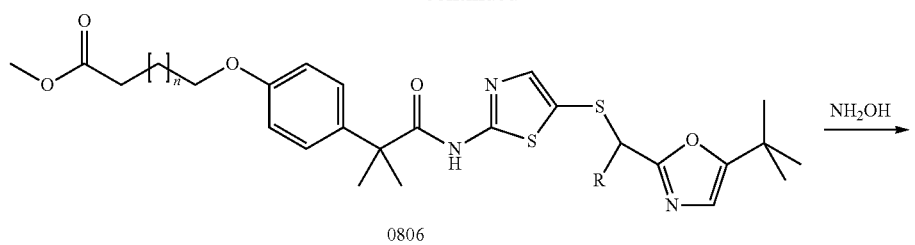
0806
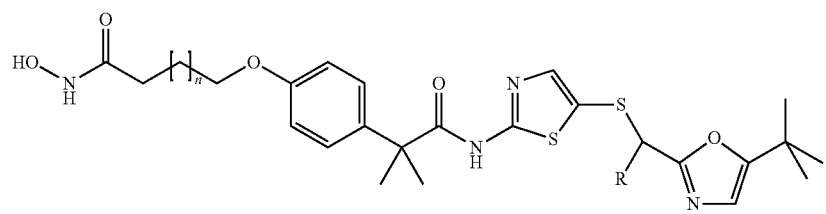
Scheme 9
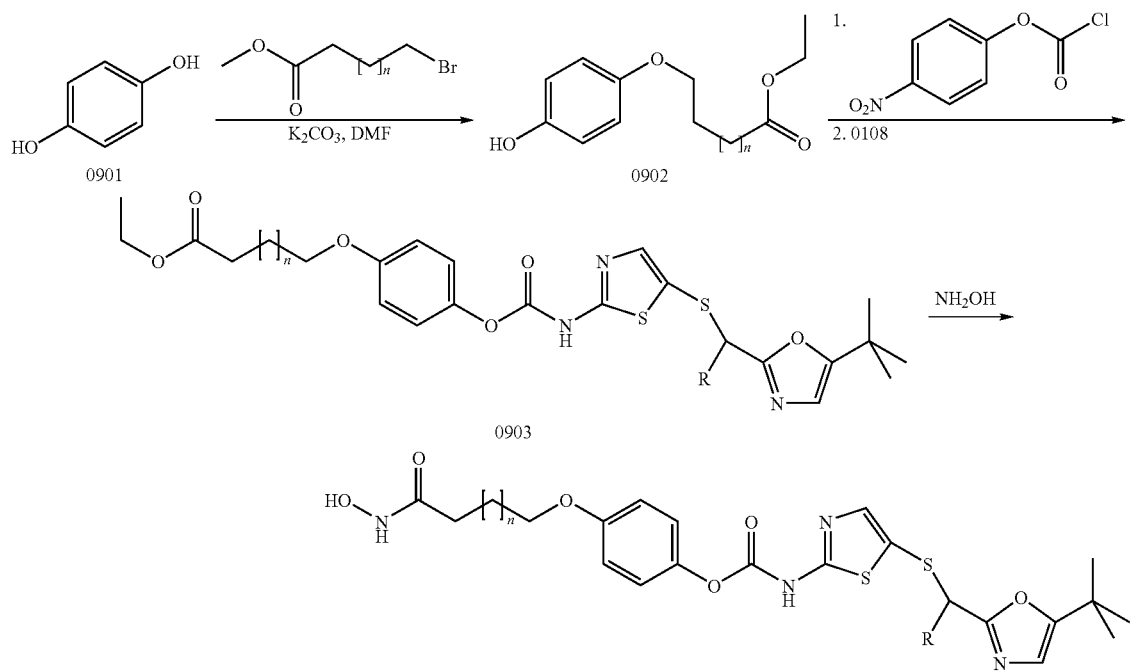
0903
Scheme 10
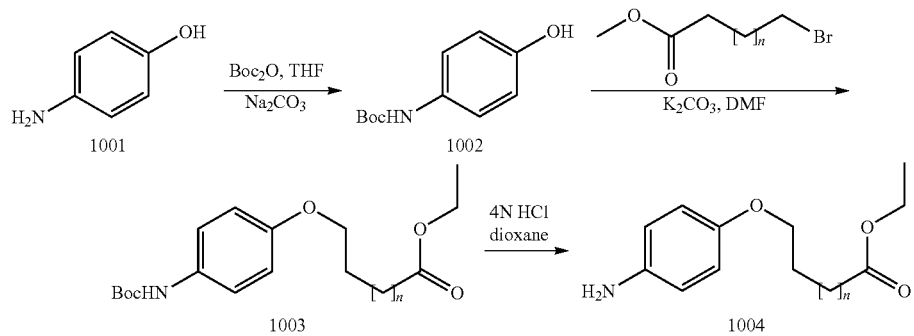

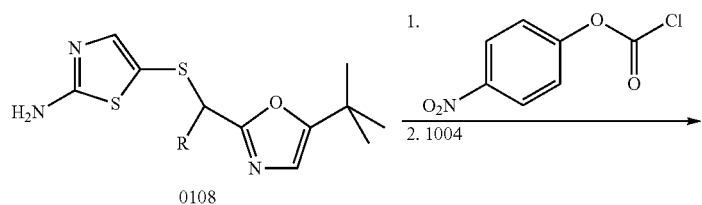
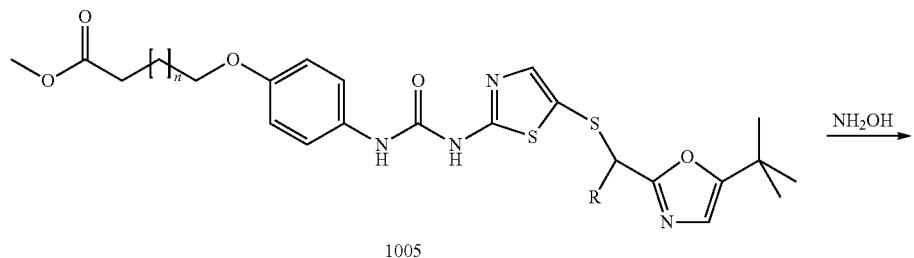
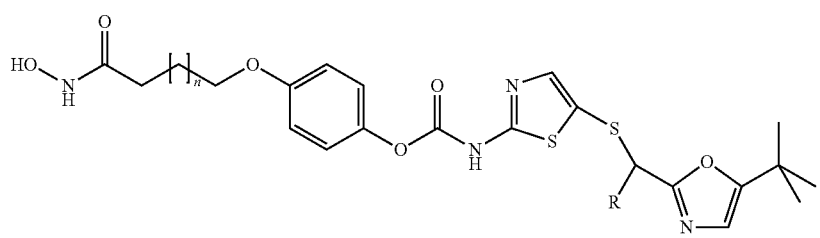
Scheme 11
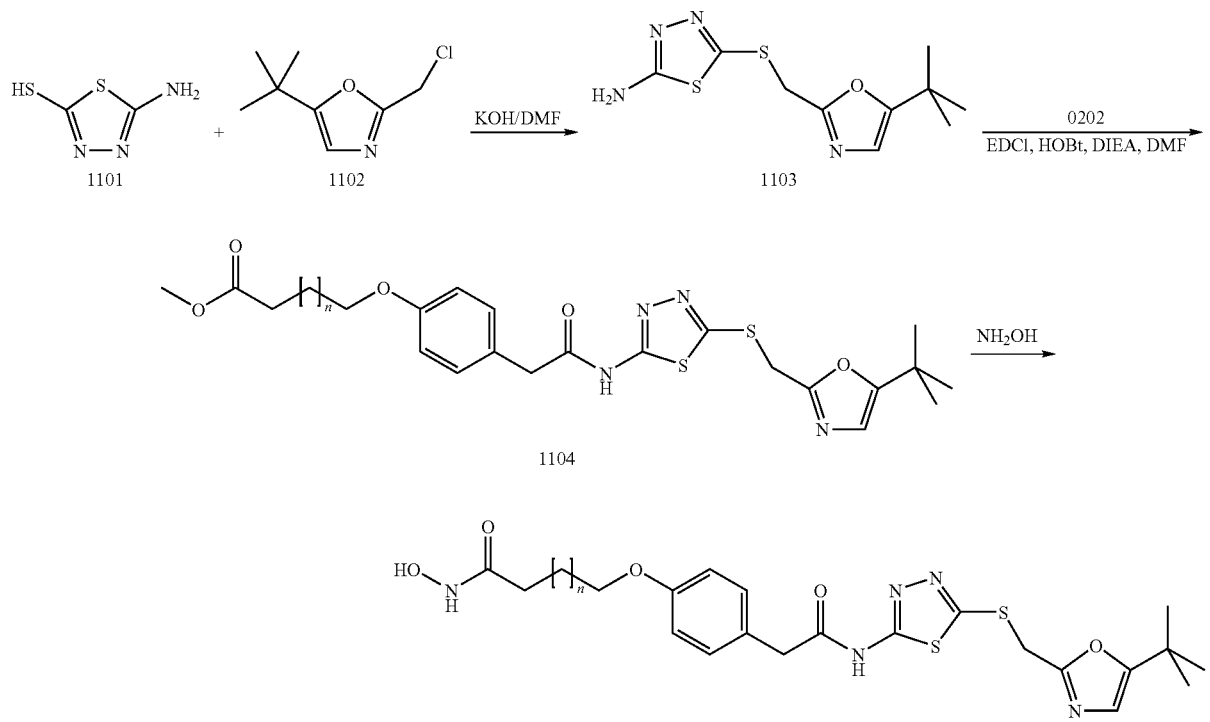

Scheme 12
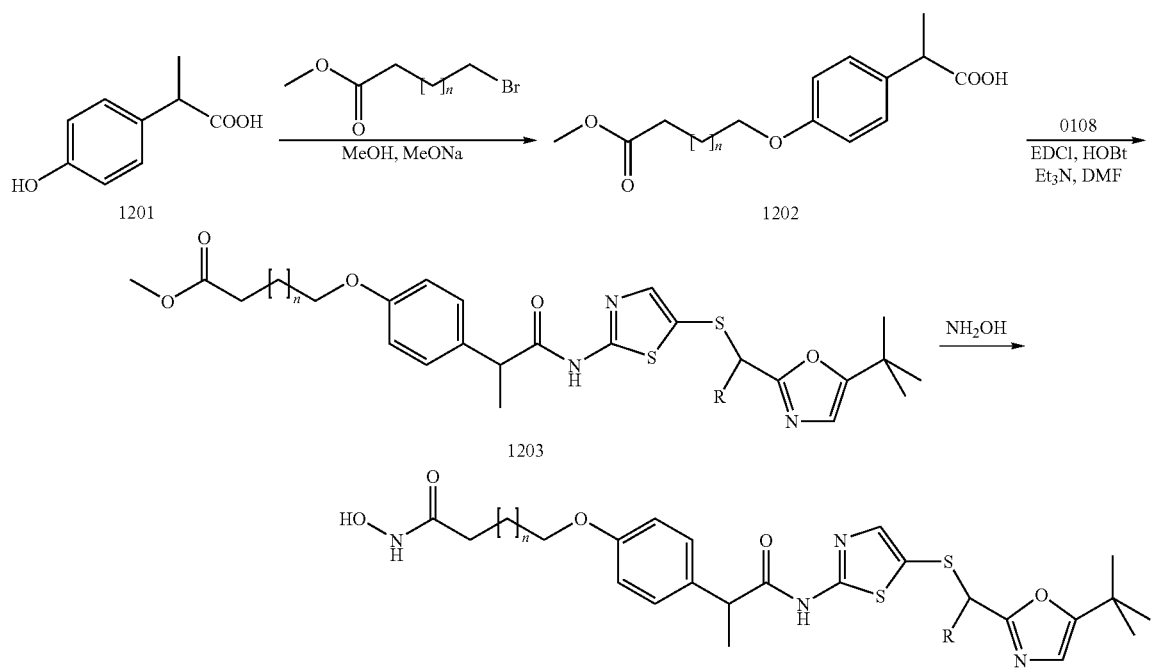
Scheme 13
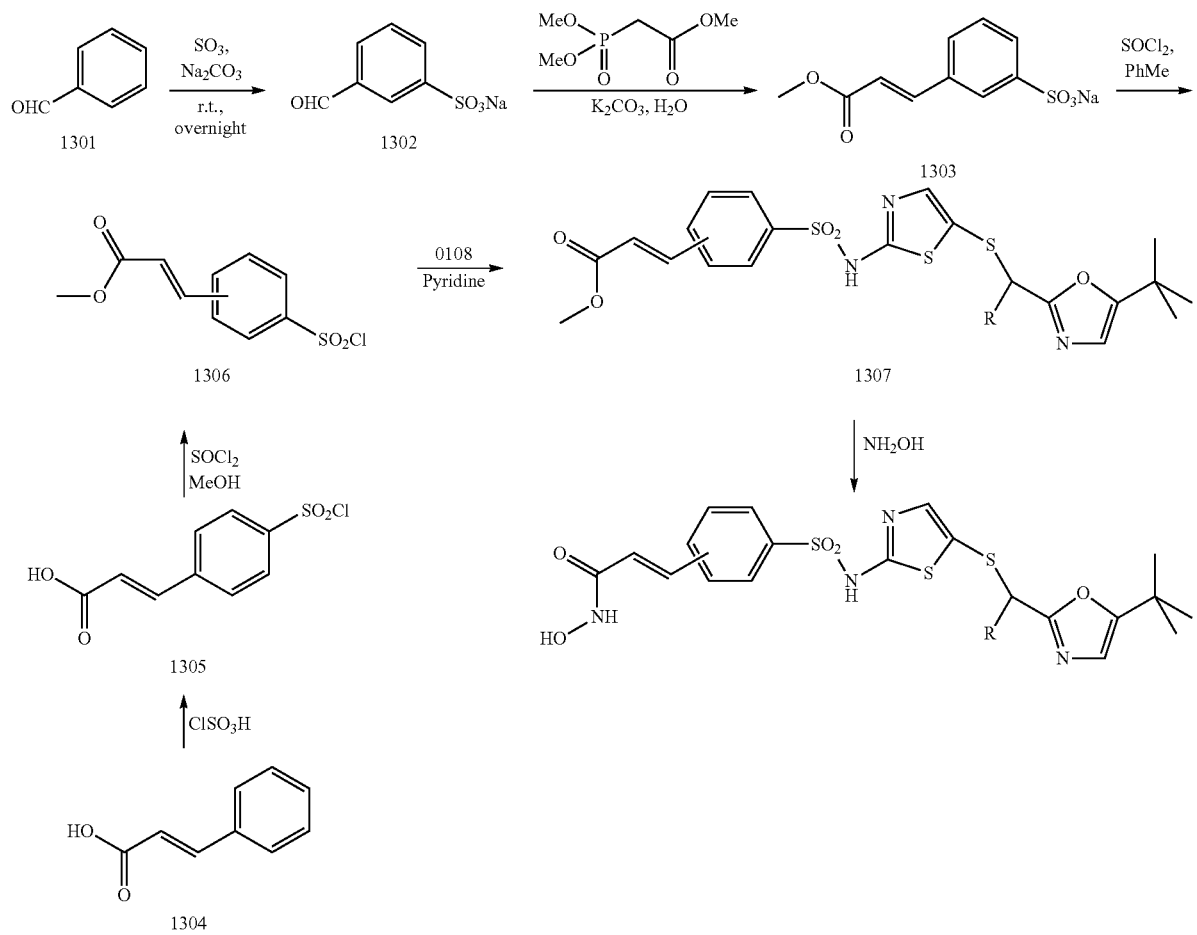

Scheme 14

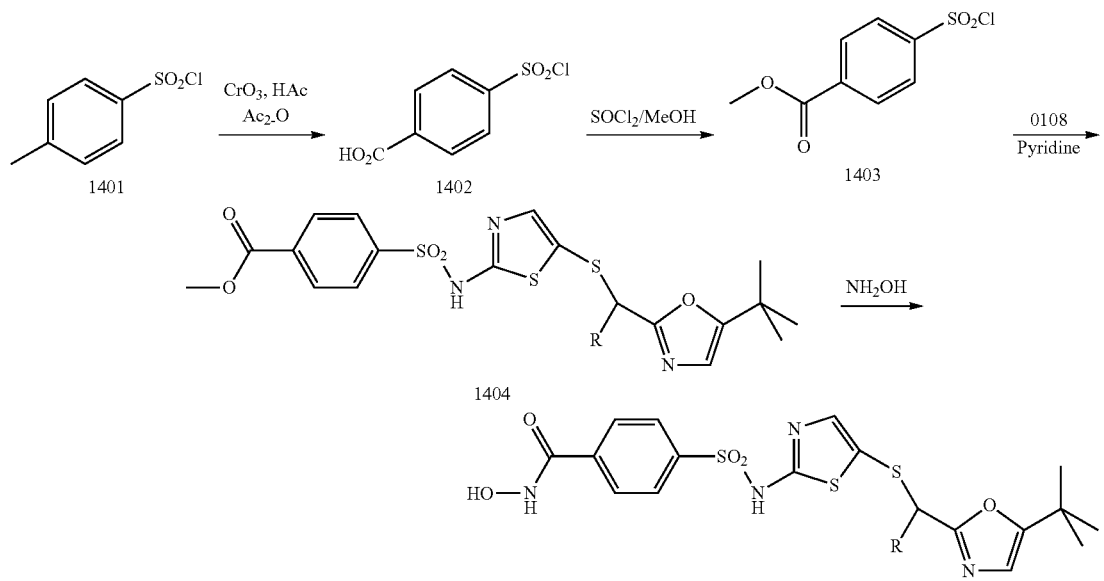

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Preparation of N-(5-((5-tert-butyloxazol-2-yl)methylthio)thiazol-2-yl)-1-(4-(hydroxyamino)-4-oxobutyl)piperidine-4-carboxamide (Compound 1)

Step 1a: α-Azidopinacolone (Compound 0102)

To a 1 L round-bottom flask fitted with a magnetic stirrer was added α-chlorpinacolone 0101 (33.5 g, 0.25 mol), acetone (400 ml), and sodium azide (21.2 g, 0.325 mol). The reaction mixture was stirred at 25° C. overnight and then filtered, and the solids were washed with acetone. The filtrate was concentrated in vacuo to provide the title compound 0102 as an oil (34.3 g, 100%). The crude material was used in the next step directly without further purification. $^1$H NMR (CDCl$_3$): δ1.17 (s, 9H), 4.07 (s, 2H).

Step 1b: α-Aminopinacolone hydrochloride (Compound 0103)

To a 2 L round-bottom flask fitted with a magnetic stirrer were added compound 0102 (34.3 g, 245 mmol), methanol (1100 ml), concentrated HCl (24 ml), and 10% Pd/C (4.2 g, wet, ~40% water). The reaction mixture was stirred under hydrogen atmosphere overnight. The mixture was filtered through a pad of Celite, and rinsed with methanol. The filtrate was concentrated under reduced pressure at a temperature below 40° C. The resulting wet solid was azeotroped with i-propanol (2×100 ml), and then anhydrous ether (100 ml) was added. The mixture was stirred for 5 min. The solid product was collected by filtration, and the cake was washed with diethyl ether and dried in vacuo to give compound 0103 (28.0 g, 91%), $^1$H NMR (DMSO-d$_6$): δ 1.13 (s, 9H), 4.06 (s, 2H), 8.34 (s, 3H).

Step 1c: α-N-2 (Chloroacetylamino)pinacolone (Compound 0104)

Triethylamine (35 ml, 250 mmol) was added to a cooled solution (−5° C.) of compound 0103 in CH$_2$Cl$_2$ (350 ml). To the resulting mixture which had been cooled to −10° C. a solution of α-chloroacetyl chloride (8.8 ml, 110 mmol) in CH$_2$Cl$_2$ (20 ml) was added dropwise over 15 min while keeping the reaction temperature below −5° C. The reaction mixture was stirred for 1 h and quenched with 1 N HCl (200 ml). The organic phase was separated and washed with 1 N HCl (200 ml) and water (50 ml), dried (Na$_2$SO$_4$), filtered and evaporated to afford compound 0104 as a white solid (18.9 g, 98%): $^1$H NMR (CDCl$_3$): δ 1.21 (s, 9H), 4.09 (s, 2H), 4.30 (s, 2H), 7.35 (s, 1H).

Step 1d: 5-tert-Butyl-2-chloromethyloxazole (Compound 0105)

To a 100 ml round-bottom flask fitted with a magnetic stirrer were added compound 0104 (9.534 g, 49.9 mmol) and POCl$_3$ (30 ml). The reaction mixture was heated to 105° C. and stirred for 1 h. After being cooled to room temperature, the reaction mixture was poured carefully into ice. The mixture was extracted with ether for six times. The organic extracts were combined and neutralized to pH 7-8 with saturated sodium bicarbonate. The organic phase was separated and washed successively with saturated sodium bicarbonate, water, and brine, dried (MgSO4), and concentrated in vacuo. The crude material was distilled under reduced pressure to give the title compound 0105 as a colorless oil (7.756 g, 70%): bp. 49° C./0.25 mmHg. $^1$H NMR (CDCl$_3$): δ 1.32 (s, 9H), 4.60 (s, 2H), 6.70 (s, 1H).

Step 1e: 5-Thiocyanatothiazol-2-amine (Compound 0107)

A mixture of 2-amino-5-bromothiazole hydrobromide 0106 (53.0 g, 0.204 mol) and potassium thiocyanate (78.5 g, 0.808 mol) in methanol (1.4 L) was stirred at room temperature for 20 h. Methanol was evaporated. The residue was added water (180 ml) and adjusted the pH of the solution to pH=12 with 10% NaOH. The resulting solid was filtered to give the title product 0107 as a brown solid (14.0 g, 44%): LCMS: 157 [M+1]$^+$.

Step 1f: 5-((5-Tert-butyloxazol-2-yl)methylthio)thiazol-2-amine (Compound 0108)

To a solution of compound 0107 (3.14 g, 20 mmol) in absolute EtOH (200 ml) was added NaBH$_4$ (1.6 g, 40 mmol) portionwise at room temperature. The mixture was stirred for 1 h, and then acetone (100 ml) was slowly introduced. After 1 h, a solution of compound 0105 (3.5 g, 20 mmol) in EtOH (30 ml) was added, and the resulting dark reaction mixture heated to reflux for 1 h. The resulting mixture was cooled, concentrated in vacuo, and then partitioned between EtOAc and brine. The organic phase was separated, dried (MgSO4), and concentrated in vacuo to give a crude solid. The crude material was triturated with diethyl ether/hexane to provide compound 0108 as a pale red-brown solid (3.1 g, 57%): LCMS: 270 [M+1]$^+$.

Step 1g: Tert-butyl 4-(5-((5-tert-butyloxazol-2-yl)methylthio)thiazol-2-yl-carbamoyl)piperidine-1-carboxylate (Compound 0109)

To a solution of compound 0108 (750 mg, 2.79 mmol), 1-(tert-butoxycarbonyl)piperidine-4-carboxylic acid (960 mg, 4.18 mmol), DMAP (510 mg, 4.18 mmol) in DMF were added EDAC (802 mg, 4.18 mmol) and HOBt (560 mg, 4.18 mmol). The mixture was heated to 50° C. and stirred overnight. The mixture was diluted with EtOAc and washed with brine, aqueous HCl, saturate NaHCO$_3$ and brine. The organic phase was dried over Na$_2$SO$_4$ and purified by column chromatography on silica gel (ethyl acetate/petroleum ether=1:2 to pure ethyl acetate) to afford the title compound 0109 (1.0 g, 74.6%): LCMS: 481 [M+1]$^+$.

Step 1h: N-(5-((5-Tert-butyloxazol-2-yl)methylthio)thiazol-2-yl)piperidine-4-carboxamide (Compound 0110)

To a mixture of compound 0109 (1.0 g, 2 mmol) in dichloromethane (20 ml) was added TFA (2 ml). The reaction mixture was stirred at 30° C. for 3 h. After reaction the mixture was brought to pH 7-8 with saturate NaHCO$_3$ and exacted with ethyl acetate. The organic phase was dried over Na$_2$SO$_4$, concentrated to give the title compound 0110 (620 mg, 82%): mp 178.5-180° C., LCMS: 381 [M+1]$^+$, $^1$H NMR (CDCl$_3$): δ 1.164 (s, 9H), 1.720-1.795 (m, 2H), 1.923-1.969 (m, 2H), 2.714-2.777 (m, 1H), 2.889 (t, J=12 Hz, 2H), 3.281 (s, 1H), 4.046 (s, 1H), 6.708 (s, 1H), 7.393 (s, 1H), 8.844 (m, 1H).

Step 1i: Ethyl 4-(4-(5-((5-tert-butyloxazol-2-yl)methylthio)thiazol-2-ylcarbamoyl)piperidin-1-yl)butanoate (Compound 0111-1)

To a solution of 0110 (300 mg, 0.789 mmol) in DMF (10 ml) was added ethyl 4-bromobutanoate (153 mg, 0.789 mmol). The reaction mixture was stirred at room temperature for 30 min. K$_2$CO$_3$ (108 mg, 0.789 mmol) was added to the mixture and the resulting mixture was stirred at room temperature overnight. The mixture was washed with water and extracted with CH$_2$Cl$_2$. The organic phase was dried over Na$_2$SO$_4$, concentrated to give the crude product. The crude product was purified by column chromatography on silica gel (ethyl acetate/petroleum ether=1:1 to 100% ethyl acetate) to give the title compound 0111 (180 mg, 46%), LCMS: 496 [M+1]$^+$.

Step 1j: N-(5-((5-Tert-butyloxazol-2-yl)methylthio)thiazol-2-yl)-1-(4-(hydroxylamino)-4-oxobutyl)piperidine-4-carboxamide (Compound 1)

The freshly prepared hydroxylamine solution (2.1 ml, 3.6 mmol) was placed in 10 ml flask. Compound 0111 (180 mg, 0.36 mmol) was added to this solution and stirred at 25° C. for 4 hours. The mixture was neutralized with acetic acid, and the methanol was removed. The residue was purified by preparing HPLC to give the title compound 1 as a white solid (25 mg, 14%): mp 176-180° C., LCMS: 482 [M+1]$^+$, $^1$H NMR (DMSO-d$_6$): δ 1.149 (s, 9H), 1.352 (m, 2H), 1.720-2.320 (m, 10H), 2.403 (m, 1H), 2.570 (m, 2H), 4.032 (s, 2H), 6.696 (s, 1H), 7.350 (s, 1H), 8.747 (s, 1H), 10.440 (s, 1H), 12.326 (s, 1H).

Example 2

Preparation of N-(5-((5-tert-butyloxazol-2-yl)methylthio)thiazol-2-yl)-1-(5-(hydroxyamino)-5-oxopentyl)piperidine-4-carboxamide (Compound 2)

Step 2a: Methyl 5-(4-(5-((5-tert-butyloxazol-2-yl)methylthio)thiazol-2-ylcarbamoyl)piperidin-1-yl)pentanoate (Compound 0111-2)

The title compound 0111-2 was prepared as a yellow solid (126 mg, 38.7%) from compound 0110 (250 mg, 0.658 mmol), methyl 5-bromopentanoate (128 mg, 0.658 mmol), K$_2$CO$_3$ (90.8 mg, 0.658 mmol), and DMF (5 ml) using a procedure similar to that described for compound 0111-1 (Example 1): LCMS: 495 [M+1]$^+$.

Step 2b: N-(5-((5-tert-butyloxazol-2-yl)methylthio)thiazol-2-yl)-1-(5-(hydroxylamino)-5-oxopentyl)piperidine-4-carboxamide (compound 2)

The title compound 2 was prepared as a yellow solid (20 mg, 15.8%) from compound 0111-2 (126 mg, 0.255 mmol) and freshly prepared hydroxylamine solution (1.5 ml, 2.55 mmol) using a procedure similar to that described for compound 1 (Example 1): M.p.: 93-97° C.; LCMS: 496 [M+1]$^+$. $^1$H NMR (DMSO-d$_6$): δ 1.148 (s, 9H), 1.353-1.949 (m, 10H), 2.187-2.227 (m, 2H), 2.408 (m, 1H), 2.837 (d, J=11.1, 2H), 4.026 (s, 2H), 6.696 (s, 1H), 7.355 (s, 1H), 8.647 (s, 1H), 10.314 (s, 1H), 12.190 (s, 1H).

Example 3

Preparation of N-(5-((5-tert-butyloxazol-2-yl)methylthio)thiazol-2-yl)-1-(6-(hydroxyamino)-6-oxohexyl)piperidine-4-carboxamide (Compound 3)

Step 3a: Ethyl 6-(4-(5-((5-tert-butyloxazol-2-yl)methylthio)thiazol-2-yl-carbamoyl)piperidin-1-yl)hexanoate (Compound 0111-3)

The title compound 0111-3 was prepared as a yellow solid (210 mg, 51%) from compound 0110 (300 mg, 0.789 mmol), ethyl 6-bromohexanoate (176 mg, 0.789 mmol), K$_2$CO$_3$ (108 mg, 0.789 mmol) and DMF (5 ml) using a procedure similar to that described for compound 0111-1 (Example 1): LCMS: 523 [M+1]$^+$.

Step 3b: N-(5-((5-Tert-butyloxazol-2-yl)methylthio) thiazol-2-yl)-1-(6-(hydroxyamino)-6-oxohexyl)piperidine-4-carboxamide (Compound 3)

The title compound 3 was prepared as a yellow solid (30 mg, 15.8%) from compound 0111-3 (210 mg, 0.40 mmol) and freshly prepared hydroxylamine solution (2.5 ml, 4.0 mmol) using a procedure similar to that described for compound 1 (Example 1): M.p.: 127-130° C.; LCMS: 510 [M+1]$^+$. $^1$H NMR (DMSO-d$_6$): δ 1.158 (s, 9H), 1.218-1.927 (m, 14H), 2.204-2.254 (m, 2H), 2.402 (m, 1H), 2.619 (m, 2H), 4.033 (s, 2H), 6.698 (s, 1H), 7.377 (s, 1H), 8.669 (s, 1H), 10.345 (s, 1H), 12.354 (s, 1H).

Example 4

Preparation of N-(5-((5-tert-butyloxazol-2-yl)methylthio)thiazol-2-yl)-1-(7-(hydroxyamino)-7-oxoheptyl)piperidine-4-carboxamide (Compound 4)

Step 4a: Ethyl 7-(4-(5-((5-tert-butyloxazol-2-yl)methylthio)thiazol-2-ylcarbamoyl)piperidin-1-yl)heptanoate (Compound 0111-4)

The title compound 0111-4 was prepared as a yellow solid (370 mg, 62%) from compound 0110 (423 mg, 1.113 mmol), ethyl 7-bromoheptanoate (260 mg, 1.113 mmol), K$_2$CO$_3$ (154 mg, 1.113 mmol) and DMF (5 ml) using a procedure similar to that described for compound 0111-1 (Example 1): LCMS: 537 [M+1]$^+$.

Step 4b: N-(5-((5-tert-butyloxazol-2-yl)methylthio) thiazol-2-yl)-1-(7-(hydroxylamino)-7-oxoheptyl) piperidine-4-carboxamide (compound 4)

The title compound 4 was prepared as a yellow solid (20 mg, 6%) from compound 0111-4 (370 mg, 0.69 mmol) and freshly prepared hydroxylamine solution (4.0 ml, 6.9 mmol) using a procedure similar to that described for compound 1 (Example 1): M.p.: 113-115° C.; LCMS: 524 [M+1]$^+$; $^1$H NMR (DMSO-d$_6$): δ 1.153 (s, 9H), 1.215-1.483 (m, 4H), 1.545-1.628 (m, 4H), 1.708-1.892 (m, 6H), 1.917-2.224 (m, 4H), 2.425 (m, 1H), 2.844-2.882 (m, 2H), 4.031 (s, 2H), 6.701 (s, 1H), 7.361 (s, 1H), 8.655 (s, 1H), 10.361 (s, 1H), 12.216 (s, 1H).

Example 5

Preparation of 4-(4-(2-(5-((5-tert-butyloxazol-2-yl) methylthio) thiazol-2-ylamino)-2-oxoethyl)phenoxy)-N-hydroxybutanamide (Compound 9)

Step 5a: 2-(4-(4-Methoxy-4-oxobutoxy)phenyl)acetic acid (Compound 0202-9)

To the solution of MeONa (1.08 g, 20 mmol) in MeOH (20 ml) was added compound 0201 (1.52 g, 10 mmol) at 0° C. under nitrogen. The mixture was stirred for 10 minutes and ethyl 4-bromobutanoate (1.94 g, 10 mmol) was added. After stirred at 50° C. overnight, the mixture was adjusted PH 6-7 with acetic acid, and concentrated. The residue was taken up in ethyl acetate, washed with water, brine, dried and concentrated to give a residue which was purified by column chromatography (eluent: ethyl acetate/petroleum ether 1/5) to afford the product 0202-9 as a solid (841 mg, 33%): $^1$H NMR (DMSO-d$_6$): δ 12.24 (s, 1H), 7.15 (d, J=8.7 Hz, 2H), 6.85 (d, J=8.7 Hz, 2H), 3.95 (t, J=6.3 Hz, 2H), 3.59 (s, 3H), 3.47 (s, 2H), 2.49 (m, 2H), 1.95 (m, 2H).

Step 5b: Methyl-4-(4-(2-(5-((5-tert-butyloxazol-2-yl) methylthio)thiazol-2-ylamino)-2-oxoethyl)phenoxy) butanoate (Compound 0203-9)

The solution of 0202-9 (0.189 g, 0.75 mmol), 0108 (0.135 g, 0.5 mmol), EDCI (0.143 g, 0.75 mmol), DMAP (0.092 g, 0.75 mmol), HOBt (0.101 g, 0.75 mmol) in DMF (5 ml) was stirred at 40° C. for 4 hours, After that, the mixture was poured into ethyl acetate (50 ml), and washed with water and brine, dried and concentrated to give a residue which was purified by column chromatography (eluent: ethyl acetate/petroleum ether=1/3) to afford the product 0203-9 as a solid (40 mg, 16%): $^1$H NMR (DMSO-d$_6$): δ 12.43 (s, 1H), 7.39 (s, 1H), 7.19 (d, J=8.7 Hz, 2H), 6.86 (d, J=8.7 Hz, 2H), 6.69 (s, 1H), 4.04 (s, 2H), 3.95 (t, J=6.3 Hz, 2H), 3.65 (s, 2H), 3.59 (s, 3H), 2.50 (t, J=3.3 Hz, 2H), 1.95 (m, 2H), 1.13 (s, 9H).

Step 5c: 4-(4-(2-(5-((5-Tert-butyloxazol-2-yl)methylthio)thiazol-2-yl-amino)-2-oxoethyl)phenoxy)-N-hydroxybutanamide (Compound 9)

Preparation of hydroxylamine in methanol solution: hydroxylamine hydrochloride (4.67 g, 67 mmol) was dissolved in methanol (24 mL) to form solution A. Potassium hydroxide (5.61 g, 100 mmol) was dissolved in methanol (14 mL) to form solution B. To the solution A at 0° C. was added solution B dropwise. The mixture was stirred for 30 minutes at 0° C., and the solid was filtered to afford a solution of hydroxylamine in methanol.

To a flask containing compound 0203-9 (40 mg, 0.080 mmol) was added the solution of hydroxylamine in methanol (6.0 mL). The mixture was stirred at room temperature for 1 hour. Then it was adjusted PH 7 with concentrated HCl. The mixture was concentrated to give a residue which was washed with water to afford the product 9 as a solid (18 mg, 44% yield). $^1$H NMR (DMSO-d$_6$): δ 12.43 (s, 1H), 10.391 (s, 1H), 8.68 (s, 1H), 7.36 (s, 1H), 7.18 (d, J=8.7 Hz, 2H), 6.84 (d, J=8.7 Hz, 2H), 6.67 (s, 1H), 4.01 (s, 2H), 3.90 (t, J=6 Hz, 2H), 3.63 (s, 2H), 2.11 (t, J=7.2 Hz, 2H), 1.19 (m, 2H), 1.12 (s, 9H).

Example 6

Preparation of 5-(4-(2-(5-((5-tert-butyloxazol-2-yl) methylthio) thiazol-2-ylamino)-2-oxoethyl)phenoxy)-N-hydroxypentanamide (Compound 10)

Step 6a: 2-(4-(5-Methoxy-5-oxopentyloxy)phenyl) acetic acid (Compound 0202-10)

The title compound 0202-10 was prepared as a yellow solid (322 mg, 24%) from compound 0201 (0.76 g, 5 mmol), and methyl 5-bromopentanoate (0.98 g, 5 mmol) using a procedure similar to that described for compound 0202-9 (Example 5): $^1$H NMR (DMSO-d$_6$): δ 12.24 (s, 1H), 7.15 (d, J=8.7 Hz, 2H), 6.91 (d, J=8.7 Hz, 2H), 3.94 (t, J=6.0 Hz, 2H), 3.59 (s, 3H), 3.48 (s, 2H), 2.38 (t, J=7.2 Hz, 2H), 1.69 (m, 4H).

Step 6b: Methyl-5-(4-(2-(5-((5-tert-butyloxazol-2-yl) methylthio)-thiazol-2-ylamino)-2-oxoethyl)phenoxy) pentanoate (compound 0203-10)

The solution of 0202-10 (0.193 g, 0.75 mmol), 0108 (0.135 g, 0.5 mmol), EDCI (0.143 g, 0.75 mmol), DMAP (0.092 g, 0.75 mmol), HOBt (0.101 g, 0.75 mmol) in DMF (5 ml) was stirred at 40° C. for 4 hours, After that, the mixture was poured into ethyl acetate (50 ml), and washed with water and brine, dried and concentrated to give a residue which was purified by column chromatography (ethyl acetate/petroleum ether=1/3) to afford the product 0203-10 as a solid (45 mg, 12%). $^1$H NMR (DMSO-d$_6$): δ 12.45 (s, 1H), 7.39 (s, 2H), 7.20 (d, J=9.0 Hz, 2H), 6.87 (d, J=9.0 Hz, 2H), 6.70 (s, 1H), 4.04 (s, 2H), 3.93 (t, J=6.3 Hz, 2H), 3.65 (s, 2H), 3.58 (s, 3H), 2.37 (t, J=6.0 Hz, 2H), 1.69 (m, 4H), 1.137 (s, 9H).

Step 6c: 5-(4-(2-(5-(((5-Tert-butyloxazol-2-yl)methylthio)thiazol-2-yl-amino)-2-oxoethyl)phenoxy)-N-hydroxypentanamide (Compound 10)

The title compound 10 was prepared as a yellow solid (17 mg, 38% yield) from compound 0203-10 (45 mg, 0.087 mmol) and freshly prepared solution of hydroxylamine in methanol (6.0 mL) using a procedure similar to that described for compound 9 (Example 5): $^1$H NMR (DMSO-d$_6$): δ 12.43 (s, 1H), 10.36 (s, 1H), 8.69 (s, 1H), 7.38 (s, 1H), 7.20 (d, J=9.0 Hz, 2H), 6.86 (d, J=9.0 Hz, 2H), 6.69 (s, 2H), 4.04 (s, 2H), 3.92 (t, J=6.0 Hz, 2H), 1.99 (t, J=6.0 Hz, 2H), 1.64 (m, 4H), 1.14 (s, 9H).

Example 7

Preparation of methyl 6-(4-(2-(5-(((5-tert-butyloxazol-2-yl)methyl thio)thiazol-2-ylamino)-2-oxoethyl)phenoxy)hexanoate (Compound 11)

Step 7a: 2-(4-(6-Methoxy-6-oxohexyloxy)phenyl) acetic acid (compound 0202-11)

The title compound 0202-11 was prepared as a yellow solid (950 mg, 34%) from compound 0201 (0.76 g, 5 mmol), and methyl 5-bromopentanoate (2.22 g, 10 mmol) using a procedure similar to that described for compound 0202-9 (Example 5): $^1$H NMR (DMSO-d$_6$): δ 12.22 (s, 1H), 7.14 (d, J=8.4 Hz, 2H), 6.85 (d, J=8.4 Hz, 2H), 3.92 (t, J=6.3 Hz, 2H), 3.58 (s, 3H), 3.47 (s, 2H), 2.32 (t, J=7.5 Hz, 2H), 1.69 (m, 2H), 1.55 (m, 2H), 1.40 (m, 2H).

Step 7b: Methyl 6-(4-(2-(5-(((5-tert-butyloxazol-2-yl) methylthio)-thiazol-2-ylamino)-2-oxoethyl)phenoxy) hexanoate (Compound 0203-11)

The title compound 0203-11 was prepared as a yellow solid (63 mg, 16%) from compound 0202-9 using a procedure similar to that described for compound 0203-9 (Example 5): $^1$H NMR (DMSO-d$_6$): δ 12.43 (s, 1H), 7.37 (s, 1H), 7.18 (d, J=8.7 Hz, 2H), 6.83 (d, J=8.7 Hz, 2H), 6.67 (s, 1H), 4.02 (s, 2H), 3.89 (t, J=6.3 Hz, 2H), 3.63 (s, 2H), 3.55 (s, 3H), 2.30 (t, J=7.2 Hz, 2H), 1.67 (m, 2H), 1.55 (m, 2H), 1.37 (m, 2H), 1.11 (s, 9H).

Step 7c: Methyl 6-(4-(2-(5-(((5-tert-butyloxazol-2-yl) methylthio)-thiazol-2-ylamino)-2-oxoethyl)phenoxy) hexanoate (Compound 11)

The title compound 11 was prepared as a yellow solid (82 mg, 42% yield) from compound 0203-11 (193 mg, 0.363 mmol) and freshly prepared solution of hydroxylamine in methanol (6.0 mL) using a procedure similar to that described for compound 9 (Example 5): $^1$H NMR (DMSO-d$_6$): δ 12.46 (s, 1H), 10.35 (s, 1H), 8.68 (s, 1H), 7.39 (s, 1H), 7.18 (d, J=8.4 Hz, 2H), 6.85 (d, J=8.4 Hz, 2H), 6.70 (s, 1H), 4.04 (s, 2H), 3.92 (t, J=6.3 Hz, 2H), 3.65 (s, 3H), 1.96 (t, J=6.3 Hz, 2H), 1.69 (m, 2H), 1.54 (m, 2H), 1.37 (m, 2H), 1.143 (s, 9H).

Example 8

Preparation of N-hydroxy-7-(4-(2-(5-((5-isopropyloxazol-2-yl)methylthio)thiazol-2-ylamino)-2-oxoethyl)phenoxy)heptanamide (Compound 12)

Step 8a: 2-(4-(7-Methoxy-7-oxoheptyloxy)phenyl) acetic acid (Compound 0202-12)

The title compound 0202-12 was prepared as a yellow solid (219 mg, 15%) from compound 0201 using a procedure similar to that described for compound 0202-9 (Example 5): $^1$H NMR (DMSO-d$_6$): δ 12.22 (s, 1H), 7.14 (d, J=8.1 Hz, 2H), 6.84 (d, J=8.1 Hz, 2H), 3.89 (t, J=6.3 Hz, 2H), 3.55 (s, 3H), 3.44 (s, 2H), 2.30 (t, J=7.2 Hz, 2H), 1.68 (m, 2H), 1.54 (m, 2H), 1.35 (m, 4H).

Step 8b: Methyl 7-(4-(2-(5-(((5-tert-butyloxazol-2-yl) methylthio)-thiazol-2-ylamino)-2-oxoethyl)phenoxy) heptanoate (Compound 0203-12)

The title compound 0203-12 was prepared as a yellow solid (100 mg, 26%) from compound 0202-12 using a procedure similar to that described for compound 0203-9 (Example 5): $^1$H NMR (DMSO-d$_6$): δ 12.45 (s, 1H), 7.39 (s, 1H), 7.20 (d, J=8.4 Hz, 2H), 6.86 (d, J=8.4 Hz, 2H), 6.69 (s, 1H), 4.04 (s, 2H), 3.91 (t, J=6.3 Hz, 2H), 3.65 (s, 2H), 3.57 (s, 3H), 2.30 (t, J=7.2 Hz, 2H), 1.65 (m, 2H), 1.51 (m, 2H), 1.34 (m, 4H), 1.13 (s, 9H).

Step 8c: N-Hydroxy-7-(4-(2-(5-(((5-isopropyloxazol-2-yl)methylthio)-thiazol-2-ylamino)-2-oxo-ethyl) phenoxy)heptanamide (Compound 12)

The title compound 12 was prepared as a solid (65 mg, 68% yield) from compound 0203-12 (95 mg, 0.174 mmol) and freshly prepared solution of hydroxylamine in methanol (10.0 mL) using a procedure similar to that described for compound 9 (Example 5): $^1$H NMR (DMSO-d$_6$): δ 12.45 (s, 1H), 10.33 (s, 1H), 8.66 (s, 1H), 7.39 (s, 1H), 7.20 (d, J=8.4 Hz, 2H), 6.87 (d, J=8.4 Hz, 2H), 6.69 (s, 1H), 4.04 (s, 2H), 3.91 (t, J=6.3 Hz, 2H), 3.65 (s, 2H), 3.57 (s, 3H), 2.30 (t, J=7.2 Hz, 2H), 1.65 (m, 2H), 1.53 (m, 2H), 1.34 (m, 4H), 1.13 (s, 9H).

Example 9

Preparation of N$^1$-(5-((5-tert-butyloxazol-2-yl)methylthio)thiazol-2-yl)-N$^5$-hydroxyglutaramide (Compound 5)

Step 9a: Methyl 5-(5-((5-tert-butyloxazol-2-yl)methylthio)thiazol-2-ylamino)-5-oxo-pentanoate (Compound 0301-5)

To a mixture of compound 0108 (269 mg, 1.0 mmol), EDCI (230 mg, 1.2 mmol) and DMAP (147 mg, 1.2 mmol in dimethylformamide (5.0 mL) was added 5-methoxy-5-oxopentanoic acid (175 mg, 1.2 mmol) and the mixture was stirred at room temperature for 12 h. The reaction was quenched with 1 M HCl (20 mL) and was extracted with ethyl acetate (30 mL×4), dried and concentrated to afford the crude product 0301-5 as a pale yellow solid (216 mg, 54.4% yield). LC-MS: 398 (M+1).

Step 9b: N$^1$-(5-((5-tert-butyloxazol-2-yl)methylthio) thiazol-2-yl)-N$^5$-hydroxyl-glutaramide (Compound 5)

The title compound 5 was prepared as a solid (80 mg, 44.6% yield) from compound 0301-5 (180 mg, 0.45 mmol) and freshly prepared solution of hydroxylamine in methanol (2 mL) using a procedure similar to that described for compound 9 (Example 5). $^1$H NMR (DMSO-d$_6$) δ12.28 (s, 1H), 10.39 (s, 1H), 8.72 (s, 1H), 7.37 (s, 1H), 6.72 (s, 1H), 4.06 (m, 2H), 2.43 (t, J=7.8 Hz, 2H), 2.00 (t, J=7.8 Hz, 2H), 1.76-1.83 (q, 2H), 1.19 (s, 9H). LC-MS: 399 (M+1).

Example 10

Preparation of N$^1$-(5-((5-tert-butyloxazol-2-yl)methylthio)-thiazol-2-yl)-N$^6$-hydroxyadipamide (Compound 6)

Step 10a: Methyl 6-(5-((5-tert-butyloxazol-2-yl)methylthio)thiazol-2-ylamino)-6-oxohexanoate (Compound 0301-6)

The title compound was prepared as a pale yellow solid (273 mg, 66.3%) from 0108 (269 mg, 1.0 mmol) and 6-methoxy-6-oxohexanoic acid (175 mg, 1.2 mmol) using a procedure similar to that described for 0301-5 (Example 9): LC-MS: 412 (M+1).

Step 10b: N$^1$-(5-((5-tert-butyloxazol-2-yl)methylthio)thiazol-2-yl)-N$^6$-hydroxy-adipamide (Compound 6)

The title compound 6 was prepared as a solid (37 mg, 19% yield) from compound 0301-6 (200 mg, 0.48 mmol) and freshly prepared solution of hydroxylamine in methanol (2 mL) using a procedure similar to that described for compound 9 (Example 5). $^1$H NMR (DMSO-d$_6$) δ12.23 (s, 1H), 10.36 (s, 1H), 8.68 (s, 1H), 7.37 (s, 1H), 6.71 (s, 1H), 4.05 (s, 2H), 2.38-2.51 (m, 2H), 1.93-1.99 (q, 2H), 1.48-1.52 (q, 4H), 1.19 (s, 9H). LC-MS: 413 (M+1).

Example 11

Preparation of N$^1$-(5-((5-tert-butyloxazol-2-yl)methylthio)thiazol-2-yl)-N$^8$-hydroxyoctanediamide (Compound 8)

Step 11a: Methyl 8-(5-((5-tert-butyloxazol-2-yl)methylthio)thiazol-2-ylamino)-8-oxooctanoate (Compound 0301-8)

The title compound was prepared as a pale yellow solid (199 mg, 45.2%) from 0108 (269 mg, 1.0 mmol) and 8-methoxy-8-oxooctanoic acid (226 mg, 1.2 mmol) using a procedure similar to that described for 0301-5 (Example 9): LC-MS: 440 (M+1).

Step 11b: N$^1$-(5-((5-tert-butyloxazol-2-yl)methylthio)thiazol-2-yl)-N$^8$-hydroxyoctanediamide (Compound 8)

The title compound 8 was prepared as a solid (100 mg, 57% yield) from compound 0301-8 (175 mg, 0.40 mmol) and freshly prepared solution of hydroxylamine in methanol (2 mL) using a procedure similar to that described for compound 9 (Example 5). $^1$H NMR (DMSO-d$_6$) δ 12.24 (s, 1H), 10.35 (s, 1H), 8.67 (s, 1H), 7.37 (s, 1H), 6.71 (s, 1H), 4.05 (s, 2H), 2.39 (t, J=7.5 Hz, 2H), 1.93 (t, J=7.2 Hz, 2H), 1.44-1.57 (m, 4H), 1.22-1.23 (m, 4H), 1.17 (s, 9H). LC-MS: 441 (M+1).

Example 12

Preparation of N-(5-((5-tert-butyloxazol-2-yl)methylthio)thiazol-2-yl)-4-(3-(hydroxyamino)-3-oxopropylamino)butanamide (Compound 13)

Step 12a: 4-Bromo-N-(5-((5-tert-butyloxazol-2-yl)methylthio)thiazol-2-yl)-butanamide (Compound 0401-13)

To a stirred mixture of compound 0108 (13.5 g, 0.05 mol) and pyridine (5 g) in dimethylformamide (100 ml) was added a solution of 4-bromobutanoyl chloride (14 g, 0.075 mol) in acetone (25 ml) over a period of 2-3 min, while maintaining at 0-5° C. The resulting mixture was allowed to warm to r.t. and stirred for additional 1 h. To the mixture 1 M HCl (20 mL) was added to quench the reaction and the mixture was extracted with ethyl acetate (30 mL×4), dried and concentrated to afford the crude product compound 0401-13 as a yellow solid (15 g, 72% yield). $^1$H NMR (DMSO-d$_6$) δ 12.30 (s, 1H), 7.38 (s, 1H), 6.71 (s, 1H), 4.05 (s, 2H), 3.56 (t, J=6.6 Hz, 2H), 2.58 (t, J=6.6 Hz, 2H), 2.08-2.13 (m, 2H), 1.18 (s, 9H). LC-MS: 419 (M+1).

Step 12b: 4-Azido-N-(5-((5-tert-butyloxazol-2-yl)methylthio)thiazol-2-yl)butanamide (Compound 0402-13)

To a clear solution of 0401-13 (20 g, 0.048 mol) in DMF (40 ml) was added a solution of NaN$_3$ (4.0 g, 0.062 mol) in DMF (10 ml) slowly at room temperature. The reaction mixture was stirred at room temperature for 12 h and concentrated to remove DMF in vacuuo to afford the crude product which was used to next step reaction without further purification. LC-MS: 380.95 (M+1).

Step 12c: 4-Amino-N-(5-((5-tert-butyloxazol-2-yl)methylthio)thiazol-2-yl)-butanamide (Compound 0403-13)

A mixture of 0403-13 (16 g, 0.042 mol), PPh$_3$ (12.4 g, 0.047 mol), H$_2$O (2 ml), and THF (10 ml) was stirred at room temperature for 6 h. The mixture was concentrated under reduced pressure to afford the crude product which was purified by a flash column on silica gel (methanol:dichloromethane=1:10) to afford pure product 0403-13 (10 g, 67%): $^1$H NMR (DMSO-d$_6$) δ 7.34 (s, 1H), 6.70 (s, 1H), 4.03 (s, 2H), 2.58 (t, J=7.2 Hz, 2H), 2.45 (t, J=7.2 Hz, 2H), 1.64-1.69 (m, 2H), 1.18 (s, 9H). LC-MS: 355.1 (M+1).

Step 12d: Ethyl 3-(4-(5-((5-tert-butyloxazol-2-yl)methylthio)thiazol-2-ylamino)-4-oxobutyl amino) propanoate (0404-13)

To a solution of compound 0403-13 (1.0 g, 2.82 mmol), TEA (0.43 g, 4.2 mmol) in DMF (4 ml) was added ethyl 7-bromoheptanoate in DMF (3 ml) slowly. The mixture was stirred at room temperature overnight. 1M of HCl (20 mL) was added to quench the reaction and the mixture was extracted with ethyl acetate (30 mL×4), dried and concentrated to afford the crude product, 0404-13 as a yellow solid. The crude product was purified by a flash column on silica gel (methanol:dichloromethane=1:20) to afford the pure product (300 mg, 24% yield). LC-MS: 455.2 (M+1); $^1$H NMR (DMSO-d$_6$) δ 7.34 (s, 1H), 6.68 (s, 1H), 3.98-4.05 (m, 4H), 3.14 (s, 1H), 2.69 (t, J=6.9 Hz, 2H), 2.35-2.49 (m, 6H), 1.65-1.68 (m, 2H), 1.12-1.16 (m, 12H).

Step 12e: N-(5-((5-Tert-butyloxazol-2-yl)methylthio)thiazol-2-yl)-4-(3-(hydroxylamino)-3-oxopro-pylamino)butanamide (Compound 13)

The title compound 13 was prepared as a solid (100 mg, 34% yield) from compound 0403-13 (300 mg, 0.66 mmol) and freshly prepared solution of hydroxylamine in methanol (2 mL) using a procedure similar to that described for compound 9 (Example 5). LC-MS: 442.0 (M+1); $^1$H NMR (DMSO-d$_6$) δ 7.37 (s, 1H), 6.71 (s, 1H), 4.05 (s, 2H), 2.71 (t, J=6.9 Hz, 2H), 2.12 (t, J=6.9 Hz, 2H), 1.90 (s, 2H), 1.68-1.72 (m, 2H), 1.20-1.23 (m, 2H), 1.18 (s, 9H).

Example 13

Preparation of 6-(4-(5-((5-tert-butyloxazol-2-yl)methylthio)-thiazol-2-yl amino)-4-oxobutylamino)-N-hydroxyhexanamide (Compound 16)

Step 13a: Ethyl 6-(4-(5-((5-tert-butyloxazol-2-yl)methylthio)thiazol-2-ylamino)-4-oxobutyl-amino)hexanoate (Compound 0404-16)

The title compound 0404-16 was prepared (650 mg, 30% yield) from compound 0403-13 (1.6 g, 4.5 mmol) and ethyl 6-bromohexanoate (1.5 g, 6.8 mmol) using a procedure similar to that described for compound 0404-13 (Example 12): LC-MS: 497.1 (M+1); $^1$H NMR (DMSO-d$_6$): δ 7.38 (s, 1H), 6.72 (s, 1H), 4.02-4.09 (m, 4H), 2.81-2.90 (m, 4H), 2.51-2.59 (m, 2H), 1.92-1.99 (m, 2H), 1.50-1.63 (m, 4H), 1.23-1.31 (m, 4H), 1.14-1.19 (m, 12H).

Step 13b: 6-(4-(5-((5-Tert-butyloxazol-2-yl)methylthio)thiazol-2-ylamino)-4-oxo-butylamino)-N-hydroxyhexanamide (Compound 16)

The title compound 16 was prepared as a solid (40 mg, 40% yield) from compound 0403-16 (100 mg, 0.2 mmol) and freshly prepared solution of hydroxylamine in methanol (2 mL) using a procedure similar to that described for compound 9 (Example 5). LC-MS: 484.3 (M+1); $^1$H NMR (DMSO-d$_6$) δ 10.43 (s, 1H), 9.85 (s, 1H), 7.38 (s, 1H), 6.71 (s, 1H), 4.06 (s, 2H), 2.79-2.93 (m, 6H), 1.88-1.96 (m, 4H), 1.47-1.61 (m, 4H), 1.21-1.27 (m, 2H), 1.19 (s, 9H).

Example 14

Preparation of 7-(4-(5-((5-tert-butyloxazol-2-yl)methylthio)-thiazol-2-yl amino)-4-oxobutylamino)-N-hydroxyheptanamide (Compound 17)

Step 14a: Ethyl 7-(4-(5-((5-tert-butyloxazol-2-yl)methylthio)thiazol-2-ylamino)-4-oxobutyl-amino)heptanoate (Compound 0404-17)

The title compound 0404-17 was prepared (600 mg, 21% yield) from compound 0403-13 (1.6 g, 4.5 mmol) and 7-bromoheptanoate (1.5 g, 6.8 mmol) using a procedure similar to that described for compound 0404-13 (Example 12): LC-MS: 511.1 (M+1); $^1$H NMR (DMSO-d$_6$) δ 7.36 (s, 1H), 6.71 (s, 1H), 4.00-4.07 (m, 4H), 2.43-2.54 (m, 6H), 2.23-2.28 (m, 2H), 1.99 (s, 1H), 1.68-1.73 (m, 2H), 1.38-1.53 (m, 4H), 1.22-1.29 (m, 4H), 1.14-1.17 (m, 12H).

Step 14b: 7-(4-(5-((5-Tert-butyloxazol-2-yl)methylthio)thiazol-2-ylamino)-4-oxo-butylamino)-N-hydroxyheptanamide (Compound 17)

The title compound 17 was prepared as a solid (80 mg, 84% yield) from compound 0404-17 (100 mg, 0.19 mmol) and freshly prepared solution of hydroxylamine in methanol (2 mL) using a procedure similar to that described for compound 9 (Example 5). LC-MS: 498.2 (M+1); $^1$H NMR (DMSO-d$_6$) δ 10.35 (s, 1H), 7.37 (s, 1H), 6.71 (s, 1H), 4.05 (s, 2H), 2.65-2.74 (m, 4H), 1.90-1.95 (m, 4H), 1.77-1.82 (m, 2H), 1.45-1.49 (m, 4H), 1.22-1.25 (m, 4H), 1.19 (s, 9H).

Example 15

Preparation of (E)-N-(5-((5-tert-butyl-4,5-dihydrooxazol-2-yl)methylthio)-4,5-dihydrothiazol-2-yl)-4-(3-(hydroxyamino)-3-oxoprop-1-enyl)-benzamide (Compound 18)

Step 15a: (E)-4-(3-Ethoxy-3-oxoprop-1-enyl)benzoic acid (Compound 0501-18)

To a solution of 4-carboxybenzaldehyde (1.33 g, 8.9 mmol) in THF (5 mL) was added ethyl (triphenylphosphoranylidene) acetate (2.97 g, 8.9 mmol) at ambient temperature under nitrogen. The reaction mixture was stirred for 1 h and concentrated in vacuo and the residue was partitioned between EtOAc and saturated aqueous NaHCO$_3$. The water layer was adjusted to pH 4 with 1 N HCl and extracted with EtOAc. The combined organic layers was washed with water and brine, dried over MgSO$_4$, and evaporated under reduced pressure. The residue was washed with hot IPE to afford 0501-18 as a solid. (1.2 g, 65% yield): LC-MS: 221 (M+1). $^1$H NMR (DMSO-d$_6$) δ 13.18 (s, 1H), 7.98-7.95 (d, J=8.7 Hz, 2H), 7.87-7.84 (d, J=8.1 Hz, 2H), 7.74-7.69 (d, J=16.2 Hz, 1H), 7.87-7.84 (d, J=10.8 Hz, 1H), 4.26-4.14 (m, 2H), 1.30-1.26 (m, 3H).

Step 15b: (E)-Ethyl 3-(4-(chlorocarbonyl)phenyl)acrylate (Compound 0502-18)

To a solution of 0501-18 (0.22 g, 1 mmol) in toluene (3 ml) was added a solution of SOCl$_2$ (0.2 ml) and 1 drop DMF in toluene (2 ml) slowly at room temperature. The reaction mixture was stirred at 80° C. for 3 h. The mixture was concentrated to afford the crude product that was used to next step reaction without further purification. LC-MS (in MeOH): 235.1 (M+1).

Step 15c: (E)-Ethyl 3-(4-(5-((5-tert-butyloxazol-2-yl)methylthio)thiazol-2-yl-carbamoyl)phenyl)acrylate (Compound 0503-18)

A mixture of 0108 (0.27 g, 1 mmol), 0502-18 (0.22 g, 1 mmol), and THF (5 ml) was stirred at 0° C. for 3 h. The mixture was concentrated and the residue was subjected to a flash column on silica gel (EtOAc:petroleum ether=1:10) to afford the pure product 0503-18 (0.1 g, 25%). LC-MS: 472.2 (M+1). $^1$H NMR (DMSO-d$_6$) δ 12.84 (s, 1H), 8.07 (d, J=8.1 Hz, 2H), 7.87 (d, J=7.5 Hz, 2H), 7.69 (d, J=15.9 Hz, 1H), 7.48 (d, J=1.2 Hz, 1H), 6.76 (d, J=15.0 Hz, 1H), 6.70 (s, 1H), 4.22-4.17 (m, 2H), 4.08 (s, 2H), 1.27-1.17 (m, 12H).

Step 15d: (E)-N-(5-((5-tert-butyloxazol-2-yl)methylthio)thiazol-2-yl)-4-(3-(hydroxylamino)-3-oxoprop-1-enyl)benzamide (Compound 18)

The title compound 18 was prepared as a solid (50 mg, 34% yield) from compound 0503-18 (150 mg, 0.32 mmol) and freshly prepared solution of hydroxylamine in methanol (2 mL) using a procedure similar to that described for compound 9 (Example 5). LC-MS: 459.1 (M+1). $^1$H NMR (DMSO-$d_6$) δ 12.86 (s, 1H), 10.89 (s, 1H), 9.17 (s, 1H), 8.10 (d, J=8.1 Hz, 2H), 7.72 (d, J=7.2 Hz, 2H), 7.53 (d, J=10.8 Hz, 1H), 6.73 (s, 1H), 6.65 (d, J=10.6 Hz, 1H), 4.10 (s, 2H), 1.20 (s, 9H).

Example 16

Preparation of (E)-N-(5-((5-tert-butyloxazol-2-yl)methylthio)-thiazol-2-yl)-3-(3-(hydroxylamino)-3-oxoprop-1-enyl)benzamide (Compound 19)

Step 16a: (E)-3-(3-Methoxy-3-oxoprop-1-enyl)benzoic acid (Compound 0501-19)

The title compound 0501-19 was prepared as a solid (2.08 g, 70% yield) from 3-carboxybenzaldehyde (2.17 g, 14.47 mmol) and methyl(triphenylphosphoranylidene) acetate (4.83 g, 14.47 mmol) using a procedure similar to that described for compound 0501-18 (Example 15): LC-MS: 207 [M+1]$^+$.

Step 16b: (E)-Methyl 3-(3-(chlorocarbonyl)phenyl)acrylate (Compound 0502-19)

The title compound 0502-19 was prepared (0.22 g, 100% yield) from 0501-19 (0.2 g, 0.97 mmol) using a procedure similar to that described for compound 0502-18 (Example 15): LC-MS (in CH$_3$OH): 221 [M+1]$^+$.

Step 16c: (E)-Methyl 3-(3-(5-((5-tert-butyloxazol-2-yl)methylthio)thiazol-2-yl-carbamoyl)phenyl)-acrylate (Compound 0503-19)

The title compound 0503-19 was prepared (0.12 g, 35% yield) from 0108 (0.2 g, 0.743 mmol) and 0502-19 (0.22 g, 0.97 mmol) using a procedure similar to that described for compound 0503-18 (Example 15): LC-MS: 458 [M+1]$^+$. $^1$H NMR (DMSO-$d_6$): δ: 8.52 (s, 1H), 8.07 (d, J=4 Hz, 1H), 7.96 (d, J=7.6 Hz, 1H), 7.75 (d, J=16 Hz, 1H), 7.61 (t, J=8 Hz, 1H), 7.52 (s, 1H), 6.83 (d, J=16 Hz, 2H), 6.73 (s, 1H), 4.11 (s, 2H), 3.76 (s, 3H), 1.20 (s, 9H).

Step 16d: (E)-Methyl 3-(3-(5-((5-tert-butyloxazol-2-yl)methylthio)thiazol-2-yl-carbamoyl)phenyl)-acrylate (Compound 19)

The title compound 19 was prepared as a solid (16 mg, 14.5% yield) from compound 0503-19 (110 mg, 0.24 mmol) and freshly prepared solution of hydroxylamine in methanol (2 mL) using a procedure similar to that described for compound 9 (Example 5): LC-MS: 459 [M+1]$^+$; $^1$H NMR (DMSO-$d_6$) δ 10.87 (s, 1H), δ 9.14 (s, 1H), δ 8.29 (s, 1H), 8.02 (d, J=7.2 Hz, 1H), 7.76 (d, J=7.2 Hz, 1H), 7.55 (t, J=8.0 Hz, 2H), 7.47 (d, 1H), 6.71 (s, 1H), 6.59 (d, J=15.2 Hz, 1H), 4.07 (s, 2H), 1.19 (s, 9H).

Example 17

Preparation of 2-(4-(5-((5-tert-butyloxazol-2-yl)methylthio) thiazol-2-ylcarbamoyl)piperidin-1-yl)-N-hydroxypyrimidine-5-carboxamide (Compound 20)

Step 17a: (z)-ethyl-2-(ethoxymethyl)-3-methoxyacrylate (Compound 0602)

Sodium (13.8 g) was added to a mixed solution of benzene (200 mL) and ethanol (27 g) at room temperature. To the mixture ethyl formate (45.0 g, 0.61 mol) and ethyl 3-ethoxypropionate (44.0 g, 0.30 mol) were added slowly at 0° C., and stirred for 2 h. Dimethyl sulfate (76.0 g, 0.61 mol) was added. The resulting mixture was heated to 50° C. and stirred for 3 h. The mixture was filtered and the filtrate was washed with water three times. Triethylammonium chloride (40.0 g, 0.29 mol) and sodium hydroxide (7.00 g, 0.175 mol) was added to the organic layer, and stirred for 4 h. The mixture was filtered. The organic layer was washed with water, dried over Na$_2$SO$_4$ and evaporated. The residue was distilled under reduced pressure to give product 0602 (18.8 g, 33%): $^1$H NMR (400 MHz, CDCl3): δ1.26 (m, 6H), 3.48 (m, 3H), 3.63 (m, 3H), 4.20 (m, 2H).

Step 17b: Ethyl 2-oxo-1,2,3,4-tetrahydropyrimidine-5-carboxylate (Compound 0603)

A mixture of 0602 (21.4 g, 0.11 mol), urea (5.70 g, 0.095 mol), and hydrochloric acid (5 mL) in ethanol (300 mL) was heated to reflux overnight. After evaporation, the residue was recrystallized from ethanol to give product 0603 (7.80 g, 65%) as a colorless prisms: LCMS: 171 [M+1]$^+$, $^1$H NMR (400 MHz, CDCl$_3$): δ 1.27 (t, J=7.2 Hz, 3H), 4.19 (m, 4H), 5.28 (s, 1H), 7.21 (d, J=5.6 Hz, 1H), 7.40 (s, 1H).

Step 17c: Ethyl 2-oxo-1,2-dihydropyrimidine-5-carboxylate (Compound 0604)

A solution of 0603 (2.50 g, 14.7 mmol) and bromine (2.40 g, 15 mmol) in acetic acid (55 mL) was heated to reflux for 1.5 h. Removal of the solvent afforded crude product 0604 (3.60 g, 99%): LCMS: 169 [M+1]$^+$, $^1$H NMR (400 MHz, CDCl3): δ 1.27 (t, J=7.2 Hz, 3H), 4.28 (q, J=7.2 Hz, 2H), 8.85 (s, 2H), 12.19 (ds, 2H).

Step 17d: Ethyl 2-chloropyrimidine-5-carboxylate (Compound 0605)

A mixture of 0604 (3.60 g, 21 mmol), phosphorus oxychloride (25 mL), and N,N-dimethylaniline (2.5 mL) was heated to reflux for 1.5 h. After removal of the solvent, ice water (10 mL) was added to the residue. The mixture was added to 2 N NaOH (90 ml), and extracted with EtOAc. After work up the residue was purified by column chromatography on silica gel (ethyl acetate in petroleum ether, 5% v/v) to give product 0605 (1.20 g, 30%): LCMS: 187 [M+1]$^+$, $^1$H NMR (300 MHz, CDCl3): δ 1.42 (t, J=7.5 Hz, 3H), 4.48 (q, J=7.5 Hz, 2H), 9.15 (s, 2H); $^1$H NMR (400 MHz, DMSO-$d_6$): δ 1.33 (t, J=6.8 Hz, 3H); 4.37 (q, J=6.8 Hz, 2H), 9.18 (s, 2H).

Step 17e: Ethyl 2-(4-(5-((5-tert-butyloxazol-2-yl)methylthio)thiazol-2-ylcarbamoyl)-piperidin-1-yl) pyrimidine-5-carboxylate (Compound 0606-20)

To a solution of compound 0110 (380 mg, 1 mmol) and diisopropyl ethylamine (1 mL) in N,N-dimethylacetamide (3 mL) was added dropwise a solution of 0605 (3 mL). The mixture was stirred at room temperature for 2 hours, diluted with ethyl acetate and partitioned with ice water. The separated organic layer was washed with water and brine, dried over Na$_2$SO$_4$, filtered and concentrated. The residue was purified by column chromatography on silica gel (ethyl acetate in petroleum ether 50% to 100% v/v) to give the title product 0606-20 (116 mg, 42%) as a white solid: LCMS: 531 [M+1]$^+$, $^1$H NMR (DMSO-d$_6$) δ 1.156 (s, 9H), 1.262-1.297 (m, 2H), 1.505-1.587 (m, 2H), 1.884-1.978 (m, 2H), 2.809-2.865 (t, J=11.2 Hz, 1H), 3.051-3.109 (t, J=11.6 Hz, 2H), 4.042 (s, 2H), 4.232-4.286 (q, J=7.2, 14 Hz, 2H), 4.738-4.771 (d, J=13.2 Hz, 2H), 6.704 (s, 1H), 7.387 (s, 1H), 8.782 (s, 2H), 12.360 (s, 1H).

Step 17f: 2-(4-(5-((5-Tert-butyloxazol-2-yl)methylthio)thiazol-2-ylcarbamoyl)-piperidin-1-yl)-N-hydroxypyrimidine-5-carboxamide (Compound 20)

Compound 0606-20 (116 mg, 0.22 mmol) was added to the freshly prepared hydroxylamine solution in methanol (2.0 mL, 3.4 mmol) and stirred at 25° C. for 2 hours. The mixture was neutralized with acetic acid and filtered. The filtrate was purified by prep.-HPLC to give title compound 20 (50 mg, 44%) as a white solid. mp: 181-183° C. LCMS: 518 [M+1]$^+$, $^1$H NMR (DMSO-d$_6$) δ 1.155 (s, 9H), 1.487-1.568 (m, 2H), 1.858-1.885 (m, 2H), 2.818-2.845 (t, J=10.8 Hz, 1H), 2.993-3.051 (t, J=11.2 Hz, 2H), 4.038 (s, 2H), 4.697-4.730 (d, J=13.2 Hz, 2H), 6.701 (s, 1H), 7.384 (s, 1H), 8.664 (s, 2H), 9.010 (s, 1H), 11.070 (s, 1H), 12.340 (s, 1H).

Example 18

Preparation of 2-(4-((5-((5-tert-butyloxazol-2-yl)methylthio)-thiazol-2-ylamino)methyl)piperidin-1-yl)-N-hydroxypyrimidine-5-carboxamide (Compound 21)

Step 18a: Ethyl 2-(4-hydroxypiperidin-1-yl)pyrimidine-5-carboxylate (Compound 0701)

A mixture of compound 0605 (900 mg, 4.84 mmol), piperidin-4-ylmethanol (0.56 g, 4.86 mmol) and potassium carbonate (330 mg, 2.39 mmol) in DMF (2 mL) was stirred at ambient temperature for 2.5 h. The DMF was removed under reduced pressure and the residue was poured into brine, filtered to obtain the product 0701 (1.20 g, 95%) as a yellow solid: LCMS: 266 [M+1]$^+$. $^1$H NMR (400 MHz, DMSO-d$_6$) δ 1.10 (m, 2H), 1.29 (t, J=7.2 Hz, 3H), 1.72 (m, 3H), 2.97 (m, 2H), 3.27 (m, 2H), 4.26 (q, J=7.2 Hz, 2H), 4.75 (m, 2H), 8.76 (m, 2H).

Step 18b: Ethyl 2-(4-formylpiperidin-1-yl)pyrimidine-5-carboxylate (Compound 0702)

To a solution of oxalyl dichloride (0.30 mL, 3.30 mmol) in dichloromethane (10 mL) under N$_2$ flow was added DMSO (0.58 mL, 8.20 mmol) dropwise at −78° C. and stirred for 15 minutes at that temperature followed by the addition of a solution of 0701 (0.71 g, 2.69 mmol) in dry dichloromethane (5 mL) at −78° C. The reaction mixture was stirred at −78° C. for additional 1.5 h. Et$_3$N (1.90 mL, 13.45 mmol) was added into the mixture dropwise. After 1 hour, the mixture was warmed to room temperature, poured into water (20 mL) and extracted with dichloromethane. The organic layer was dried over Na$_2$SO$_4$, filtered and concentrated to provide the product 0702 (0.55 g, 78%): LCMS: 264 [M+1]$^+$. $^1$H NMR (400 MHz, DMSO-d$_6$) δ 1.29 (t, J=7.2 Hz, 3H), 1.45 (m, 1H), 1.50 (m, 1H), 1.93 (m, 1H), 1.95 (m, 1H), 2.69 (m, 1H), 3.29 (t, J=2.8 Hz, 2H), 3.33 (t, J=3.2 Hz, 2H), 4.26 (q, J=7.2 Hz, 2H), 4.50 (t, J=4 Hz, 1H), 4.54 (s, J=4 Hz, 1H), 8.78 (s, 2H), 9.62 (s, 1H).

Step 18c: Ethyl 2-(4-((5-((5-tert-butyloxazol-2-yl)methylthio)thiazol-2-ylamino)-methyl)piperidin-1-yl)pyrimidine-5-carboxylate (Compound 0703-21)

To a mixture of 0702 (1.10 g, 4.18 mmol) in methanol (30 mL) was added compound 0108 (1 g, 3.71 mmol) and two drops of acetic acid. The mixture was stirred for 2 h at 63° C., followed by addition of NaBH$_3$CN (0.42 g, 6.68 mmol). The reaction mixture was stirred for 4 h at 63° C., cooled to room temperature and water (20 mL) was added, extracted with ethyl acetate. The organic layer was washed with water and brine, dried over Na$_2$SO$_4$, filtered and concentrated. The residue was purified by prep. HPLC to afford pure product 0703-21 (900 mg, 47%): LCMS: 517 [M+1]$^+$. $^1$H NMR (400 MHz, DMSO-d$_6$) δ 1.08 (m, 2H), 1.19 (s, 9H), 1.27 (t, J=7.2 Hz, 3H), 1.75 (m, 2H), 1.90 (m, 1H), 2.95 (t, J=12.0 Hz, 2H), 3.10 (t, J=5.6 Hz 2H), 3.93 (s, 2H), 4.25 (q, J=7.6 Hz, 2H), 4.75 (m, 2H), 6.71 (s, 1H), 6.93 (s, 1H), 8.11 (s, 1H), 8.75 (s, 1H).

Step 18d: 2-(4-((5-((5-Tert-butyloxazol-2-yl)methylthio)thiazol-2-ylamino)methyl)piperidin-1-yl)-N-hydroxypyrimidine-5-carboxamide (Compound 21)

The mixture of 0703-21 (720 mg, 1.39 mmol) and a solution of freshly prepared hydroxylamine in methanol (2 mL) was stirred for 30 min at room temperature. The mixture was adjusted to pH 7 with dilute hydrochloric acid (1 M) and concentrated. The residue was diluted with water and filtered. The crude product was purified by prep.HPLC to afford pure product 21 (400 mg, 57%) as a white solid: m.p. 153-154° C. LCMS: 504 [M+1]+; 1H NMR (400 MHz, DMSO-d$_6$) δ 1.07 (m, 2H), 1.20 (s, 9H), 1.72 (m, 2H), 1.87 (br s, 1H), 2.90 (t, J=11.6 Hz, 2H), 3.09 (t, J=5.6 Hz, 2H), 3.93 (s, 2H), 4.71 (d, J=12.4 Hz, 2H), 6.72 (s, 1H), 6.90 (s, 1H), 8.00 (t, J=5.2 Hz, 1H), 8.64 (s, 2H), 9.01 (s, 1H), 11.04 (s, 1H).

Example 19

Preparation of N$^1$-(5-((5-tert-butyloxazol-2-yl)methylthio)-1,3,4-thiadiazol-2-yl)-N$^8$-hydroxyoctanediamide (Compound 22)

Step 19a: Methyl-8-(5-((5-tert-butyloxazol-2-yl)methylthio)-1,3,4-thiadiazol-2-yl-amino)-8-oxooctanoate (Compound 0301-22)

A mixture of 5-((5-tert-butyloxazol-2-yl)methylthio)-1,3,4-thiadiazol-2-amine (compound 0108) (500 mg, 1.85 mmol), EDCI.HCl (530 mg, 2.77 mmol), HOBt (370 mg, 2.77 mmol), monomethyl suberate (380 mg, 2.08 mmol), and DIEA (715 mg, 5.55 mmol) in DMF (10 ml) was stirred at room temperature for 24 hours. The mixture was diluted with ethyl acetate and washed with water (2×30 mL) and brine. The organic phase was concentrated under reduce pressure to give crude produce 0301-22 (0.2 g) which was used directly to the next step without purification. LCMS: 441 [M+1]$^+$.

Step 19b: N$^1$-(5-((5-tert-butyloxazol-2-yl)methylthio)-1,3,4-thiadiazol-2-yl)-N$^8$-hydroxyoctanediamide (Compound 22)

The title compound 22 was prepared as a pale white solid (30 mg, 34% yield) from compound 0301-22 (120 mg, 0.27 mmol) and freshly prepared solution of hydroxylamine in methanol (1.77 M, 4 mL) using a procedure similar to that described for compound 9 (Example 5): m.p. 125~127° C., LCMS: 506 [M+1]$^+$; $^1$H NMR (400 MHz, DMSO-d$_6$) δ 1.18 (s, 9H), 1.24 (m, 4H), 1.47 (m, 2H), 1.57 (m, 2H), 1.92 (t, J=3.2 Hz, 2H), 2.45 (t, J=3.2 Hz, 2H), 3.16 (d, J=5.2 Hz 1H), 4.5 (s, 2H), 6.75 (s, 1H), 8.65 (s, 1H), 10.3 (s, 1H), 12.56 (s, 1H).

Example 20

Preparation of 3-(4-(2-(5-((5-tert-butyloxazol-2-yl) methylthio)-thiazol-2-ylamino)-2-oxoethyl)phenoxy)-N-hydroxypropanamide (Compound 23)

Step 20a: Methyl 3-(4-(2-(5-((5-tert-butyloxazol-2-yl)methylthio)thiazol-2-ylamino)-2-oxoethyl)phenoxy)propanoate (Compound 0203-23)

To the solution of 2-(4-(3-methoxy-3-oxopropoxy)phenyl) acetic acid (compound 0202-23) (0.20 g, 0.84 mmol) in DMF (3 mL) and Et$_3$N (0.5 mL) was added EDCI (0.24 g, 1.26 mmol) and HOBt (0.17 g, 1.26 mmol). The mixture was stirred at room temperature for 10 min. Then compound 0108 (0.34 g, 1.26 mmol) was added to the mixture and stirred at 30° C. overnight. The solvent was evaporated under reduced pressure and the residue was partitioned between ethyl acetate and water. The organic layer was separated and dried over Na$_2$SO$_4$, filtered and concentrated to give a residue which was purified by column chromatography eluting with ethyl acetate in petroleum ether (30% v/v) to afford the title compound 0203-23 (130 mg, 32%) as a yellow solid. LCMS: 490 [M+1]$^+$; $^1$H NMR (400 MHz, DMSO-d$_6$) δ 1.14 (s, 9H), 2.78 (t, J=6.0 Hz, 2H), 3.63 (s, 3H), 3.66 (s, 2H), 4.04 (s, 2H), 4.16 (t, J=6.0 Hz, 2H), 6.70 (s, 1H), 6.88 (d, J=8.4 Hz, 2H), 7.21 (d, J=8.4 Hz, 2H), 7.39 (s, 1H), 12.5 (s, 1H).

Step 20b: 3-(4-(2-(5-((5-Tert-butyloxazol-2-yl)methylthio)thiazol-2-ylamino)-2-oxo-ethyl)phenoxy)-N-hydroxypropanamide (Compound 23)

Methyl 3-(4-(2-(5-((5-tert-butyloxazol-2-yl)methylthio)thiazol-2-ylamino)-2-oxo-ethyl)phenoxy)propanoate (0203-23) (130 mg, 0.27 mmol) was added to a freshly prepared solution of hydroxylamine in methanol (2.50 mL). The mixture was stirred at room temperature for 1 hour and then neutralized with diluted HCl. The mixture was concentrated and the residue was purified by prep. TLC eluting with methanol in dichloromethane (8% v/v) to give the title compound 23 (56 mg, 43%) as a yellow solid: m.p. 93-95° C. LCMS: 491 [M+1]$^+$; $^1$H NMR (400 MHz, DMSO-d$_6$) δ 1.15 (s, 9H), 2.40 (t, J=6.0 Hz, 2H), 3.66 (s, 2H), 4.04 (s, 2H), 4.15 (t, J=6.0 Hz, 2H), 6.70 (s, 1H), 6.88 (d, J=8.4 Hz, 2H), 7.20 (d, J=8.4 Hz, 2H), 7.39 (s, 1H), 8.84 (s, 1H), 10.52 (s, 1H), 12.5 (s, 1H).

Example 21

Preparation of N-(5-((5-tert-butyloxazol-2-yl)methylthio)thiazol-2-yl)-4-(5-(hydroxyamino)-5-oxopentyloxy)benzamide (Compound 24)

Step 21a: 4-(5-Methoxy-5-oxopentyloxy)benzoic acid (Compound 0202-24)

4-Hydroxybenxoic acid (2.00 g, 14.48 mmol) was added to a solution of sodium methoxide (1.57 g, 29.06 mmol) in methanol (30 mL). The mixture was stirred at room temperature for 5 min, followed by the addition of ethyl 5-bromopentanoate (4.50 g, 21.52 mmol). The mixture was stirred at 50° C. overnight. The solvent was removed and the residue was dissolved in water, adjusted to pH 6 with dilute hydrochloric acid (1 M). The solid was collected by filtration and dried to afford product 0202-24 (1.16 g, 32%) as a white solid: LCMS: 275 [M+23]$^+$. $^1$H NMR (400 MHz, DMSO-d$_6$): δ 1.68 (m, 2H), 1.93 (m, 2H), 2.39 (t, J=7.2 Hz, 2H), 3.59 (s, 3H), 4.05 (t, J=5.6 Hz, 2H), 7.00 (d, J=8.8 Hz, 2H), 7.88 (d, J=8.4 Hz, 2H), 12.59 (s, 1H).

Step 21b: Methyl 5-(4-(5-((5-tert-butyloxazol-2-yl) methylthio)thiazol-2-yl-carbamoyl)phenoxy)pentanoate (Compound 0203-24)

The title compound 0203-24 was prepared as a grey solid (110 mg, 20%) from compound 0202-24 (0.28 g, 1.11 mmol), compound 0108 (0.30 g, 1.11 mmol), EDCI HCl (0.32 g, 1.67 mmol), HOBt (0.23 g, 1.67 mmol) and TEA (0.5 mL) in DMF (3 mL) using a procedure similar to that described for compound 0203-23 (Example 20): 504 [M+1]$^+$. $^1$H NMR (400 MHz, DMSO-d$_6$): δ 1.19 (s, 9H), 1.70 (m, 2H), 1.74 (m, 2H), 2.40 (t, J=7.2 Hz, 2H), 3.59 (s, 3H), 4.08 (t, J=6.4 Hz, 2H), 4.09 (s, 2H), 6.72 (s, 1H), 7.06 (d, J=8.8 Hz, 2H), 7.46 (s, 1H), 8.06 (d, J=8.8 Hz, 2H), 12.59 (s, 1H).

Step 21c: N-(5-((5-tert-butyloxazol-2-yl)methylthio) thiazol-2-yl)-4-(5-(hydroxylamino)-5-oxopentyloxy) benzamide (Compound 24)

The title compound 24 was prepared as a grey solid (24 mg, 22%) from compound 0203-24 (110 mg, 0.22 mmol) and freshly prepared solution of hydroxylamine in methanol (1.77 M, 0.6 mL) using a procedure similar to that described for compound 23 (Example 20): m.p. 167-169° C. LCMS: 519 [M+1]$^+$. $^1$H NMR (400 MHz, DMSO-d$_6$): δ 1.19 (s, 9H), 1.65 (m, 2H), 1.72 (m, 2H), 2.02 (t, J=6.8 Hz, 2H), 4.07 (t, J=6.4 Hz, 2H), 4.09 (s, 2H), 6.72 (s, 1H), 7.06 (d, J=8.8 Hz, 2H), 7.47 (s, 1H), 8.06 (d, J=8.4 Hz, 2H), 8.69 (s, 1H), 10.37 (s, 1H), 12.60 (s, 1H).

Example 22

Preparation of N-(5-((5-tert-butyloxazol-2-yl)methylthio)thiazol-2-yl)-4-(6-(hydroxyamino)-6-oxohexyloxy)benzamide (Compound 25)

Step 22a: 4-(6-Methoxy-6-oxohexyloxy)benzoic acid (Compound 0202-25)

The title compound 0202-25 was prepared as a white solid (2.11 g, 36%) from 4-hydroxybenxoic acid (3.00 g, 21.72 mmol), ethyl 6-bromohexanoate (7.27 g, 32.58 mmol) and sodium methoxide (2.35 g, 43.50 mmol) in methanol (30 mL) using a procedure similar to that described for compound 0202-24 (Example 21): LCMS: 289 [M+Na]$^+$. $^1$H NMR (400 MHz, DMSO-d$_6$): δ 1.42 (m, 2H), 1.59 (m, 2H), 1.73 (m, 2H), 2.33 (t, J=7.2 Hz, 2H), 3.59 (s, 3H), 4.03 (t, J=6.4 Hz, 2H), 7.00 (d, J=8.8 Hz, 2H), 7.88 (d, J=8.8 Hz, 2H).

Step 22b: Methyl 6-(4-(5-((5-tert-butyloxazol-2-yl) methylthio)thiazol-2-ylcarbamoyl)phenoxy)hexanoate (Compound 0203-25)

The title compound 0203-25 was prepared as a grey solid (90 mg, 16%) from compound 0202-25 (0.30 g, 1.11 mmol), compound 0108 (0.30 g, 1.11 mmol), EDCI HCl (0.32 g, 1.67 mmol), HOBt (0.23 g, 1.67 mmol) and TEA (0.5 mL) in DMF (3 mL) using a procedure similar to that described for compound 0203-23 (Example 20): LCMS: 518 [M+1]$^+$. $^1$H NMR (400 MHz, DMSO-d$_6$): δ 1.19 (s, 9H), 1.42 (m, 2H), 1.60 (m, 2H), 1.74 (m, 2H), 2.34 (t, J=7.2 Hz, 2H), 3.59 (s, 3H), 4.06 (t, J=6.8 Hz, 2H), 4.09 (s, 2H), 6.72 (s, 1H), 7.05 (d, J=8.8 Hz, 2H), 7.46 (s, 1H), 8.06 (d, J=9.2 Hz, 2H), 12.59 (s, 1H).

Step 22c: N-(5-((5-tert-butyloxazol-2-yl)methylthio) thiazol-2-yl)-4-(6-(hydroxylamino)-6-oxohexyloxy) benzamide (Compound 25)

The title compound 25 was prepared as a grey solid (35 mg, 39%) from compound 0203-25 (90 mg, 0.17 mmol) and freshly prepared solution of hydroxylamine in methanol (1.77 M, 0.5 mL) using a procedure similar to that described for compound 23 (Example 20): m.p. 137-138° C. LCMS: 519 [M+1]$^+$. $^1$H NMR (400 MHz, DMSO-d$_6$): δ 1.19 (s, 9H), 1.39 (m, 2H), 1.56 (m, 2H), 1.73 (m, 2H), 1.97 (t, J=7.2 Hz, 2H), 4.05 (t, J=6.4 Hz, 2H), 4.09 (s, 2H), 6.72 (s, 1H), 7.05 (d, J=9.2 Hz, 2H), 7.46 (s, 1H), 8.06 (d, J=8.8 Hz, 2H), 8.67 (s, 1H), 10.35 (s, 1H), 12.60 (s, 1H).

Example 23

Preparation of 4-(4-(2-(5-(1-(5-Tert-butyloxazol-2-yl)ethylthio)-thiazol-2-ylamino)-2-oxoethyl)phenoxy)-N-hydroxybutanamide (Compound 26)

Step 23a: 2-Chloro-N-(3,3-dimethyl-2-oxobutyl) acetamide (Compound 0104-26)

To the mixture of 1-amino-3,3-dimethyl-butan-2-one hydrochloride (0103) (10.40 g, 90.30 mmol) in dichloromethane (120 mL) was added TEA (24 mL) at −5° C. under N$_2$. The mixture was stirred and cooled to −10° C. A solution of 2-chloropropanoyl chloride (6 mL, 75.00 mmol) in dichloromethane (10 mL) was added dropwise over 20 minutes while keeping the reaction temperature below −5° C. The reaction mixture was stirred for 1.5 hours and then quenched with dilute hydrochloric acid (1 M) to pH 6. The organic layer was separated and washed with dilute hydrochloric acid (1 M), brine, dried and concentrated in vacuum to afford product 0104-26 (12.1 g, 92%) as colorless oil: $^1$H NMR (400 MHz, CDCl$_3$): δ 1.15 (s, 9H), 1.68 (d, J=6.8 Hz, 3H), 4.22 (d, J=4.4 Hz, 2H), 4.38 (q, J=7.2 Hz, 1H).

Step 23b: 5-Tert-butyl-2-(1-chloroethyl)oxazole (Compound 0105-26)

A mixture of 2-chloro-N-(3,3-dimethyl-2-oxobutyl)acetamide (compound 0104-26) (12.10 g, 63.13 mmol) and POCl$_3$ (24 mL) was heated to 105° C. and stirred for 2 h under N$_2$. After being cooled to room temperature, the mixture was poured into ice. The mixture was extracted with ether. The organic layer was neutralized to pH 7 with saturated sodium bicarbonate and then washed with water, brine, dried and concentrated to yield the crude material which was distilled under reduced pressure to give product 0105-26 (9.01 g, 76%) as colorless oil: LCMS: 253 [M+1]$^+$. $^1$H NMR (400 MHz, DMSO-d$_6$): δ 1.25 (s, 9H), 1.81 (d, J=6.8 Hz, 3H), 5.41 (q, J=6.8 Hz, 1H), 6.85 (s, 1H).

Step 23c: 5-(1-(5-Tert-butyloxazol-2-yl)ethylthio) thiazol-2-amine (Compound 0108-26)

To a solution of 0107 (3.00 g, 19.08 mmol) in absolute ethanol (180 mL) was added NaBH$_4$ portionwise at room temperature. The mixture was stirred for 1 h, acetone (80 mL) was added slowly into the mixture. After 1 h, a solution of 5-tert-butyl-2-(1-chloroethyl)oxazole (compound 0105-26) (4.00 g, 21.39 mmol) in ethanol (25 mL) was added, and the resulting dark mixture heated to reflux for 1 h. The mixture was cooled and concentrated to give a residue which was partitioned between ethyl acetate and brine. The organic phase was separated, dried and concentrated in vacuum to give a crude solid which was purified by column chromatography on silica gel with ethyl acetate in petroleum ether (50% v/v) to afford the product 0108-26 (2.56 g, 50%) as a brown solid: LCMS: 253 [M+1]$^+$. $^1$H NMR (400 MHz, DMSO-d$_6$): δ 1.23 (s, 9H), 1.52 (d, J=6.8 Hz, 3H), 4.24 (q, J=7.2 Hz, 1H), 6.69 (s, 1H), 6.80 (s, 1H), 7.28 (s, 2H).

Step 23d: Methyl 4-(4-(2-(5-(1-(5-Tert-butyloxazol-2-yl)ethylthio)thiazol-2-ylamino)-2-oxoethyl)phenoxy)butanoate (Compound 0203-26)

A mixture of 2-(4-(4-Methoxy-4-oxobutoxy)phenyl)acetic acid (compound 0202-9) (0.20 g, 0.84 mmol), 5-(1-(5-tert-butyloxazol-2-yl)-ethylthio)thiazol-2-amine (compound 0108-26) (0.36 g, 1.26 mmol), EDCI HCl (0.24 g, 1.26 mmol), HOBt (0.17 g, 1.26 mmol) and TEA (0.5 mL) in DMF (3 mL) was stirred at 50° C. under N$_2$ overnight. The mixture was extracted with ethyl acetate and the organic layer was washed with water. The organic layer was concentrated and the residue was purified by column chromatography on silica gel with ethyl acetate in petroleum ether (50% v/v) to afford product 0203-26 (0.22 g, 52%) as a grey solid. LCMS: 518 [M+1]$^+$. $^1$H NMR (400 MHz, DMSO-d$_6$): δ 1.14 (s, 9H), 1.53 (d, J=6.8 Hz, 3H), 1.95 (m, 2H), 2.46 (t, J=7.2 Hz, 2H), 3.60 (s, 3H), 3.65 (s, 2H), 3.95 (t, J=6.4 Hz, 2H), 4.39 (q, J=7.2 Hz, 2H), 6.67 (s, 1H), 6.87 (d, J=8.8 Hz, 2H), 7.20 (d, J=8.8 Hz, 2H), 7.34 (s, 1H), 12.45 (s, 1H).

Step 23e: 4-(4-(2-(5-(1-(5-Tert-butyloxazol-2-yl) ethylthio)thiazol-2-ylamino)-2-oxoethyl)phenoxy)-N-hydroxybutanamide (Compound 26)

The title compound 26 was prepared as a grey solid (35 mg, 18%) from compound 0203-26 (0.20 g, 0.39 mmol) and freshly prepared solution of hydroxylamine in methanol (1.77 M, 1.5 mL) using a procedure similar to that described for compound 23 (Example 20): m.p. 81-84° C. LCMS: 519 [M+1]$^+$. $^1$H NMR (400 MHz, DMSO-d$_6$): δ 1.15 (s, 9H), 1.53 (d, J=7.2 Hz, 3H), 1.91 (m, 2H), 2.11 (t, J=7.6 Hz, 2H), 3.66 (s, 2H), 3.92 (t, J=6.4 Hz, 2H), 4.39 (q, J=7.2 Hz, 1H), 6.67 (s, 1H), 6.87 (d, J=8.4 Hz, 2H), 7.20 (d, J=8.4 Hz, 2H), 7.34 (s, 1H), 10.40 (s, 1H), 12.44 (s, 1H).

Example 24

Preparation of 4-(4-(1-(5-((5-Tert-butyloxazol-2-yl) methylthio)-thiazol-2-ylamino)-2-methyl-1-oxopropan-2-yl)phenoxy)-N-hydroxybutanamide (Compound 27)

Step 24a: 2-(4-Methoxyphenyl)-2-methylpropanenitrile (Compound 0802-27)

To a solution of t-BuOK (3.80 g, 33.87 mmol) in THF (34 mL) was added p-methoxy phenylacetonitrile (compound 0801) (2.50 g, 16.99 mmol) dropwise at 10° C. under N$_2$. The reaction mixture was then stirred for 30 min at 15° C., followed by the addition of iodomethane (4.80 g, 33.82 mmol)

over 30 min. The resulting mixture was stirred at 15° C. for 1 h. The mixture was poured into saturated aqueous sodium chloride, extracted with ethyl acetate. The organic layer was evaporated and the residue was purified by silica gel with ethyl acetate in petroleum ether (10% v/v) to afford product 0802-27 (1.63 g, 55%) as a grey solid: LCMS: 176 [M+1]. $^1$H NMR (400 MHz, DMSO-$d_6$): δ 1.65 (s, 6H), 3.76 (s, 3H), 6.97 (d, J=8.8 Hz, 2H), 7.43 (d, J=8.8 Hz, 2H).

Step 24b: 2-(4-Methoxyphenyl)-2-methylpropanoic acid (Compound 0803-27)

To a solution of 2-(4-Methoxyphenyl)-2-methylpropanenitrile (compound 0802-27) (1.63 g, 9.30 mmol) in ethylene glycol (3.40 mL) was added potassium hydroxide (1.29 g, 22.99 mmol) and water (0.46 mL). The reaction mixture was heated at 150° C. for 7 h. The mixture was poured into water, adjusted to pH 2 with concentrated hydrochloric acid. The mixture was filtered and the collected solid was washed with water and dried in vacuum to afford product 0803-27 (0.85 g, 47%) as a white solid: LCMS: 195 [M+1]$^+$. $^1$H NMR (DMSO-$d_6$): δ 1.44 (s, 6H), 3.73 (s, 3H), 6.88 (d, J=9.2 Hz, 2H), 7.25 (d, J=8.4 Hz, 2H), 12.23 (s, 1H).

Step 24c: 2-(4-Hydroxyphenyl)-2-methylpropanoic acid (Compound 0804-27)

A mixture of 2-(4-Methoxyphenyl)-2-methylpropanoic acid (compound 0803-27) (0.85 g, 4.38 mmol) and pyridine hydrochloride (2.82 g, 24.40 mmol) was heated at 180° C. for 5 h, The reaction mixture was then cooled to room temperature and adjusted to pH 6 with dilute hydrochloric acid (1 M) and extracted with ethyl acetate. The organic layer was separated, dried over $Na_2SO_4$, and concentrated to afford desired product 0804-27 (0.61 g, 76%) as a colorless oil: LCMS: 181 [M+1]$^+$. $^1$H NMR (400 MHz, DMSO-$d_6$): δ 1.41 (s, 6H), 6.70 (d, J=8.8 Hz, 2H), 7.13 (d, J=8.8 Hz, 2H), 9.28 (s, 1H), 12.16 (s, 1H).

Step 24d: 2-(4-(4-Methoxy-4-oxobutoxy)phenyl)-2-methylpropanoic acid (Compound 0805-27)

To a solution of sodium methoxide (0.36 g, 6.66 mmol) in methanol (6 mL) was added 2-(4-hydroxyphenyl)-2-methylpropanoic acid (compound 0804-27) (0.60 g, 3.33 mmol). The resulting mixture was stirred at room temperature for 5 min, followed by the addition of ethyl 4-bromobutanoate (0.65 g, 3.33 mmol). The mixture was stirred at 50° C. overnight. The solvent was removed and the residue was dissolved in water and was then adjusted to pH 6 with dilute hydrochloric acid (1 M). The resulting solid was collected by filtration to give product 0805-27 (0.28 g, 30%) as a white solid. LCMS: 303 [M+23]$^+$. $^1$H NMR (400 MHz, DMSO-$d_6$): δ 1.43 (s, 6H), 1.96 (m, 2H), 2.46 (t, J=7.2 Hz, 2H), 3.60 (s, 3H), 3.95 (t, J=6 Hz, 2H), 6.86 (d, J=9.2 Hz, 2H), 7.24 (d, J=8.8 Hz, 2H), 12.22 (s, 1H).

Step 24e: Methyl 4-(4-(1-(5-((5-tert-butyloxazol-2-yl)methylthio)thiazol-2-ylamino)-2-methyl-1-oxopropan-2-yl)phenoxy)butanoate (Compound 0806-27)

A mixture of 2-(4-(4-Methoxy-4-oxobutoxy)phenyl)-2-methylpropanoic acid (compound 0805-27) (0.25 g, 0.89 mmol), compound 0108 (0.36 g, 1.34 mmol), EDCI HCl (0.26 g, 1.34 mmol), HOBt (0.18 g, 1.34 mmol), and TEA (0.60 mL) in DMF (4 mL) was stirred at 50° C. under $N_2$ overnight. The mixture was extracted with ethyl acetate and the organic layer was washed with water, concentrated to obtain a residue which was purified by column chromatography on silica gel with ethyl acetate in petroleum ether (50% v/v) to afford product 0806-27 (0.26 g, 55%) as a colorless oil: LCMS: 532 [M+1]$^+$. $^1$H NMR (400 MHz, DMSO-$d_6$): δ 1.15 (s, 9H), 1.54 (s, 6H), 1.95 (m, 2H), 2.45 (t, J=7.2 Hz, 2H), 3.59 (s, 3H), 3.96 (t, J=6.4 Hz, 2H), 4.05 (s, 2H), 6.72 (s, 1H), 6.89 (d, J=8.8 Hz, 2H), 7.18 (d, J=8.8 Hz, 2H), 7.35 (s, 1H), 11.76 (s, 1H).

Step 24f: 4-(4-(1-(5-((5-Tert-butyloxazol-2-yl)methylthio)thiazol-2-ylamino)-2-methyl-1-oxopropan-2-yl)phenoxy)-N-hydroxybutanamide (Compound 27)

The title compound 27 was prepared as a grey solid (55 mg, 21%) from compound 0806-27 (260 mg, 0.49 mmol) and freshly prepared solution of hydroxylamine in methanol (1.77 M, 1.5 mL) using a procedure similar to that described for compound 23 (Example 20): m.p. 177-179° C. LCMS: 533 [M+1]$^+$. $^1$H NMR (400 MHz, DMSO-$d_6$): δ 1.16 (s, 9H), 1.55 (s, 6H), 1.91 (m, 2H), 2.11 (t, J=7.6 Hz, 2H), 3.93 (t, J=6 Hz, 2H), 4.05 (s, 2H), 6.71 (s, 1H), 6.89 (d, J=8.8 Hz, 2H), 7.18 (d, J=8.8 Hz, 2H), 7.35 (s, 1H), 8.68 (s, 1H), 10.39 (s, 1H), 11.74 (s, 1H).

Example 25

Preparation of 4-(4-(hydroxyamino)-4-oxobutoxy)phenyl-5-((5-tert-butyloxazol-2-yl)methylthio)thiazol-2-ylcarbamate (Compound 28)

Step 25a: Ethyl 4-(4-hydroxyphenoxy)butanoate (Compound 0902-28)

A mixture of hydrowuinone (5.0 g, 45 mmol), ethyl 4-bromobutanoate (8.77 g, 45 mmol) and anhydrous $K_2CO_3$ (3.1 g, 22.5 mmol) in DMF was stirred at 50° C. under $N_2$ for 12 h. After reaction water was added to it and the mixture was extracted with ethyl acetate. The organic layer was washed with water, brine, dried ($Na_2SO_4$) and concentrated under reduce pressure to yield a crude mixture which was purified by column chromatography on silica gel (ethyl acetate in petroleum ether, 25% to 33% v/v) to yield product 0902-28 (1.2 g, 12%) as a white solid. LCMS: 225 [M+1]$^+$.

Step 25b: Ethyl 4-(4-(5-((5-tert-butyloxazol-2-yl)methylthio)thiazol-2-ylcarbamoyloxy)phenoxy)butanoate (Compound 0903-28)

A mixture of ethyl 4-(4-hydroxyphenoxy)butanoate (0902-28) (200 mg, 0.89 mmol) and Et$_3$N (224 mg, 2.25 mmol) in anhydrous dichloromethane was stirred at 0° C. under $N_2$ for 5 minute. Then 4-nitrophenyl carbonochloridate (215 mg, 1.07 mmol) in DCM was added dropwise at 0-5° C. The solution was stirred at 0° C. for additional 2 h. and followed by the addition of compound 0108 (239 mg, 0.89 mmol) in dichloromethane. The mixture was warmed to room temperature and stirred at room temperature overnight. The solvent was removed under reduce pressure and the residue was purified by column chromatography on silica gel (petroleum ether:ethyl acetate=1:3) to yield product 0903-28 (120 mg, 28%) as a white solid LCMS: 520 [M+1]$^+$.

Step 25c: 4-(4-(Hydroxyamino)-4-oxobutoxy)phenyl-5-((5-tert-butyloxazol-2-yl)-methylthio)thiazol-2-ylcarbamate (Compound 28)

The title compound 28 was prepared as a pale white solid (18 mg, 15%) from compound 0903-28 (120 mg, 0.234 mmol) and freshly prepared solution of hydroxylamine in methanol (1.77 M, 4 mL) using a procedure similar to that described for compound 23 (Example 20): LCMS: 507 [M+1]; $^1$H NMR (400 MHz, DMSO-d$_6$) δ 1.19 (s, 9H), 1.99 (m, 2H), 2.13 (m, 2H), 3.96 (t, J=6.4 Hz, 2H), 4.04 (s, 2H), 6.72 (s, 1H), 6.95 (d, J=8.8 Hz 2H), 7.14 (d, J=8.8 Hz, 2H), 7.36 (s, 1H), 8.72 (d, 1H), 10.43 (s, 1H), 12.42 (s, 1H).

Example 26

Preparation of 4-(4-(3-(5-((5-Tert-butyloxazol-2-yl)methylthio)-thiazol-2-yl)ureido)phenoxy)-N-hydroxybutanamide (Compound 29)

Step 26a: Tert-butyl 4-hydroxyphenylcarbamate (Compound 1002-29)

To a solution of 4-aminophenol 3.27 g, 29.96 mmol) in THF (30 mL) was added NaHCO$_3$ (5.0 g, 59.92 mmol) and Boc$_2$O (6.55 g, 30.01 mmol). The reaction mixture was stirred at room temperature for 0.5 h. The mixture was extracted with ethyl acetate. The organic layer was washed with water, dried over Na$_2$SO$_4$, filtered, and evaporated to provide the product 1002-29 (6.1 g, 97%) as a white solid: LCMS: 154 [M+1]$^+$. $^1$H NMR (400 MHz, DMSO-d$_6$): δ 1.45 (s, 9H), 6.64 (d, J=8.8 Hz, 2H), 7.2 (d, J=8 Hz, 2H), 8.98 (s, 1H), 9.03 (s, 1H).

Step 26b: Ethyl 4-(4-(tert-butoxycarbonylamino)phenoxy)butanoate (Compound 1003-29)

To a solution of 1002-29 (5.00 g, 23.90 mmol) in DMF (40 mL) was added K$_2$CO$_3$ (5.30 g, 38.35 mmol) and ethyl 4-bromobutanoate (8.20 g, 42.04 mmol). The reaction mixture was stirred at 50° C. for 2 h. The mixture was extracted with ethyl acetate. The organic layer was washed with water (20 mL×5) and brine, dried over with Na$_2$SO$_4$, and concentrated. The residue was purified by flash column (ethyl acetate in petroleum ether 10% v/v) to afford product 1003-29 (4 g, 55%) as a white solid: LCMS: 268 [M+1]$^+$. $^1$H NMR (400 MHz, DMSO-d$_6$): δ 1.18 (t, J=7.2 Hz, 3H), 1.45 (s, 9H), 1.93 (m, 2H), 2.43 (t, J=7.2 Hz, 1H), 3.91 (t, J=6 Hz, 1H), 4.07 (q, J=7.2 Hz, 1H), 6.81 (d, J=8.8 Hz, 2H), 7.32 (d, J=8.4 Hz, 2H), 9.11 (s, 1H).

Step 26c: Ethyl 4-(4-aminophenoxy)butanoate (Compound 1004-29)

A mixture of 1003-29 (2.70 g, 8.36 mmol) and HCl in dioxane (4M, 10 mL) was stirred at ambient temperature for one hour under N$_2$, then the solvent was removed. The residue was adjusted to pH 7 with aqueous Na$_2$HCO$_3$, extracted with ethyl acetate. The organic layer was dried over Na$_2$SO$_4$ and concentrated. The residue was purified by column flash (ethyl acetate in petroleum ether 50% v/v) to afford product 1004-29 (1.71 g, 91%) as a white solid: LCMS: 224 [M+1]. $^1$H NMR (400 MHz, DMSO-d$_6$): δ 1.18 (t, J=6.8 Hz, 3H), 1.89 (m, 2H), 2.41 (t, J=7.6 Hz, 2H), 3.82 (t, J=6.4 Hz, 2H), 4.07 (q, J=7.2 Hz, 2H), 4.59 (s, 2H), 6.49 (d, J=8.8 Hz, 2H), 6.62 (d, J=8.8 Hz, 2H).

Step 26d: Ethyl 4-(4-(3-(5-((5-Tert-butyloxazol-2-yl)methylthio)thiazol-2-yl)ureido)-phenoxy)butanoate (Compound 1005-29)

To a solution of 0108 (360 mg, 1.34 mmol), Et$_3$N (340 mg, 3.35 mmol) in dichloromethane (5 mL) was added 4-nitrophenyl carbonochloridate (330 mg, 1.61 mmol) at 0° C. The mixture was stirred at 0° C. for 2 h. Then 1004-29 (300 mg, 1.34 mmol) was added into the mixture. The reaction mixture was stirred at room temperature overnight. The solvent was removed and the residue was purified by prep.HPLC to afford the product 1005-29 (190 mg, 28%) as a grey solid: LCMS: 519 [M+1]$^+$. $^1$H NMR (400 MHz, DMSO-d$_6$): δ 1.17 (t, J=7.6 Hz, 3H), 1.19 (s, 9H), 1.94 (m, 2H), 2.44 (t, J=7.2 Hz, 2H), 3.94 (t, J=6 Hz, 2H), 4.03 (s, 2H), 4.07 (d, J=7.2 Hz, 2H), 6.71 (s, 2H), 6.87 (d, J=9.6 Hz, 2H), 7.27 (s, 2H), 7.33 (d, J=8.8 Hz, 2H), 8.75 (s, 1H), 10.61 (s, 1H).

Step 26e: 4-(4-(3-(5-((5-Tert-butyloxazol-2-yl)methylthio)thiazol-2-yl)ureido)-phenoxy)-N-hydroxybutanamide (compound 29)

The title compound 29 was prepared as a grey solid (75 mg, 41%) from compound 1005-29 (190 mg, 0.37 mmol) and freshly prepared solution of hydroxylamine in methanol (1.77 M, 4 mL) using a procedure similar to that described for compound 23 (Example 20): m.p. 125-127° C. LCMS: 506 [M+1]$^+$. $^1$H NMR (400 MHz, DMSO-d$_6$): δ 1.20 (s, 9H), 1.91 (m, 2H), 2.12 (t, J=7.6 Hz, 2H), 3.92 (t, J=6 Hz, 2H), 4.04 (s, 2H), 6.72 (s, 1H), 6.89 (d, J=9.2 Hz, 2H), 7.27 (s, 1H), 7.34 (d, J=8.8 Hz, 2H), 8.70 (s, 1H), 8.74 (s, 1H), 10.41 (s, 1H), 10.59 (s, 1H).

Example 27

Preparation of 4-(4-(2-(5-((5-tert-butyloxazol-2-yl)methylthio)-1,3,4-thiadiazol-2-ylamino)-2-oxoethyl)phenoxy)-N-hydroxybutanamide (Compound 30)

Step 27a: 5-((5-tert-butyloxazol-2-yl)methylthio)-1,3,4-thiadiazol-2-amine (Compound 1103)

A solution of 5-amino-1,3,4-thiadiazole-2-thiol (2.0 g, 15 mmol), DMF (50 mL), KOH (1.26 g, 22.5 mmol) and 5-tert-butyl-2-(chloromethyl)oxazole (2.6 g, 15 mmol) was stirred at room temperature for 1 h. Water was then added and extracted with ethyl acetate. The organic lay was washed with water, brine and dried (Na$_2$SO$_4$). The solution was concentrated under reduce pressure to obtain compound 1103 (3.6 g, 90%). LCMS: 270 [M+1]$^+$.

Step 27b: Methyl-4-(4-(2-(5-((5-tert-butyloxazol-2-yl)methylthio)-1,3,4-thiadiazol-2-ylamino)-2-oxoethyl)phenoxy)butanoate (Compound 1104-30)

The title compound 1104-30 was prepared (300 mg, 30%) from compound 0202-26 (460 mg, 1.85 mmol) using a procedure similar to that described for 0203-26 (Example 23): LCMS: 520 [M+1]$^+$. $^1$H NMR (400 MHz, DMSO-d$_6$) δ 1.15 (s, 9H), 1.95 (m, 2H), 2.45 (m, 2H) 3.59 (s, 3H), 3.72 (s, 2H), 3.95 (m, 2H), 4.5 (s, 2H), 6.73 (s, 1H), 6.86 (d, J=8.4 Hz, 2H), 7.2 (s, J=8.4 Hz, 2H), 12.87 (s, 1H).

Step 27c: 4-(4-(2-(5-((5-tert-butyloxazol-2-yl)methylthio)-1,3,4-thiadiazol-2-yl-amino)-2-oxoethyl)phenoxy)-N-hydroxybutanamide (Compound 30)

The title compound 30 was prepared (260 mg, 86%) from compound 1104 (300 mg, 0.60 mmol) using a procedure similar to that described for compound 26 (Example 23): LCMS: 506 [M+1]$^+$. $^1$H NMR (400 MHz, DMSO-d$_6$) δ 1.15 (s, 9H), 1.90 (m, 2H), 2.11 (m, 2H), 3.72 (s, 2H), 3.92 (m, J=6.4 Hz, 2H), 4.5 (s, 2H), 6.73 (s, 1H), 6.86 (d, J=8.4 Hz, 2H), 7.2 (s, J=8.4 Hz 2H), 8.70 (s, 1H), 10.41 (s, 1H), 12.83 (s, 1H).

Example 28

Preparation of 4-(4-(1-(5-((5-Tert-butyloxazol-2-yl) methylthio)-thiazol-2-ylamino)-1-oxopropan-2-yl) phenoxy)-N-hydroxybutanamide (Compound 31)

Step 28a: 2-(4-(4-Methoxy-4-oxobutoxy)phenyl) propanoic acid (Compound 1202)

2-(4-Hydroxyphenyl)-propionic acid (3.00 g, 18.05 mmol) was added to a solution of sodium methoxide (1.95 g, 36.10 mmol) in methanol (30 mL). The mixture was stirred at room temperature for 5 min and followed by the addition of ethyl 4-bromobutanoate (3.52 g, 18.05 mmol). The mixture was stirred at 50° C. overnight. The solvent was removed and the residue was dissolved in water, adjusted to pH 6 with dilute hydrochloric acid (1 M), filtered, evaporated and dried to afford product 1202 (3.2 g, 67%) as a white solid: LCMS: 267 [M+1]$^+$. $^1$H NMR (400 MHz, DMSO-d$_6$): δ 1.32 (d, J=6 Hz, 3H), 1.95 (m, 2H), 2.46 (t, J=6 Hz, 2H), 3.58 (m, 1H), 3.60 (s, 3H), 3.95 (t, J=5.2 Hz, 2H), 6.86 (d, J=6.8 Hz, 2H), 7.18 (d, J=7.2 Hz, 2H), 12.21 (s, 1H).

Step 28b: Methyl 4-(4-(1-(5-((5-tert-butyloxazol-2-yl)methylthio)thiazol-2-ylamino)-1-oxopropan-2-yl) phenoxy)butanoate (Compound 1203)

To a mixture of 1202 (0.40 g, 15.02 mmol) in DMF (6 mL) was added 0108 (0.60 g, 2.25 mmol), EDCI HCl (0.43 g, 2.25 mmol), HOBt (0.30 g, 2.25 mmol) and TEA (1 mL). The reaction mixture was stirred at 50° C. under N$_2$ overnight. The mixture was extracted with ethyl acetate and the organic layer was washed with water. The organic layers was concentrated and the residue was purified by column chromatography on silica gel (ethyl acetate in petroleum ether 50% v/v) to afford product 1203 (0.59 g, 76%) as a grey solid: LCMS: 518 [M+1]$^+$. $^1$H NMR (400 MHz, DMSO-d$_6$): δ 1.11 (s, 9H), 1.38 (d, J=7.2 Hz, 3H), 1.94 (m, 2H), 2.45 (t, J=7.6 Hz, 2H), 3.59 (s, 3H), 3.87 (m, 1H), 3.94 (t, J=6.4 Hz, 2H), 4.04 (s, 2H), 6.70 (s, 1H), 6.87 (d, J=8.4 Hz, 2H), 7.25 (d, J=8.4 Hz, 2H), 7.38 (s, 1H), 12.39 (s, 1H).

Step 28c: 4-(4-(1-(5-((5-Tert-butyloxazol-2-yl)methylthio)thiazol-2-ylamino)-1-oxo-propan-2-yl)phenoxy)-N-hydroxybutanamide (Compound 31)

The title compound 31 was prepared as a grey solid (256 mg, 51%) from compound 1203 (0.50 g, 0.97 mmol) and freshly prepared hydroxylamine in methanol (1.77 M, 4 mL) using a procedure similar to that described for compound 26 (Example 23): m.p. 137-139° C. LCMS: 519 [M+1]$^+$. $^1$H NMR (400 MHz, DMSO-d$_6$): δ 1.12 (s, 9H), 1.38 (d, J=5.6 Hz, 3H), 1.90 (m, 2H), 2.10 (t, J=5.6 Hz, 2H), 3.88 (m, 1H), 3.92 (t, J=5.2 Hz, 2H), 4.04 (s, 2H), 6.70 (s, 1H), 6.87 (d, J=7.2 Hz, 2H), 7.25 (d, J=6.8 Hz, 2H), 7.37 (s, 1H), 8.70 (s, 1H), 10.40 (s, 1H), 12.39 (s, 1H).

Example 29

Preparation of (E)-methyl 3-(3-(N-(5-((5-tert-butyloxazol-2-yl)-methylthio)thiazol-2-yl)sulfamoyl) phenyl)acrylate (Compound 32)

Step 29a: Sodium 3-formylbenzenesulfonate (Compound 1302)

Benzaldehyde (4 g, 37.68 mmol) was slowly added to SO$_3$ (50% H$_2$SO$_4$) (10 mL) at the temperature below 30° C. The obtained solution was stirred at 40° C. for 10 h and then at room temperature overnight. The reaction mixture was poured into ice and extracted with ethyl acetate. The aqueous phase was treated with CaCO$_3$ until the evolution of CO$_2$ (pH 6~7), filtered, and washed with water. The filtrate was adjusted to pH8 with Na$_2$CO$_3$, filtered, evaporated under reduced pressure. The residue was mixed well with methanol and then filtered. The filtrate was concentrated and dried to give product 1302 (4.0 g, 51%): $^1$H NMR (400 MHz, D$_2$O) δ 7.63 (t, J=8 Hz, 1H), 7.99 (d, J=7.2 Hz, 2H), 8.19 (s, 1H), 9.88 (s, 1H).

Step 29b: Sodium (E)-3-(3-methoxy-3-oxoprop-1-enyl)benzenesulfonate (Compound 1303)

A mixture of 1302 (0.5 g, 2.4 mmol), K$_2$CO$_3$ (0.66 g, 4.78 mmol), trimethyl phosphonoacetate (0.53 g, 2.88 mmol) in water (10 mL) was stirred at room temperature for 30 min. The resulting solid was isolated and washed with ethanol to give product 1303 (0.35 g, 55%) as a white solid: $^1$H NMR (400 MHz, DMSO-d$_6$) δ 3.72 (s, 1H), 6.59 (d, J=16 Hz, 1H), 7.39 (t, J=8 Hz, 1H), 7.67 (m, 3H), 7.83 (s, 1H).

Step 29c: (E)-methyl 3-(3-(chlorosulfonyl)phenyl) acrylate (Compound 1306-32)

To a suspension of 1303 (1 g, 37.7 mmol) in dry toluene (15 mL) containing 1 drop of DMF was added SOCl$_2$ (1.2 mL). The mixture was heated to 80° C. for 1.5 h. The reaction mixture was concentrated to give the product 1306-32 (0.95 g, 97%). LCMS: 261 [M+1]$^+$.

Step 29d: (E)-methyl 3-(3-(N-(5-((5-tert-butyloxazol-2-yl)methylthio)thiazol-2-yl)-sulfamoyl)phenyl) acrylate (Compound 1307-32)

A mixture of 1306-32 (0.29 g, 1.11 mmol), 0108 (0.2 g, 0.74 mmol) in 1 ml pyridine was heated to 50° C. for 2 h under N$_2$ atmosphere at room temperature, followed by the addition of 2nd part of (E)-methyl 3-(3-(chlorosulfonyl)phenyl)acrylate (0.29 g, 1.11 mmol) in pyridine (1 ml). The resulting mixture was then stirred at 60° C. for 2.5 h. The solvent was removed and the residue was treated with 1N HCl, filtered, washed with water, and dried to give the crude product. The crude product was dissolved in methanol (20 mL) and conc. H$_2$SO$_4$ (1 mL). The mixture was heated to 80° C. for 1 h, cooled to room temperature and adjusted to pH 7. The solvent was removed and the residue was treated with water, filtered and dried to afford product 1307-32 (140 mg, 38%) as a solid: LCMS: 494 [M+1]$^+$. $^1$H NMR (400 MHz, DMSO-d$_6$) δ 1.17 (s, 9H), 3.74 (s, 3H), 4.11 (s, 2H), 6.77 (m, 2H), 7.41 (s, 1H), 7.71 (d, J=13.2 Hz, 1H), 7.76 (s, 1H), 7.78 (s, 1H), 7.91 (d, J=8.8 Hz, 2H), 12.97 (s, 1H).

Step 29e: (E)-3-(3-(N-(5-((5-tert-butyloxazol-2-yl) methylthio)thiazol-2-yl)sulfamoyl)phenyl)-N-hydroxyacrylamide (Compound 32)

The title compound 32 was prepared as a white solid (20 mg, 16%) from compound 1307-32 (130 mg, 0.26 mmol) and freshly prepared hydroxylamine in methanol (1.77 M, 10 mL) using a procedure similar to that described for compound 26 (Example 23): LCMS: 495 [M+1]$^+$. $^1$H NMR (400 MHz, DMSO-d$_6$) δ 1.15 (s, 9H), 4.12 (s, 2H), 6.56 (d, J=5.5 Hz, 1H), 6.73 (s, 1H), 7.39 (s, 1H), 7.52 (d, J=15.5 Hz, 1H), 7.60

(t, J=7.5 Hz, 1H), 7.75 (d, J=7.5 Hz, 1H), 7.80 (d, J=8.0 Hz, 1H), 7.92 (s, 1H), 9.18 (s, 1H), 10.80 (s, 1H), 12.94 (s, 1H).

Example 30

Preparation of 4-(N-(5-((5-tert-butyloxazol-2-yl)methylthio)-thiazol-2-yl)sulfamoyl)-N-hydroxybenzamide (Compound 33)

Step 30a: 4-(Chlorosulfonyl)benzoic acid (Compound 1402)

To a solution of p-toluenesulfonyl chloride (1.9 g, 0.01 mol) in HAc/Ac$_2$O (20 ml/10 ml) was added chromium (VI) oxide (3.0 g, 0.03 mol) in portions at room temperature. The mixture was heated to 40° C. for 2 h. and then the reaction mixture was poured into ice water, filtered, and dried to afford product 1402 (1.2 g, 55%): LCMS: 221 [M+1]$^+$. $^1$H NMR (400 MHz, DMSO-d$_6$) δ 7.71 (d, J=2.0 Hz, 2H), 7.92 (d, J=6.0 Hz, 2H), 13.92 (s, 1H).

Step 30b: Methyl 4-(chlorosulfonyl)benzoate (Compound 1403)

A suspension of 1402 (3.0 g, 13.6 mmol) and thionyl chloride (10 ml) in dichloroethane (5 ml) was heated to reflux for 1 hr. The mixture was concentrated in vacuo to give a light-brown solid. Ice-cold methanol (20 ml) was then added to the solid at ice bath temperature and stirred for 5 min. The mixture was then warmed to room temperature and stirred for 10 min. During stirring a white precipitate was formed. Ice-cold water (20 ml) was added into the mixture and yielded copious precipitation. The solid product was filtered, washed with ice-cold water, and dried under vacuum to give product 1403 (2.0 g, 63%) as a white solid: LCMS: 235 [M+1]$^+$. $^1$H NMR (400 MHz, DMSO-d$_6$) δ 3.86 (s, 3H), 7.75 (d, J=3.6 Hz, 2H), 7.95 (d, J=3.6 Hz, 2H).

Step 30c: Methyl 4-(N-(5-((5-tert-butyloxazol-2-yl)methylthio)thiazol-2-yl)sulfamoyl)benzoate (Compound 1404)

A mixture of 0108 (0.27 g, 1 mmol), 1403 (0.23 g, 1 mol) in pyridine (10 ml) was stirred at 0° C. for 3 h. Water was added to afford the crude product. The crude product was purified by flash column chromatography (EtOAc:petroleum ether=1:10) to afford the pure product 1404 (0.35 g, 76%): LCMS: 468 [M+1]$^+$. $^1$H NMR (400 MHz, DMSO-d$_6$) δ 1.16 (s, 9H), 3.88 (s, 3H), 4.13 (s, 2H), 6.94 (s, 1H), 7.91 (d, J=5.1 Hz, 2H), 8.12 (d, J=5.1 Hz, 2H), 12.06 (s, 1H).

Step 30d: 4-(N-(5-((5-Tert-butyloxazol-2-yl)methylthio)thiazol-2-yl)sulfamoyl)-N-hydroxybenzamide (Compound 33)

The title compound 33 was prepared as an off-white solid (95 mg, 47%) from compound 1404 (200 mg, 0.43 mmol) and freshly prepared hydroxylamine in methanol (1.77 M, 5 mL) using a procedure similar to that described for compound 26 (Example 23): LCMS: 468.9 [M+1]$^+$. $^1$H NMR (400 MHz, DMSO-d$_6$) δ 1.19 (s, 9H), 4.13 (s, 2H), 6.77 (s, 1H), 7.84 (d, J=5.1 Hz, 2H), 7.90 (d, J=5.1 Hz, 2H), 11.41 (s, 1H), 13.02 (s, 1H).

Example 31

Preparation of (E)-3-(4-(N-(5-((5-tert-butyloxazol-2-yl)methylthio)-thiazol-2-yl)sulfamoyl)phenyl)-N-hydroxyacrylamide (Compound 34)

Step 31a: (E)-3-(4-(Chlorosulfonyl)phenyl)acrylic acid (Compound 1305)

To neat chlorosulfonic acid (5.3 ml, 80 mmol) was added cinamic acid (1.47 g, 10 mmol) slowly at 0~5° C. The resulting mixture was stirred successively at 0° C. for 1 h, at ambient temperature for 1 h, and at 40~42° C. for 2 h. The mixture was poured into ice/water, filtered, washed with water, dried to give the product 1305 as a white solid (1.5 g, 60%): LCMS: 247 [M+1]$^+$. $^1$H NMR (400 MHz, DMSO-d$_6$) δ 5.53 (d, J=16 Hz, 1H), 7.61 (m, 5H).

Step 31b: (E)-Methyl 3-(4-(chlorosulfonyl)phenyl)acrylate (Compound 1306-34)

To a solution of SOCl2 (12 mL) in 1,2-dichloroethane (8 mL) was added 1305 (1.6 g, 6.5 mmol). The mixture was stirred at 80° C. for 1 h. and was then concentrated. The residue was added ice-cold methanol at 0° C., stirred for 5 minutes and warmed to room temperature for 10 minutes. Additional ice-cold water was added into the mixture to give a precipitate. The resulting solid was filtered and dried to give desired product 1306-34 (1.26 g, 75%) as a white solid: LCMS: 261 [M+1]+.

Step 31c: (E)-Methyl 3-(4-(N-(5-((5-tert-butyloxazol-2-yl)methylthio)thiazol-2-yl)-sulfamoyl)phenyl)acrylate (Compound 1307-34)

To a solution of the compound 0108 (228 mg, 0.85 mmol) in pyridine (1 mL) was added 1306-34 (385 mg, 1.48 mmol) under N$_2$ atmosphere at room temperature. The mixture was stirred at 50° C. for 2 h, followed by the addition of 2nd part of 1306-34 (385 mg, 1.48 mmol) in pyridine (1 mL). The resulting mixture was then stirred at 60° C. for 2.5 h. The reaction was concentrated to give a residue which was treated with 1N HCl. The resulting precipitate was filtered, washed with water and dried to give the crude product. The crude product was dissolved in methanol (20 mL) and then a solution of conc. H$_2$SO$_4$ (1.5 mL) was added. The mixture was heated to 80° C. for 1 h, cooled to room temperature and adjusted to pH 7. The solvent was removed under reduced pressure and the residue was added water, filtered, evaporated and dried to give product 1307-34 (420 mg, 85%): LCMS: 494 [M+1]$^+$. $^1$H NMR (400 MHz, DMSO-d$_6$) δ 1.17 (s, 9H), 3.74 (s, 3H), 4.11 (s, 2H), 6.77 (m, 2H), 7.41 (m, 1H), 7.71 (d, J=13.2 Hz, 1H), 7.76 (s, 1H), 7.78 (s, 1H), 7.91 (d, J=8.8 Hz, 2H), 12.96 (s, 1H).

Step 31d: (E)-3-(4-(N-(5-((5-Tert-butyloxazol-2-yl)methylthio)thiazol-2-yl)sulfamoyl)phenyl)-N-hydroxyacrylamide (Compound 34)

The title compound 34 was prepared as a light-red solid (70 mg, 17%) from compound 1307-34 (420 mg, 0.85 mmol) and freshly prepared hydroxylamine in methanol (1.77 M, 18 mL) using a procedure similar to that described for compound 26 (Example 23):LCMS: 495 [M+1]$^+$. $^1$H NMR (400 MHz, DMSO-d$_6$) δ 1.17 (s, 9H), 4.12 (s, 2H), 6.56 (d, J=16.0 Hz, 1H), 7.40 (s, 1H), 7.51 (d, J=27.6 Hz, 1H), 7.76 (m, 4H), 9.18 (s, 1H), 10.88 (s, 1H), 12.95 (s, 1H).

Example 32

Preparation of 4-(3-(2-(5-((5-tert-butyloxazol-2-yl)methylthio)-thiazol-2-ylamino)-2-oxoethyl)phenoxy)-N-hydroxybutanamide (Compound 35)

Step 32a: 2-(3-(4-Methoxy-4-oxobutoxy)phenyl)acetic acid (Compound 0202-35)

A mixture of m-hydroxyphenylacetic acid (1 g, 6.57 mmol), (bromomethyl)benzene (1.35 g, 7.9 mmol) and DBU (1 ml, 6.57 mol) in anhydrous acetonitrile was stirred at 70° C. overnight. The solvent was removed under reduce pressure and the residue was dissolved in ethyl acetate, washed with NaHCO$_3$, brine, dried (Na$_2$SO$_4$), and evaporated. The residue was washed with ether, filtered and dried to obtain product benzyl 2-(3-hydroxyphenyl)acetate (1.39 g, 87%): $^1$H NMR (400 MHz, DMSO-d$_6$) δ 3.62 (s, 2H), 5.10 (s, 2H), 6.68 (m, 3H), 7.09 (m, 1H), 7.34 (m, 5H), 9.48 (s, 1H).

A mixture of benzyl 2-(3-hydroxyphenyl)acetate (1.39 g, 5.74 mmol), ethyl 4-bromobutanoate (1.23 g, 6.3 mmol), anhydrous K$_2$CO$_3$ (1.98 g, 14.4 mmol) and anhydrous DMF (10 mL) was stirred at room temperature overnight. Water was added to the mixture and extracted with ethyl acetate. The organic layer was washed with water, brine, dried (Na$_2$SO$_4$) and concentrated. The residue was purified by column chromatography on silica gel (ethyl acetate in petroleum ether, 25% to 50% v/v) to yield ethyl 4-(3-(2-(benzyloxy)-2-oxoethyl)phenoxy)butanoate (2.05 g, 100%) as a white solid. $^1$H NMR (400 MHz, DMSO-d$_6$) δ 1.17 (t, J=7.2 Hz, 3H), 1.96 (m, 2H), 2.45 (t, J=7.2 Hz, 2H), δ 3.70 (s, 2H), 3.94 (t, J=6.4 Hz, 2H), 4.07 (q, J=7.2 Hz, 2H), 5.11 (s, 2H), 6.83 (m, 3H), 7.20 (t, 1H), 7.20 (m, 5H).

The mixture of ethyl 4-(3-(2-(benzyloxy)-2-oxoethyl)phenoxy)butanoate (2.05 g, 5.77 mmol) and Pd/C (0.207 g) in methanol was stirred at room temperature under H$_2$ overnight. The mixture was filtered and the filtrate was concentrated under reduce pressure. The residue was washed with ether, filtrated and dried to obtain 2-(3-(4-methoxy-4-oxobutoxy)phenyl)acetic acid (compound 0202-35) (1 g, 66%): LCMS: 267 [M+1]$^+$.

Step 32b: Methyl 4-(3-(2-(5-((5-tert-butyloxazol-2-yl)methylthio)thiazol-2-yl-amino)-2-oxoethyl)phenoxy)butanoate (Compound 0203-35)

A mixture of compound 0108 (500 mg, 1.85 mmol), EDCI·HCl (530 mg, 2.78 mmol), HOBt (375 mg, 2.78 mmol), 0202-35 (495 mg, 1.85 mmol) and DIEA (705 mg, 5.55 mmol) in DMF (10 ml) was stirred at room temperature for 24 hours. The mixture is diluted with ethyl acetate and washed with water (2×30 mL) and brine. The organic phase was concentrated under reduce pressure to give crude product 0203-35 (0.4 g) which was used directly to next step without further purification: LCMS: 518 [M+1]$^+$.

Step 32c: 4-(3-(2-(5-((5-Tert-butyloxazol-2-yl)methylthio)thiazol-2-ylamino)-2-oxo-ethyl)phenoxy)-N-hydroxybutanamide (Compound 35)

The title compound 35 was prepared as a pale white solid (100 mg, 26%) from compound 0203-35 (380 mg, 0.73 mmol) and freshly prepared hydroxylamine in methanol (1.77 M, 4 mL) using a procedure similar to that described for compound 26 (Example 23): m.p. 174~176° C., LCMS: 505 [M+1]$^+$; $^1$H NMR (500 MHz, DMSO-d$_6$) δ 1.14 (s, 9H), 1.92 (m, 2H), 2.12 (t, J=7.5 Hz, 2H), 3.70 (s, 2H), 3.93 (t, J=6.5 Hz, 2H), 4.04 (s, 2H), 6.70 (s, 1H), 6.83 (m, 3H), 6.87 (m, 1H), 7.40 (s, 1H), 8.72 (s, 1H), 10.43 (s, 1H), 12.25 (s, 1H).

Biological Assays:

As stated hereinbefore the derivatives defined in the present invention possess anti-proliferation activity. These properties may be assessed, for example, using one or more of the procedures set out below:

(a) An In Vitro Assay which Determines the Ability of a Test Compound to Inhibit CDK Activity.

Materials:

CDK2/cyclinE (Accession Number for CDK2; EMBL M68520, for cyclinE1; GenBank NM_001238):

C-terminal 6His-tagged, recombinant full-length CDK2 (MW=34 kDa) in complex with N-terminal GST-tagged, recombinant full-length cyclinE1 (MW=74 kDa) were expressed with baculovirus system in Sf21 cells. Recombinant proteins were purified using Ni2+/NTA agarose and the purity of recombinant protein complex was measured to be around 76% by SDS-PAGE and Coomassie blue staining. Specific Activity of recombinant CDK2/cyclinE was 1336 U/mg, where one unit of CDK2/cylinE1 activity is defined as 1 nmol phosphate incorporated into 0.1 mg/ml histone H1 per minute at 30° C. with a final ATP concentration of 100 μM. Enzyme was stored with concentration of 0.1 mg/ml in 50 mM Tris/HCl pH 7.5, 150 mM NaCl, 0.03% Brij-35, 0.1 mM EGTA, 0.2 mM PMSF, 1 mM benzamidine, 0.1% 2-mercaptoethanol, 270 mM sucrose.

CDK6/cyclinD3 (Accession Number for CDK6; GenBank X66365, for Cyclin D3; EMBL M90814):

N-terminal, 6His-tagged full-length human cdk6 (MW=38 kDa) complexed with N-terminal GST-tagged full-length human cyclin D3 (MW=59 kDa) were expressed in Sf21 cells. Recombinant protein complex was purified using glutathione-agarose and activated with CAK, and repurified with Ni2+/NTA-agarose column. Purity was measured to be at least 68%. Specific Activity was measured to be 39 U/mg, where one unit of cdk6/cyclinD3 activity is defined as 1 nmol phosphate incorporated into 0.1 mg/ml histone H1 per minute at 30° C. with a final ATP concentration of 100 μM. Enzyme was stored at concentration of 0.1 mg/ml in 50 mM Tris-HCl, pH 7.5, 270 mM sucrose, 150 mM NaCl, 1 mM benzamidine, 0.2 mM PMSF, 0.1% 2-mercaptoethanol, 0.1 mM EGTA, 0.03% Brij 35.

CDK1/cyclinB (Accession Number for CDK1; GenBankNM_001786, for cyclinB; EMBL M25753):

C-terminal 6His-tagged human full length cdk1 (MW=35 kDa), and N-terminal GST-tagged human full length cyclin B (MW=75 kDa) were expressed individually with baculovirus system in Sf21 insect cells. Recombinant proteins were purified using Ni2+/NTA-agarose and GST-agarose, respectively. The cdk1 was then activated using CAK and repurified by Q Sepharose and Ni2+/NTA-agarose. They were then mixed in vitro to form protein complex. The purity of these protein complex was estimated to be 80.5% by SDSPAGE and Coomassie blue staining. Specific Activity of recombinant enzyme was measyre to be 1329 U/mg, where one unit of cdk1/cyclinB activity is defined as 1 nmol phosphate incorporated into 0.1 mg/ml histone H1 per minute at 30° C. with a final ATP concentration of 100 mM. Enzyme was stored at concentration of 0.1 mg/ml in 50 mM Tris/HCl pH7.5, 150 mM NaCl, 0.1 mM EGTA, 0.03% Brij-35, 270 mM sucrose, 1 mM benzamidine, 0.2 mM PMSF, 0.1% 2-mercaptoethanol.

CDK2/cyclinA (Accession Number for CDK2; EMBL M68520, for Cyclin A; EMBL X51688):

C-terminal 6His-tagged human full length cdk2 (MW=35 kDa), and N-terminal GST-tagged human full length cyclinA (MW=75 kDa) were expressed individually with baculovirus system in Sf21 insect cells. Recombinant cdk2 protein was purified with Ni2+/NTA agarose and then activated using CAK and repurifed by Q Sepharose and Ni2+/NTA agarose. Recombinant cyclin A was purified using glutathione-agarose. They were then mixed in vitro to form protein complex. Recombinant protein complex was measured to be 67% in purity with SDS-PAGE and Coomassie blue staining. Specific Activity of purified enzyme was measure to be as 158 U/mg, where one unit of cdk2/cyclinA activity is defined as 1 nmol phosphate incorporated into 0.1 mg/ml histone H1 per minute at 30° C. with a final ATP concentration of 100 mM. Enzyme was stored at a concentration of 0.1 mg/ml in 50 mM Tris/HCl pH7.5, 150 mM NaCl, 0.1 mM EGTA, 0.03% Brij-35, 270 mM sucrose, 1 mM benzamidine, 0.2 mM PMSF, 0.1% 2-mercaptoethanol. Frozen solution.

CDK3/cyclinE (Accession Number for CDK3; GenBank X66357, for Cyclin E; GenBank NM_001238):

C-terminal 6His-tagged recombinant human full-length cdk3 (MW=36 kDa) were coexpressed with N-terminal GST-tagged recombinant human full-length cyclin E (MW=74 kDa) with baculovirus system in Sf21 insect cells. Recombinant protein complex was purified using Ni2+/NTA agarose and with purity to be 66% by SDS PAGE and Coomassie blue staining. Specific Activity of recombinant enzyme was measured to be 861 U/mg, where one unit of cdk3/cyclinE activity is defined as 1 nmol phosphate incorporated into 0.1 mg/ml histone H1 per minute at 30° C. with a final ATP concentration of 100 mM. Enzyme was stored at a concentration of 0.1 mg/ml in 50 mM Tris/HCl pH7.5, 150 mM NaCl 0.1 mM EGTA, 0.03% Brij 35, 270 mM sucrose, 1 mM benzamidine, 0.2 mM PMSF, 0.1% 2-mercaptoethanol.

CDK4/cyclinD1 (Accession Number for CDK4; NP_000066, for Cyclin D1; NP_444284)

Recombinant Human Full-length GST-tagged CDK-4 (MW=61.8 kDa) and cyclinD1 (MW=61.2 kDa) were expressed in insect cells. Recombinant enzyme was measure to have specific Activity equal to 190 nmole of phosphate transferred to RbING peptide substrate (INGSPRT-PRRGQNR) (SEQ ID NO. 1), per minute per mg of total protein at 30° C. Activity was determined at a final protein concentration at 8.33 µg/mL. Enzyme was stored at a concentration of 0.4 mg/ml in 50 mM Tris (pH 7.5), 150 mM NaCl, 0.5 mM EDTA, 0.02% Triton X-100, 2 mM DTT, 50% Glycerol.

CDK7/cyclinH1/MNAT1 (Accession Number for CDK7; NP_001790, for Cyclin H1; NP_001230, for MNAT1; NP_002422.1)

Recombinant Human Full-Length protein, Histidine-tagged CDK7 (MW=43.2 kDa), Histidine-tagged cyclin H1 (MW=42.6 kDa), Histidine-tagged MNAT1 (MW=40.5 kDa), were expressed in insect cells. Specific Activity of recombinant enzyme complex was measured to be equal to 94 nmole of phosphate transferred to CDK7/9tide substrate (YSPTSPSYSPTSPSYSPTSPSKKKK) (SEQ ID NO. 2), per minute per mg of total protein at 30° C. Activity was determined with a final protein concentration at 3.33 µg/mL. Enzyme was stored at a concentration of 0.42 mg/ml in 50 mM Tris (pH 7.5), 150 mM NaCl, 0.5 mM EDTA, 0.02% Triton X-100, 2 mM DTT, 50% Glycerol.

CDK9/cyclinT1 (Accession Number for CDK9; GenBank AF517840, for Cyclin T1; GenBank NM_001240)

C-terminal 6His-tagged, full-length recombinant, human cdk9 (MW=44 kDa) were co-expressed with untagged, full-length human cyclin T1 (MW=80.79 kDa) with baculovirus system in Sf21 insect cells. Recombinant protein complex was purified with $Ni^{2+}$/NTA agarose. Purity of recombinant protein was measured to be 50% by SDS-PAGE and Coomassie blue staining Specific Activity of purified enzyme was measured to be186 U/mg, where one unit of cdk9/cyclin T1 activity is defined as 1 nmol phosphate incorporated into 100 µM PDKtide (KTFCGTPEYLAPEVRREPRILSEEEQEM-FRDFDYIADWC) (SEQ ID NO. 3), per minute at 30° C. with a final ATP concentration of 100 µM. Enzyme was stored at a concentration of 0.1 mg/ml in 50 mM Tris-HCl, pH 7.5, 300 mM NaCl, 0.1 mM EGTA, 0.03% Brij-35, 270 mM sucrose, 1 mM benzamidine, 0.1% 2-mercaptoethanol, 0.2 mM PMSF.

Histon H1 (Substrate for CDK1, 2, 3, 6 and 7):

Histone H1 (Sigma cat# H4524), was purified as a lysine rich fraction from calf thymus with 93% purity (MW=21.5 kDa). Purified protein was stored at a concentration of 20 mg/ml=930 µM in distilled water.

RBC-CTF (Substrate for CDK4):

Human RB protein (S773-K928, MW=44.46 kDa), N-terminal GST-tagged was purified and followed with a factor Xa cleavage, which was performed in 4 mM concentration of glutathione, Purified protein was stocked at a concentration of 0.67 mg/ml.

PDKtide (Substrate for CDK9):

Synthetic peptide substrate with sequence of [KTFCGT-PEYLAPEVRREPRILSEEEQEMFRDFDYIADWC] (SEQ ID NO. 3), MW=4771.4.

Assay Conditions:

For CDK activity assay, p33 ATP tracers were incubated with purified recombinant specific combination of purified CDK kinases, cyclins and substrates to monitor the enzyme activity. In these assays, individual reactions were carried out in specific conditions describe below with reaction buffer: 20 mM HEPES (pH 7.5), 10 mM $MgCl_2$, 1 mM EGTA, 0.02% Brij 35, 0.02 mg/ml BSA, 0.1 mM $Na_3VO_4$, 2 mM DTT. An equal volume of 25% TCA was added to stop the reaction and precipitate the labeled peptides. Precipitated proteins were trapped onto glass fiber B filterplates and excess unlabeled p33 ATP was washed off. The plates were allowed to air-dry prior to the addition of 30 uL/well of Packard Microscint 20. The amount of incorporated isotope was measured using a Perkin Elmer TopCount plate reader. Different concentrations of compounds were added to reaction to assess the activity of compounds to inhibit PDGF-beta kinase. IC50 was calculated using Prism software with sigmoidal dose-response curve fitting.

CDK1/cyclinB:

1 nM CDK1/cyclinB and 20 µM Histon H1 were mixed in the reaction buffer with final concentration of 1 µM ATP and 1% DMSO. Reaction was performed for 2 hours at room temperature and with conversion rate of ATP is equal to 7.5%.

CDK2/cyclinE:

0.5 nM CDK2/cyclinE and 5 µM Histon H1 were mixed in the reaction buffer with final concentration of 1 µM ATP and 1% DMSO. Reaction was incubated for 2 hours at room temperature and conversion rate of ATP is about 4.5%.

CDK3/cyclinE:

0.5 nM CDK3/cyclinE and 20 µM Histon H1 were mixed in the reaction buffer with final concentration of 1 µM ATP and 1% DMSO. Reaction was incubated for 2 hours at room temperature and with conversion rate of ATP was measured to be 7.0%.

CDK4/cyclinD1:

2 nM CDK4/cyclinD1 and 1 µM RB-CTF were mixed in the reaction buffer with final concentration of 1 µM ATP and 1% DMSO. Reaction was incubated for 2 hours at room temperature and with conversion rate of ATP was measured to be 8.5%.

CDK6/cyclinD3:

50 nM CDK6/cyclinD3 and 5 µM Histon H1 were mixed in the reaction buffer with final concentration of 1 µM ATP and 1% DMSO. Reaction was incubated for 2 hours at room temperature and with conversion rate of ATP that was measured to be 13%.

CDK7/cyclinH1/MNAT1:

100 nM CDK7/cyclinH1/MNAT1 and 20 µM Histon H1 were mixed in the reaction buffer with 1 µM ATP and 1% DMSO. Reaction was incubated for 2 hours at room temperature and conversion rate of ATP was measured to be 5.5%.

CDK9/cyclinT1:

2 nM CDK9/cyclinT1 and 20 µM pdkTIDE were mixed in the reaction buffer with 1 µM ATP and 1% DMSO at final concentrations. Reaction was incubate for 2 hours at room temperature and conversion rate of ATP was measured to be 12%.

(b) An In Vitro Assay which Determines the Ability of a Test Compound to Inhibit HDAC Enzymatic Activity.

HDAC inhibitors were screened using an HDAC fluorimetric assay kit (AK-500, Biomol, Plymouth Meeting, Pa.). Test compounds were dissolved in dimethylsulphoxide (DMSO) to give a 20 mM working stock concentration. Fluorescence was measured on a WALLAC Victor 2 plate reader and reported as relative fluorescence units (RFU). Data were plotted using GraphPad Prism (v4.0a) and IC50's calculated using a sigmoidal dose response curve fitting algorithm. Each assay was setup as follows: Defrosted all kit components and kept on ice until use. Diluted HeLa nuclear extract 1:29 in Assay Buffer (50 mM Tris/Cl, pH 8.0, 137 mM NaCl, 2.7 mM KCl, 1 mM MgCl2). Prepared dilutions of Trichostatin A (TSA, positive control) and tested compounds in assay buffer (5× of final concentration). Diluted Fluor de LysTM Substrate in assay buffer to 100 uM (50 fold=2× final). Diluted Fluor de LysTM developer concentrate 20-fold (e.g. 50 µl plus 950 µl Assay Buffer) in cold assay buffer. Second, diluted the 0.2 mM Trichostatin A 100-fold in the 1× Developer (e.g. 10 µl in 1 ml; final Trichostatin A concentration in the 1× Developer=2 µM; final concentration after addition to HDAC/Substrate reaction=1 µM). Added Assay buffer, diluted trichostatin A or test inhibitor to appropriate wells of the microtiter plate. Added diluted HeLa extract or other HDAC sample to all wells except for negative controls. Allowed diluted Fluor de LysTM Substrate and the samples in the microtiter plate to equilibrate to assay temperature (e.g. 25 or 37° C. Initiated HDAC reactions by adding diluted substrate (25 µl) to each well and mixing thoroughly. Allowed HDAC reactions to proceed for 1 hour and then stopped them by addition of Fluor de LysTM Developer (50 µl). Incubated plate at room temperature (25° C.) for 10-15 min. Read samples in a microtiterplate reading fluorimeter capable of excitation at a wavelength in the range 350-380 nm and detection of emitted light in the range 440-460 nm.

The following TABLE B lists compounds representative of the invention and their activity in HDAC and CDK assays. In these assays, the following grading was used: I≥10 µM, 10 µM>II>1>µM, 1 M>III>0.1 µM, and IV≤0.1 µM for $IC_{50}$.

TABLE B

| Cmpd. No. | HDAC | CDK1 | CDK2/ cyclinE | CDK3 | CDK4 | CDK6/ cyclinD | CDK7 | CDK9 |
|---|---|---|---|---|---|---|---|---|
| 1 | I | | IV | | | | | |
| 2 | II | | IV | | | | | |
| 3 | II | | IV | | | | | |
| 4 | III | | IV | | | | | |
| 5 | III | | IV | | | III | | |
| 6 | III | | IV | | | III | | |
| 8 | IV | IV | IV | IV | III | III | III | IV |
| 9 | III | IV | IV | IV | IV | III | III | IV |
| 10 | III | | IV | | | | | |
| 11 | III | | IV | | | | | |
| 12 | III | | IV | | | III | | |
| 13 | I | | IV | | | III | | |
| 16 | III | | | | | | | |
| 17 | III | | IV | | | | | |
| 18 | III | | IV | | | | | |
| 19 | III | | IV | | | | | |
| 20 | IV | IV | IV | IV | III | II | II | IV |
| 21 | IV | | IV | | | | | |
| 22 | IV | | II | | | | | |
| 23 | IV | | IV | | | | | |
| 24 | III | | IV | | | | | |
| 25 | III | | IV | | | | | |
| 26 | III | | IV | | | | | |
| 27 | III | | IV | | | | | |
| 28 | III | | IV | | | | | |
| 29 | III | | IV | | | | | |
| 30 | III | | II | | | | | |
| 31 | IV | | IV | | | | | |
| 32 | IV | | II | | | | | |
| 33 | III | | No activity | | | | | |
| 34 | IV | | No activity | | | | | |
| 39 | III | | IV | | | | | |
| 40 | III | | IV | | | | | |

(c) An In Vivo Study of the Anti-Tumor Activity of Compound 8 in 30% CAPTISOL in the A375 Melanoma Nude Mouse Xenograft Model Mice were divided into two groups of 5 to 6 mice each. Tumor volumes at the commencement of treatment were 560±230 mm$^3$. Compound 8 in 30% CAPTISOL was administered daily (60 mg/Kg ip) to one group of animals, while the second group of animals received an equal volume of vehicle. Compound 8 was able to attenuate tumor growth in this model. As shown in FIG. 1, after 10 days, animals treated with compound 8 showed a 50% increase in tumor size whereas animals treated with vehicle showed about a 130% increase in tumor size.

Figure 2:
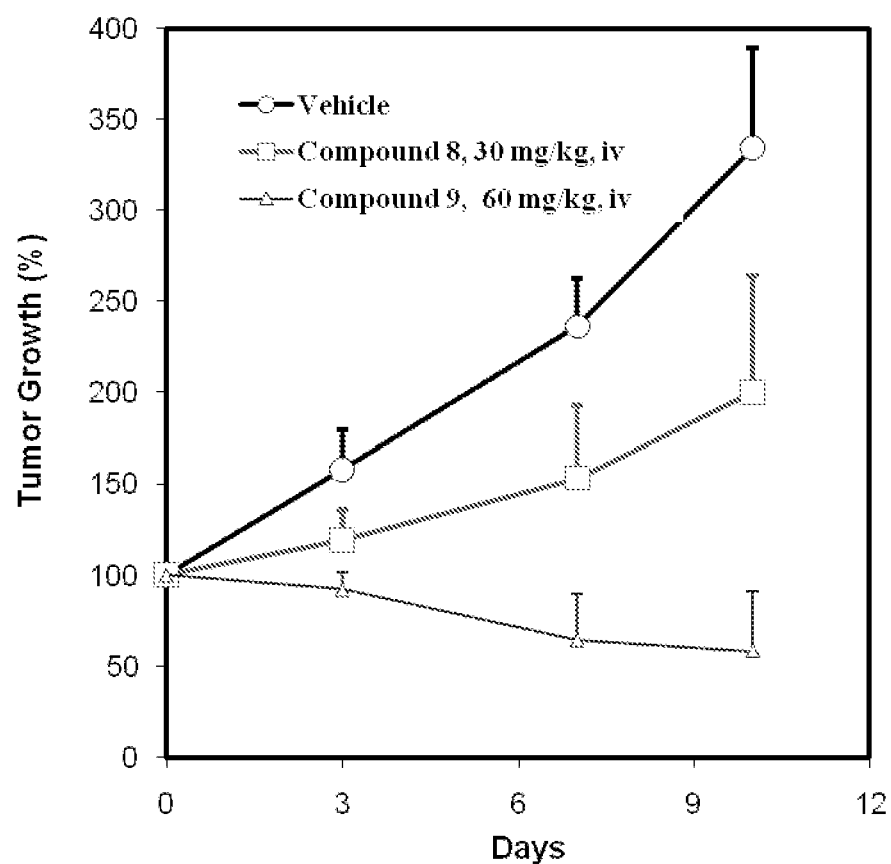
FIG. 2 is a graph of tumor size versus time for mice bearing HL60 AML xenograft tumors receiving 30 mg/Kg compound 8 in 30% CAPTISOL iv daily, 60 mg/Kg compound 9 in 30% CAPTISOL iv daily or vehicle only.

(d) An In Vivo Study of the Anti-Tumor Activity of Compounds 8 and 9 in 30% CAPTISOL in the HM60 AML Nude Mouse Xenograft Model Mice were divided into three groups of 4 mice each. Tumor volumes at the commencement of treatment were 157±56 mm$^3$. One group of mice received 30 mg/Kg compound 8 daily in 30% CAPTISOL, while a second group received 60 mg/Kg compound 9 in 30% CAPTISOL daily. The third group received an equivalent volume of vehicle daily. Both compounds were able to attenuate tumor growth in this model. As shown in FIG. 2, after 10 days, animals treated with compound 8 showed an approximate 90% increase in tumor size whereas animals treated with vehicle showed about a 230% change in tumor size. Animals treated with compound 9 exhibited a decrease in tumor size of about 50%.

Figure 3:
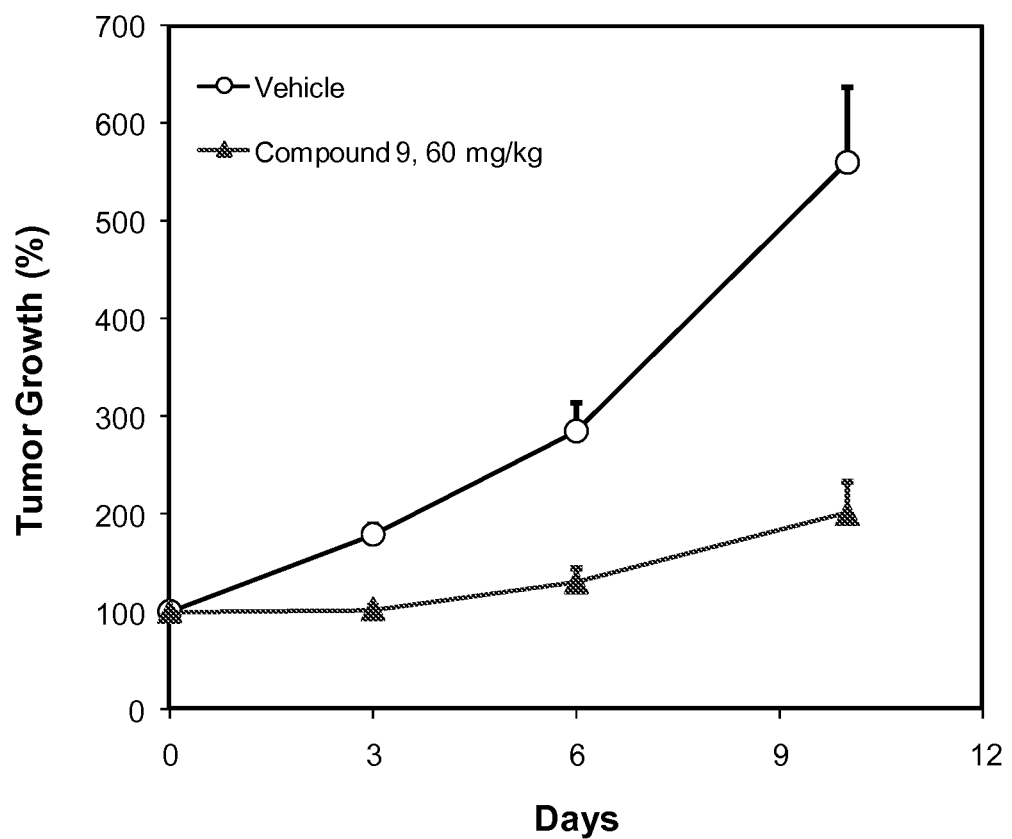
FIG. 3 is a graph of tumor size versus time for mice bearing OPM2 Multiple Myeloma xenograft tumors receiving either 60 mg/Kg compound 9 in 30% CAPTISOL iv daily or vehicle only.

(e) An In Vivo Study of the Anti-Tumor Activity of Compound 9 in 30% CAPTISOL in the OPM2 Multiple Myeloma Nude Mouse Xenograft Model Mice were divided into two groups of 7 mice each. Treatment began when the tumor sizes were 276±46 mm$^3$. Compound 9 in 30% CAPTISOL was administered to the animals daily at 60 mg/Kg iv. Compound 9 was able to attenuate tumor growth in this model. As shown in FIG. 3, after 10 days, animals treated with compound 9 showed an approximate 50% increase in tumor size whereas animals treated with vehicle showed about a 450% increase in tumor size.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by formula I:

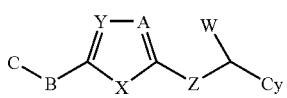

(I)

or a pharmaceutically acceptable salt or prodrug thereof, wherein

Cy is selected from aryl, substituted aryl, heteroaryl, substituted heteroaryl, heterocyclic, substituted heterocyclic, cycloalkyl and substituted cycloalkyl;

W is selected from hydrogen, halogen, acyl, aliphatic, substituted aliphatic, aryl, substituted aryl, heteroaryl, substituted heteroaryl, heterocyclic, substituted heterocyclic, cycloalkyl and substituted cycloalkyl;

Z is O, S, S(O), $SO_2$, $SO_2NH$, $NR_8$, $C_1$-$C_6$ alkyl, $C_2$-$C_6$ alkenyl, $C_2$-$C_6$ alkynyl, C(O) or C(O)NH;

Y is N;

A is $CR_8$, where $R_8$ is hydrogen, acyl, aliphatic or substituted aliphatic;

X is S;

B is a linker or a direct bond;

C is selected from:

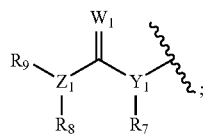

(a)

where $W_1$ is O or S; $Y_1$ is absent, N, or CH; $Z_1$ is N; $R_7$ and $R_9$ are independently hydrogen, OR', aliphatic or substituted aliphatic, wherein R' is hydrogen, aliphatic, substituted aliphatic or acyl; provided that if $R_7$ and $R_9$ are both present, one of $R_7$ or $R_9$ must be OR' and if Y is absent, $R_9$ must be OR'; and $R_8$ is hydrogen, acyl, aliphatic or substituted aliphatic;

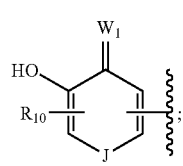

(b)

where $W_1$ is O or S; J is O, NH or $NCH_3$; and $R_{10}$ is hydrogen or lower alkyl;

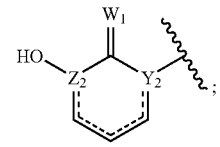

(c)

where $W_1$ is O or S; $Y_2$ and $Z_2$ are independently N, C or CH; and

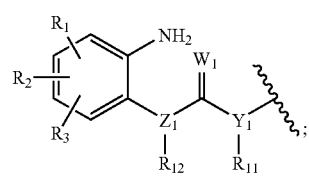

(d)

where $Z_1$, $Y_1$, and $W_1$ are as previously defined; $R_{11}$ and $R_{12}$ are independently selected from hydrogen or aliphatic; $R_1$, $R_2$ and $R_3$ are independently selected from hydrogen, hydroxy, amino, halogen, alkoxy, substituted alkoxy, alkylamino, substituted alkylamino, dialkylamino, substituted dialkylamino, substituted or unsubstituted alkylthio, substituted or unsubstituted alkylsulfonyl, $CF_3$, CN, $NO_2$, $N_3$, sulfonyl, acyl, aliphatic, substituted aliphatic, aryl, substituted aryl, heteroaryl, substituted heteroaryl, heterocyclic, and substituted heterocyclic.

2. A compound according to claim 1 wherein A is CH.

3. A compound according to claim 1 represented by formula (II):

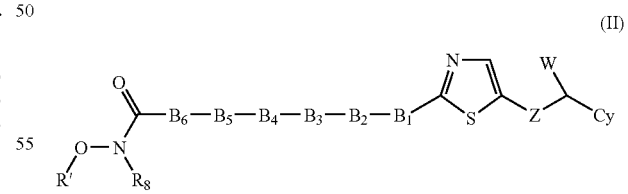

(II)

or a pharmaceutically acceptable salt or prodrug thereof, wherein $B_1$ is absent, $N(R_8)$, CO, $C_1$-$C_6$ alkyl, $C_2$-$C_6$ alkenyl, $C_2$-$C_6$ alkynyl, cycloalkyl, heterocyclic or aryl; $B_2$ is absent, O, S, SO, $SO_2$, $N(R_8)$ or CO; $B_3$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_4$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_5$ is absent, O, S, SO, $SO_2$, $N(R_8)$, CO, $C_1$-$C_6$ alkyl, $C_2$-$C_6$ alkenyl, C₂-C₆ alkynyl, cycloalkyl, heterocyclic, aryl, or heteroaryl; B₆ is absent, C₁-C₆ alkyl, C₂-C₆ alkenyl, C₂-C₆ alkynyl, cycloalkyl, heterocyclic, aryl, or heteroaryl; Cy, W, Z, R' and R₈ are as previously defined in claim 1.

4. A compound according to claim 1 represented by formula (III):

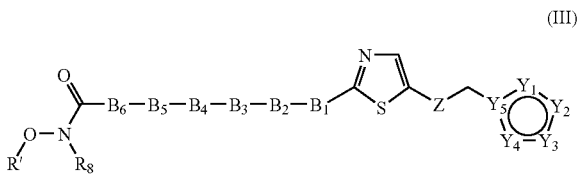

or a pharmaceutically acceptable salt or prodrug thereof, wherein Y₁-Y₄ are independently O, S, N, NR₈ or CR₂₁, where R₂₁ is independently selected from hydrogen, hydroxy, substituted hydroxy, amino, substituted amino, halogen, substituted or unsubstituted alkoxy, substituted or unsubstituted alkylamino, substituted or unsubstituted dialkylamino, substituted or unsubstituted thiol, CF₃, CN, NO₂, N₃, substituted carbonyl, sulfonyl, acyl, aliphatic, and substituted aliphatic; Y₅ is C or N; B₃ is absent, O, S, SO, SO₂, N(R₈), CO, C₁-C₆ alkyl, C₂-C₆ alkenyl, C₂-C₆ alkynyl, cycloalkyl, heterocyclic, aryl, or heteroaryl; B₄ is absent, O, S, SO, SO₂, N(R₈), CO, C₁-C₆ alkyl, C₂-C₆ alkenyl, C₂-C₆ alkynyl, cycloalkyl, heterocyclic, aryl, or heteroaryl; B₅ is absent, O, S, SO, SO₂, N(R₈), CO, C₁-C₆ alkyl, C₂-C₆ alkenyl, C₂-C₆ alkynyl, cycloalkyl, heterocyclic, aryl, or heteroaryl; B₆ is absent, C₁-C₆ alkyl, C₂-C₆ alkenyl, C₂-C₆ alkynyl, cycloalkyl, heterocyclic, aryl, or heteroaryl; Z, R' and R₈ are as previously defined in claim 1.

5. A compound according to claim 1 selected from the compounds delineated in Table A or a pharmaceutically acceptable salt or prodrug thereof:

TABLE A

| Compound # | Structure |
|---|---|
| 1 | 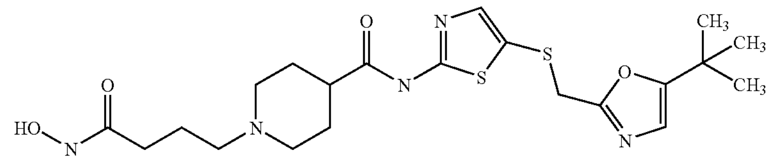 [SMILES: CC(C)(C)c1cnc(CSc2cnc(NC(=O)C3CCN(CCCC(=O)NO)CC3)s2)o1] |
| 2 | 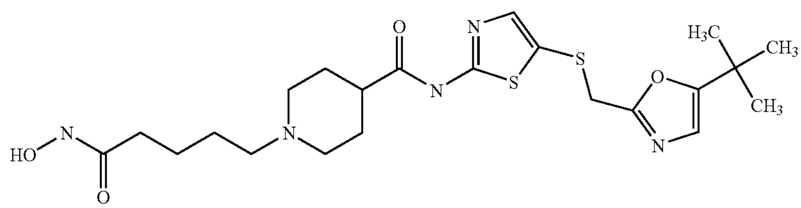 [SMILES: CC(C)(C)c1cnc(CSc2cnc(NC(=O)C3CCN(CCCCC(=O)NO)CC3)s2)o1] |
| 3 | 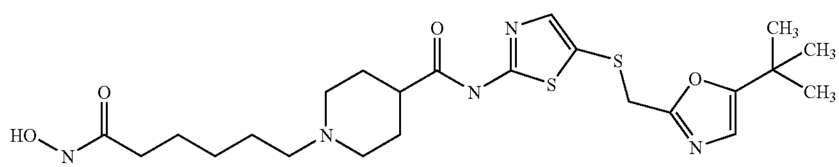 [SMILES: CC(C)(C)c1cnc(CSc2cnc(NC(=O)C3CCN(CCCCCC(=O)NO)CC3)s2)o1] |
| 4 | 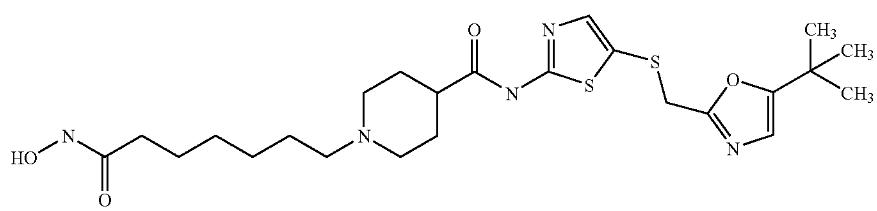 [SMILES: CC(C)(C)c1cnc(CSc2cnc(NC(=O)C3CCN(CCCCCCC(=O)NO)CC3)s2)o1] |
| 5 | 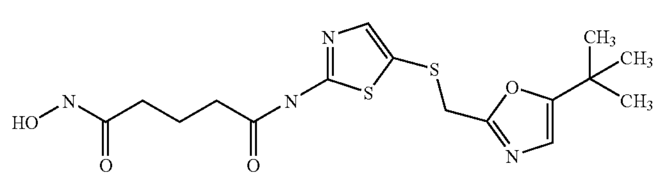 [SMILES: CC(C)(C)c1cnc(CSc2cnc(NC(=O)CCCC(=O)NO)s2)o1] |

TABLE A-continued
| Compound # | Structure |
|---|---|
| 6 | 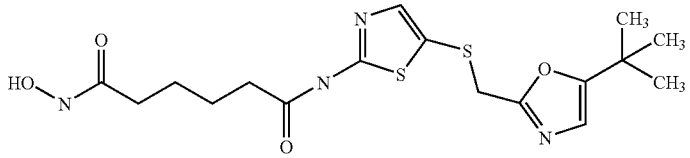 [SMILES: CC(C)(C)c1cnc(CSc2cnc(NC(=O)CCCCC(=O)NO)s2)o1] |
| 7 | 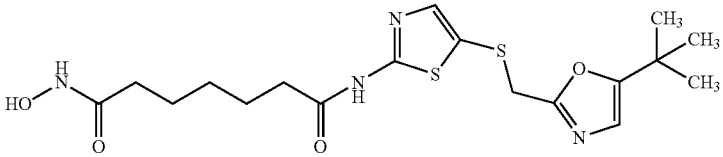 [SMILES: CC(C)(C)c1cnc(CSc2cnc(NC(=O)CCCCCC(=O)NO)s2)o1] |
| 8 | 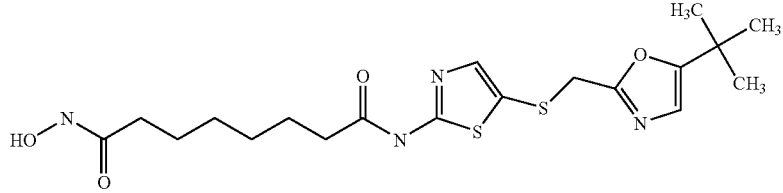 [SMILES: CC(C)(C)c1cnc(CSc2cnc(NC(=O)CCCCCCC(=O)NO)s2)o1] |
| 9 | 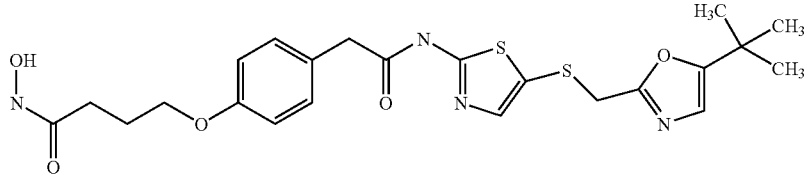 [SMILES: CC(C)(C)c1cnc(CSc2cnc(NC(=O)Cc3ccc(OCCCC(=O)NO)cc3)s2)o1] |
| 10 | 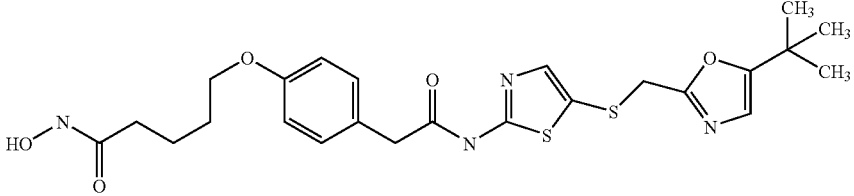 [SMILES: CC(C)(C)c1cnc(CSc2cnc(NC(=O)Cc3ccc(OCCCCC(=O)NO)cc3)s2)o1] |
| 11 | 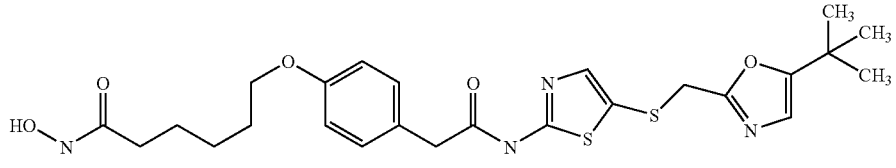 [SMILES: CC(C)(C)c1cnc(CSc2cnc(NC(=O)Cc3ccc(OCCCCCC(=O)NO)cc3)s2)o1] |
| 12 | 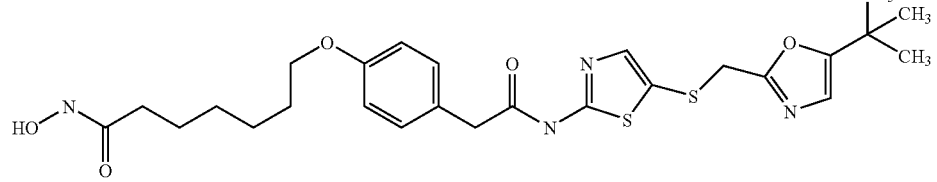 |
| 13 | 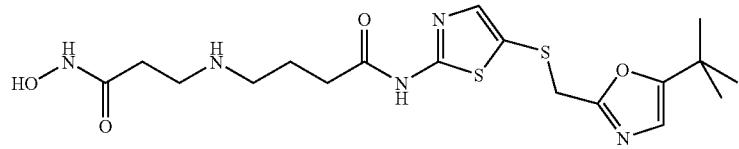 [SMILES: CC(C)(C)c1cnc(CSc2cnc(NC(=O)CCCNCCC(=O)NO)s2)o1] |

TABLE A-continued

| Compound # | Structure |
|---|---|
| 14 | 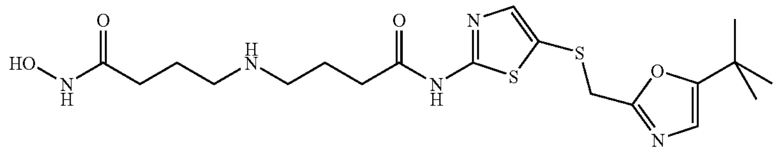 [SMILES: CC(C)(C)c1cnc(CSc2cnc(NC(=O)CCCNCCCC(=O)NO)s2)o1] |
| 15 | 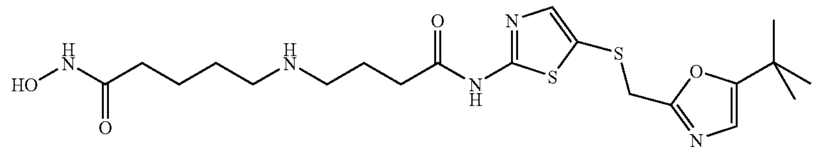 [SMILES: CC(C)(C)c1cnc(CSc2cnc(NC(=O)CCCNCCCCC(=O)NO)s2)o1] |
| 16 | 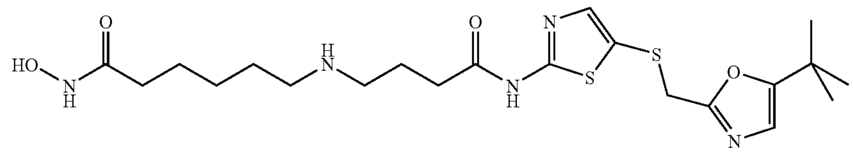 [SMILES: CC(C)(C)c1cnc(CSc2cnc(NC(=O)CCCNCCCCCC(=O)NO)s2)o1] |
| 17 | 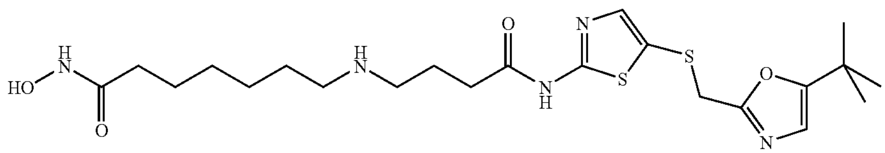 [SMILES: CC(C)(C)c1cnc(CSc2cnc(NC(=O)CCCNCCCCCCC(=O)NO)s2)o1] |
| 18 | 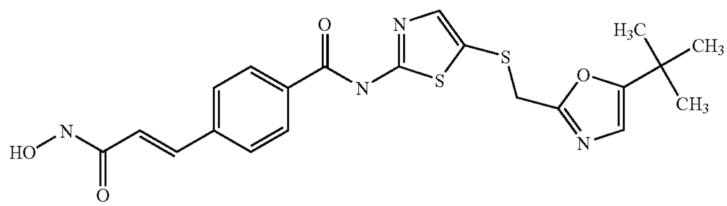 [SMILES: CC(C)(C)c1cnc(CSc2cnc(NC(=O)c3ccc(/C=C/C(=O)NO)cc3)s2)o1] |
| 19 | 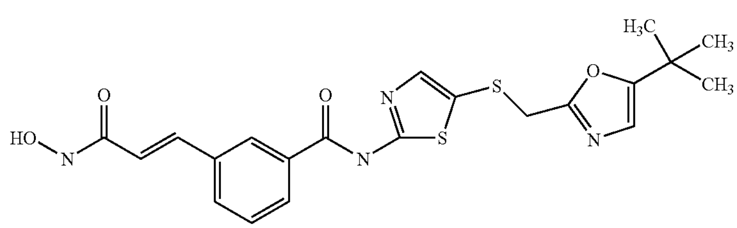 [SMILES: CC(C)(C)c1cnc(CSc2cnc(NC(=O)c3cccc(/C=C/C(=O)NO)c3)s2)o1] |
| 20 | 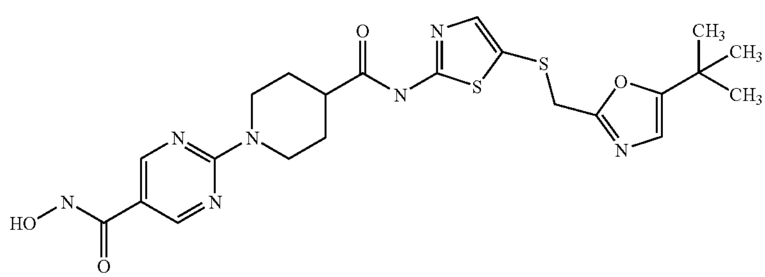 [SMILES: CC(C)(C)c1cnc(CSc2cnc(NC(=O)C3CCN(c4ncc(C(=O)NO)cn4)CC3)s2)o1] |

TABLE A-continued
| Compound # | Structure |
|---|---|
| 21 | 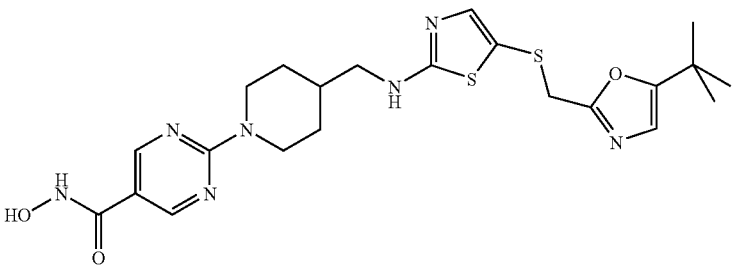 [SMILES: CC(C)(C)c1cnc(CSc2cnc(NCC3CCN(c4ncc(C(=O)NO)cn4)CC3)s2)o1] |
| 23 | 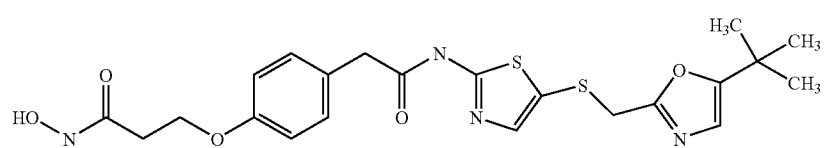 [SMILES: CC(C)(C)c1cnc(CSc2cnc(NC(=O)Cc3ccc(OCCC(=O)NO)cc3)s2)o1] |
| 24 | 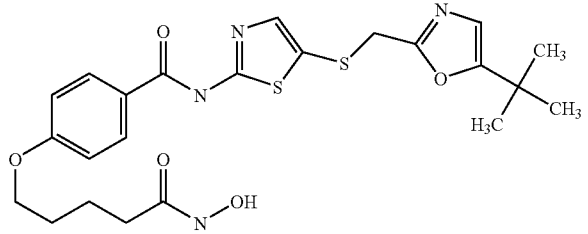 [SMILES: CC(C)(C)c1cnc(CSc2cnc(NC(=O)c3ccc(OCCCCC(=O)NO)cc3)s2)o1] |
| 25 | 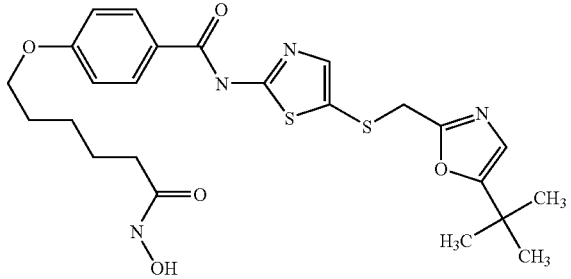 |
| 26 | 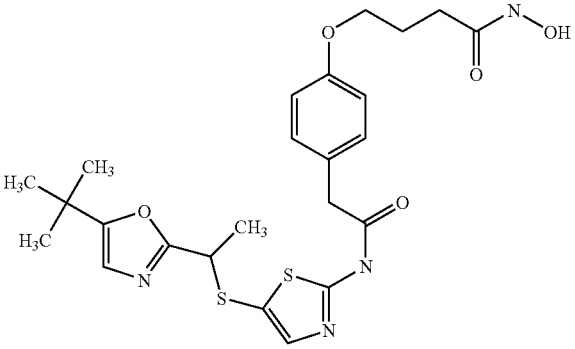 [SMILES: CC(Sc1cnc(NC(=O)Cc2ccc(OCCCC(=O)NO)cc2)s1)c1ncc(C(C)(C)C)o1] |

TABLE A-continued

| Compound # | Structure |
|---|---|
| 27 | (structure) |
| 28 | (structure) |
| 29 | (structure) |
| 31 | (structure) |
| 32 | (structure) |

TABLE A-continued
| Compound # | Structure |
|---|---|
| 33 | 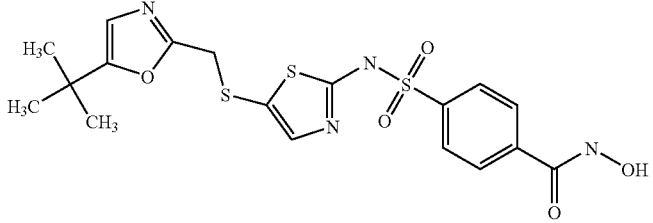 [SMILES: CC(C)(C)c1cnc(CSc2cnc(NS(=O)(=O)c3ccc(C(=O)NO)cc3)s2)o1] |
| 34 | 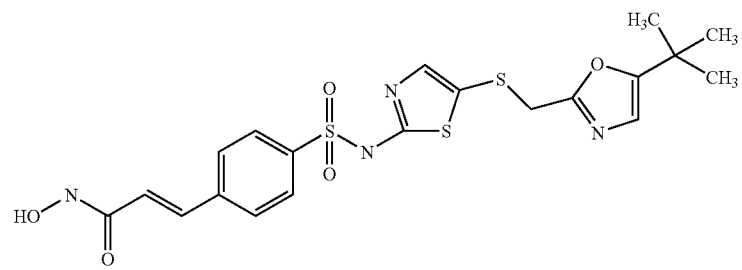 [SMILES: CC(C)(C)c1cnc(CSc2cnc(NS(=O)(=O)c3ccc(/C=C/C(=O)NO)cc3)s2)o1] |
| 35 | 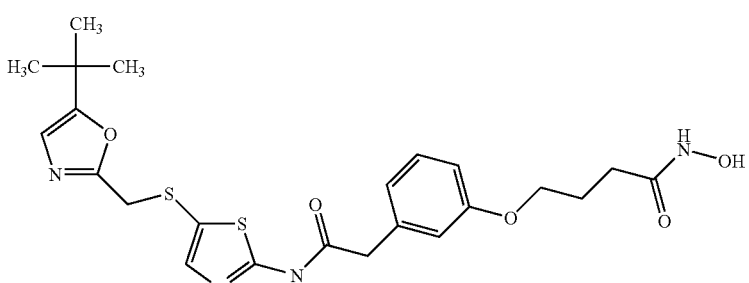 |
| 36 | 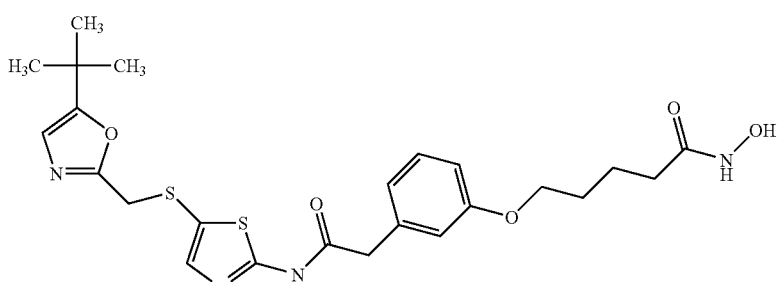 |
| 37 | 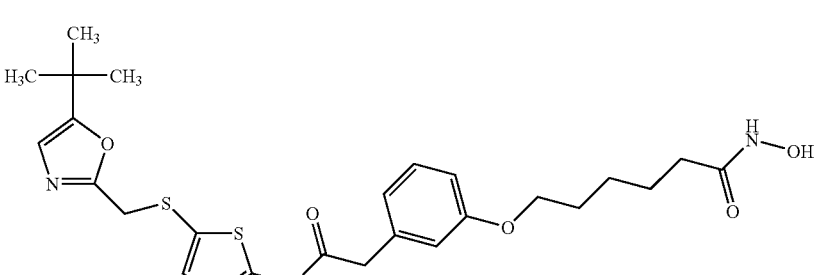 |

TABLE A-continued

| Compound # | Structure |
|---|---|
| 38 | 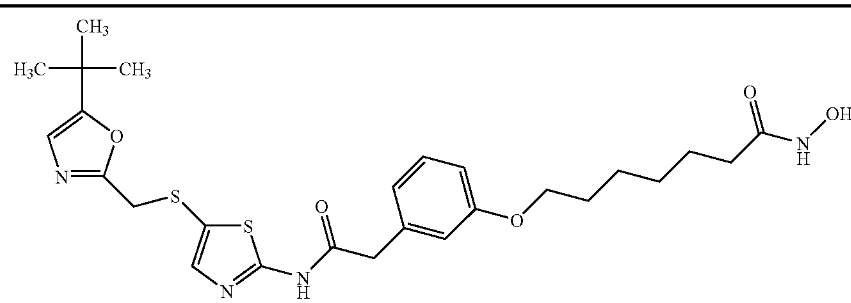 |
| 39 | 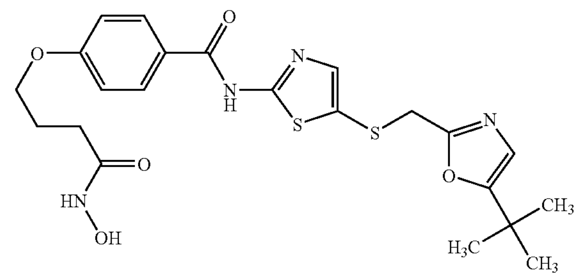 [SMILES: CC(C)(C)c1cnc(CSc2cnc(NC(=O)c3ccc(OCCCC(=O)NO)cc3)s2)o1] |
| 40 | 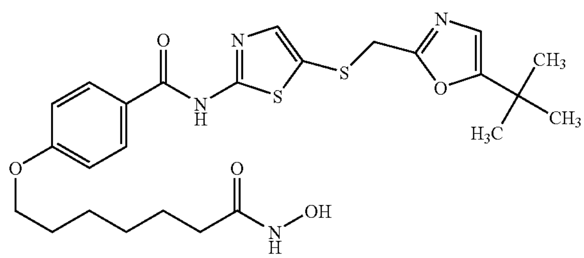 [SMILES: CC(C)(C)c1cnc(CSc2cnc(NC(=O)c3ccc(OCCCCCCC(=O)NO)cc3)s2)o1] |
| 41 | 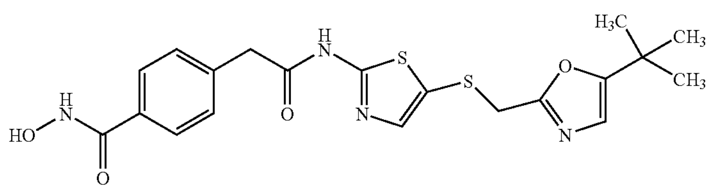 [SMILES: CC(C)(C)c1cnc(CSc2cnc(NC(=O)Cc3ccc(C(=O)NO)cc3)s2)o1] |
| 42 | 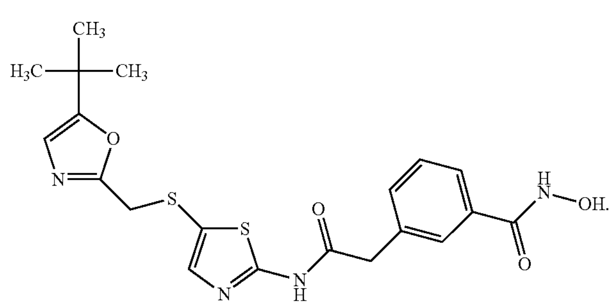 [SMILES: CC(C)(C)c1cnc(CSc2cnc(NC(=O)Cc3cccc(C(=O)NO)c3)s2)o1] |

6. A pharmaceutical composition comprising as an active ingredient a compound of claim 1 and a pharmaceutically acceptable carrier.

7. A method of treating cell proliferative disorder that requires or is facilitated by cyclin dependent kinase activity in a subject in need thereof, the method comprising administering to the subject a therapeutically effective amount of the pharmaceutical composition of claim 6.

8. A method of treating an HDAC-mediated disease comprising administering to a subject in need thereof a pharmaceutical composition of claim 6.

9. A method of treating cell proliferative disorder that relates to cyclin dependent kinase activity and HDAC comprising administering to a subject in need thereof a pharmaceutical composition of claim 6.

10. The method of claim 9, wherein said cell proliferative disorder is selected from the group consisting of papilloma, blastoglioma, Kaposi's sarcoma, melanoma, non-small cell lung cancer, ovarian cancer, prostate cancer, colon cancer, squamous cell carcinoma, astrocytoma, head cancer, neck cancer, bladder cancer, breast cancer, lung cancer, colorectal cancer, thyroid cancer, pancreatic cancer, renal cell carcinoma, gastric cancer, hepatocellular carcinoma, neuroblastoma, leukemia, lymphoma, vulcar cancer, Hodgkin's disease and Burkitt's disease.

11. A method for treating a viral infection selected from the group consisting of HIV, human papilloma virus, herpes virus, poxvirus, Epstein-Barr virus, Sindbis virus and adenovirus comprising administering to a subject in need thereof a pharmaceutical composition of claim 6.

\* \* \* \* \*

SEQUENCE LISTING

```
<160> NUMBER OF SEQ ID NOS: 3

<210> SEQ ID NO 1
<211> LENGTH: 14
<212> TYPE: PRT
<213> ORGANISM: Artificial Sequence
<220> FEATURE:
<223> OTHER INFORMATION: Synthetic

<400> SEQUENCE: 1

Ile Asn Gly Ser Pro Arg Thr Pro Arg Arg Gly Gln Asn Arg
1               5                   10

<210> SEQ ID NO 2
<211> LENGTH: 25
<212> TYPE: PRT
<213> ORGANISM: Artificial Sequence
<220> FEATURE:
<223> OTHER INFORMATION: Synthetic

<400> SEQUENCE: 2

Tyr Ser Pro Thr Ser Pro Ser Tyr Ser Pro Thr Ser Pro Ser Tyr Ser
1               5                   10                  15

Pro Thr Ser Pro Ser Lys Lys Lys Lys
            20                  25

<210> SEQ ID NO 3
<211> LENGTH: 39
<212> TYPE: PRT
<213> ORGANISM: Artificial Sequence
<220> FEATURE:
<223> OTHER INFORMATION: Synthetic
```

```
<400> SEQUENCE: 3

Lys Thr Phe Cys Gly Thr Pro Glu Tyr Leu Ala Pro Glu Val Arg Arg
 1               5                  10                  15

Glu Pro Arg Ile Leu Ser Glu Glu Glu Gln Glu Met Phe Arg Asp Phe
                20                  25                  30

Asp Tyr Ile Ala Asp Trp Cys
                35
```